(12) United States Patent
Gupta et al.

(10) Patent No.: US 9,724,095 B2
(45) Date of Patent: Aug. 8, 2017

(54) SURGICAL FASTENER APPLYING APPARATUS

(75) Inventors: Arvind Kumar Gupta, Uttar-Pradesh (IN); Nikhik R. Katre, Maharashtra (IN); Kiran Garilkipati, Andhra Pradesh (IN); Sekar Perumal, Tamilnadu (IN); Rajesh T. Shelke, Banglore (IN); Cinish P. Varghese, Adimaly (IN); Richard Roland Bueno, Madison, CT (US)

(73) Assignee: Covidien LP, Mansfield, MA (US)

( * ) Notice: Subject to any disclaimer, the term of this patent is extended or adjusted under 35 U.S.C. 154(b) by 1145 days.

(21) Appl. No.: 13/546,974

(22) Filed: Jul. 11, 2012

(65) Prior Publication Data
US 2013/0037595 A1 Feb. 14, 2013

Related U.S. Application Data

(60) Provisional application No. 61/521,070, filed on Aug. 8, 2011.

(51) Int. Cl.
*A61B 17/068* (2006.01)
*A61B 17/072* (2006.01)
(Continued)

(52) U.S. Cl.
CPC ...... *A61B 17/07207* (2013.01); *A61B 17/068* (2013.01); *A61B 17/0682* (2013.01);
(Continued)

(58) Field of Classification Search
CPC .......... A61B 17/105; A61B 2017/0688; A61B 17/0686; A61B 17/07207; A61B 17/068; A61B 17/0682
See application file for complete search history.

(56) References Cited

U.S. PATENT DOCUMENTS

| 3,079,606 A | 3/1963 | Bobrov et al. |
| 3,490,675 A | 1/1970 | Green et al. |

(Continued)

FOREIGN PATENT DOCUMENTS

| AU | 198654765 | 9/1986 |
| CN | 102056553 A | 5/2011 |

(Continued)

OTHER PUBLICATIONS

International Search Report for PCT/US12/49353 date of completion is Oct. 31, 2012 (5 pages).
(Continued)

*Primary Examiner* — Hemant M Desai
*Assistant Examiner* — Eduardo R Ferrero

(57) ABSTRACT

A surgical fastener applying apparatus includes an anvil half-section and a cartridge-receiving half-section including an elongated channel member having a pair of opposed openings defined through sidewalls thereof. A disposable assembly including a single use loading unit and a single use firing unit is configured to be releasably supported within the cartridge-receiving half-section. The disposable assembly includes a stationary housing for supporting the firing unit which includes a distal extension for supporting the single use loading unit. The stationary housing includes a pair of flared tabs configured to be releasably received within the openings of the cartridge-receiving half-section to releasably engage the disposable assembly within the cartridge-receiving half-section.

8 Claims, 31 Drawing Sheets

(51) Int. Cl.
*A61B 17/00* (2006.01)
*A61B 90/00* (2016.01)

(52) U.S. Cl.
CPC ... *A61B 17/0686* (2013.01); *A61B 2017/0023* (2013.01); *A61B 2017/00464* (2013.01); *A61B 2017/00473* (2013.01); *A61B 2090/0814* (2016.02); *A61B 2090/08021* (2016.02); *A61B 2560/0285* (2013.01)

(56) References Cited

U.S. PATENT DOCUMENTS

| | | |
|---|---|---|
| 3,499,591 A | 3/1970 | Green |
| 3,777,538 A | 12/1973 | Weatherly et al. |
| 3,882,854 A | 5/1975 | Hulka et al. |
| 4,027,510 A | 6/1977 | Hiltebrandt |
| 4,086,926 A | 5/1978 | Green et al. |
| 4,244,372 A | 1/1981 | Kapitanov et al. |
| 4,429,695 A | 2/1984 | Green |
| 4,505,414 A | 3/1985 | Filipi |
| 4,520,817 A | 6/1985 | Green |
| 4,550,870 A | 11/1985 | Krumme et al. |
| 4,589,413 A | 5/1986 | Malyshev et al. |
| 4,596,351 A | 6/1986 | Fedotov et al. |
| 4,602,634 A | 7/1986 | Barkley |
| 4,605,001 A | 8/1986 | Rothfuss et al. |
| 4,608,981 A | 9/1986 | Rothfuss et al. |
| 4,610,383 A | 9/1986 | Rothfuss et al. |
| 4,633,861 A | 1/1987 | Chow et al. |
| 4,633,874 A * | 1/1987 | Chow et al. ............... 227/176.1 |
| 4,671,445 A | 6/1987 | Barker et al. |
| 4,700,703 A | 10/1987 | Resnick et al. |
| 4,703,887 A | 11/1987 | Clanton et al. |
| 4,728,020 A | 3/1988 | Green et al. |
| 4,752,024 A | 6/1988 | Green et al. |
| 4,784,137 A | 11/1988 | Kulik et al. |
| 4,863,088 A | 9/1989 | Redmond et al. |
| 4,869,415 A | 9/1989 | Fox |
| 4,892,244 A | 1/1990 | Fox et al. |
| 4,955,959 A * | 9/1990 | Tompkins et al. ......... 227/178.1 |
| 4,978,049 A | 12/1990 | Green |
| 4,991,764 A | 2/1991 | Mericle |
| 5,014,899 A | 5/1991 | Presty et al. |
| 5,031,814 A | 7/1991 | Tompkins et al. |
| 5,040,715 A | 8/1991 | Green et al. |
| 5,065,929 A * | 11/1991 | Schulze et al. ................. 227/19 |
| 5,071,430 A | 12/1991 | deSalis et al. |
| 5,074,454 A | 12/1991 | Peters |
| 5,083,695 A | 1/1992 | Foslien et al. |
| 5,084,057 A | 1/1992 | Green et al. |
| 5,106,008 A * | 4/1992 | Tompkins et al. ......... 227/178.1 |
| 5,111,987 A | 5/1992 | Moeinzadeh et al. |
| 5,129,570 A * | 7/1992 | Schulze et al. ............ 227/175.2 |
| 5,141,144 A | 8/1992 | Foslien et al. |
| 5,156,315 A | 10/1992 | Green et al. |
| 5,156,614 A | 10/1992 | Green et al. |
| 5,163,943 A | 11/1992 | Mohiuddin et al. |
| 5,170,925 A | 12/1992 | Madden et al. |
| 5,171,247 A | 12/1992 | Hughetti et al. |
| 5,173,133 A | 12/1992 | Morin et al. |
| 5,180,092 A | 1/1993 | Crainich |
| 5,188,274 A * | 2/1993 | Moeinzadeh et al. ..... 227/180.1 |
| 5,220,928 A | 6/1993 | Oddsen et al. |
| 5,221,036 A | 6/1993 | Takase |
| 5,242,457 A | 9/1993 | Akopov et al. |
| 5,246,156 A | 9/1993 | Rothfuss et al. |
| 5,253,793 A | 10/1993 | Green et al. |
| 5,263,629 A | 11/1993 | Trumbull et al. |
| RE34,519 E | 1/1994 | Fox et al. |
| 5,275,323 A | 1/1994 | Schulze et al. |
| 5,282,807 A | 2/1994 | Knoepfler |
| 5,289,963 A | 3/1994 | McGarry et al. |
| 5,307,976 A | 5/1994 | Olson et al. |
| 5,308,576 A | 5/1994 | Green et al. |
| 5,312,023 A | 5/1994 | Green et al. |
| 5,318,221 A | 6/1994 | Green et al. |
| 5,326,013 A | 7/1994 | Green et al. |
| 5,328,077 A | 7/1994 | Lou |
| 5,330,486 A | 7/1994 | Wilk |
| 5,332,142 A | 7/1994 | Robinson et al. |
| 5,336,232 A | 8/1994 | Green et al. |
| 5,344,061 A | 9/1994 | Crainich |
| 5,352,238 A | 10/1994 | Green et al. |
| 5,356,064 A | 10/1994 | Green et al. |
| 5,358,506 A | 10/1994 | Green et al. |
| 5,364,001 A | 11/1994 | Bryan |
| 5,364,002 A | 11/1994 | Green et al. |
| 5,364,003 A | 11/1994 | Williamson, IV |
| 5,366,133 A | 11/1994 | Geiste |
| 5,376,095 A | 12/1994 | Ortiz |
| 5,379,933 A | 1/1995 | Green et al. |
| 5,381,943 A | 1/1995 | Allen et al. |
| 5,382,255 A | 1/1995 | Castro et al. |
| 5,383,880 A | 1/1995 | Hooven |
| 5,389,098 A | 2/1995 | Tsuruta et al. |
| 5,395,033 A | 3/1995 | Byrne et al. |
| 5,395,034 A | 3/1995 | Allen et al. |
| 5,397,046 A | 3/1995 | Savage et al. |
| 5,397,324 A | 3/1995 | Carroll et al. |
| 5,403,312 A | 4/1995 | Yates et al. |
| 5,405,072 A | 4/1995 | Zlock et al. |
| 5,407,293 A | 4/1995 | Crainich |
| 5,413,268 A | 5/1995 | Green et al. |
| 5,415,334 A | 5/1995 | Williamson, IV et al. |
| 5,415,335 A | 5/1995 | Knodell, Jr. |
| 5,417,361 A | 5/1995 | Williamson, IV |
| 5,423,471 A | 6/1995 | Mastri et al. |
| 5,425,745 A | 6/1995 | Green et al. |
| 5,431,322 A | 7/1995 | Green et al. |
| 5,431,323 A | 7/1995 | Smith et al. |
| 5,433,721 A | 7/1995 | Hooven et al. |
| 5,441,193 A | 8/1995 | Gravener |
| 5,445,304 A * | 8/1995 | Plyley et al. ............... 227/176.1 |
| 5,447,265 A | 9/1995 | Vidal et al. |
| 5,452,837 A | 9/1995 | Williamson, IV et al. |
| 5,456,401 A | 10/1995 | Green et al. |
| 5,464,300 A | 11/1995 | Crainich |
| 5,465,895 A | 11/1995 | Knodel et al. |
| 5,467,911 A | 11/1995 | Tsuruta et al. |
| 5,470,007 A | 11/1995 | Plyley et al. |
| 5,470,010 A | 11/1995 | Rothfuss et al. |
| 5,472,132 A | 12/1995 | Savage et al. |
| 5,474,566 A | 12/1995 | Alesi et al. |
| 5,476,206 A | 12/1995 | Green et al. |
| 5,478,003 A | 12/1995 | Green et al. |
| 5,480,089 A | 1/1996 | Blewett |
| 5,482,197 A | 1/1996 | Green et al. |
| 5,484,095 A | 1/1996 | Green et al. |
| 5,484,451 A | 1/1996 | Akopov et al. |
| 5,485,947 A | 1/1996 | Olson et al. |
| 5,485,952 A | 1/1996 | Fontayne |
| 5,486,185 A | 1/1996 | Freitas et al. |
| 5,487,499 A | 1/1996 | Sorrentino et al. |
| 5,487,500 A | 1/1996 | Knodel et al. |
| 5,489,058 A | 2/1996 | Plyley et al. |
| 5,490,856 A | 2/1996 | Person et al. |
| 5,497,933 A | 3/1996 | DeFonzo et al. |
| 5,501,689 A | 3/1996 | Green et al. |
| 5,505,363 A | 4/1996 | Green et al. |
| 5,507,426 A | 4/1996 | Young et al. |
| 5,518,163 A | 5/1996 | Hooven |
| 5,518,164 A | 5/1996 | Hooven |
| 5,529,235 A | 6/1996 | Boiarski et al. |
| 5,531,744 A | 7/1996 | Nardella et al. |
| 5,535,934 A | 7/1996 | Boiarski et al. |
| 5,535,935 A | 7/1996 | Vidal et al. |
| 5,535,937 A | 7/1996 | Boiarski et al. |
| 5,540,375 A | 7/1996 | Bolanos et al. |
| 5,542,594 A | 8/1996 | McKean et al. |
| 5,549,628 A | 8/1996 | Cooper et al. |
| 5,551,622 A | 9/1996 | Yoon |
| 5,553,765 A | 9/1996 | Knodel et al. |
| 5,554,164 A | 9/1996 | Wilson et al. |
| 5,554,169 A | 9/1996 | Green et al. |

(56) References Cited

U.S. PATENT DOCUMENTS

| | | | |
|---|---|---|---|
| 5,560,530 | A | 10/1996 | Bolanos et al. |
| 5,560,532 | A | 10/1996 | DeFonzo et al. |
| 5,562,239 | A | 10/1996 | Boiarski et al. |
| 5,562,241 | A | 10/1996 | Knodel et al. |
| 5,562,682 | A | 10/1996 | Oberlin et al. |
| 5,562,701 | A | 10/1996 | Huitema et al. |
| 5,564,615 | A | 10/1996 | Bishop et al. |
| 5,571,116 | A | 11/1996 | Bolanos et al. |
| 5,573,169 | A | 11/1996 | Green et al. |
| 5,573,543 | A | 11/1996 | Akopov et al. |
| 5,575,799 | A | 11/1996 | Bolanos et al. |
| 5,575,803 | A | 11/1996 | Cooper et al. |
| 5,577,654 | A | 11/1996 | Bishop |
| 5,579,107 | A | 11/1996 | Wright et al. |
| 5,584,425 | A | 12/1996 | Savage et al. |
| 5,586,711 | A | 12/1996 | Plyley et al. |
| 5,588,580 | A | 12/1996 | Paul et al. |
| 5,588,581 | A | 12/1996 | Conlon et al. |
| 5,597,107 | A | 1/1997 | Knodel et al. |
| 5,601,224 | A | 2/1997 | Bishop et al. |
| 5,607,095 | A | 3/1997 | Smith et al. |
| 5,615,820 | A | 4/1997 | Viola |
| 5,618,291 | A | 4/1997 | Thompson et al. |
| 5,624,452 | A | 4/1997 | Yates |
| 5,626,587 | A | 5/1997 | Bishop et al. |
| 5,628,446 | A | 5/1997 | Geiste et al. |
| 5,630,539 | A | 5/1997 | Plyley et al. |
| 5,630,540 | A | 5/1997 | Blewett |
| 5,630,541 | A | 5/1997 | Williamson, IV et al. |
| 5,632,432 | A | 5/1997 | Schulze et al. |
| 5,634,584 | A | 6/1997 | Okorocha et al. |
| 5,636,779 | A | 6/1997 | Palmer |
| 5,636,780 | A | 6/1997 | Green et al. |
| 5,645,209 | A | 7/1997 | Green et al. |
| 5,647,526 | A | 7/1997 | Green et al. |
| 5,651,491 | A * | 7/1997 | Heaton et al. ............. 227/175.1 |
| 5,653,373 | A | 8/1997 | Green et al. |
| 5,653,374 | A | 8/1997 | Young et al. |
| 5,653,721 | A | 8/1997 | Knodel et al. |
| 5,655,698 | A | 8/1997 | Yoon |
| 5,657,921 | A | 8/1997 | Young et al. |
| 5,658,300 | A | 8/1997 | Bito et al. |
| 5,662,258 | A | 9/1997 | Knodel et al. |
| 5,662,259 | A | 9/1997 | Yoon |
| 5,662,260 | A | 9/1997 | Yoon |
| 5,662,662 | A | 9/1997 | Bishop et al. |
| 5,662,666 | A | 9/1997 | Onuki et al. |
| 5,665,085 | A | 9/1997 | Nardella |
| 5,667,517 | A | 9/1997 | Hooven |
| 5,669,544 | A | 9/1997 | Schulze et al. |
| 5,673,840 | A | 10/1997 | Schulze et al. |
| 5,673,841 | A | 10/1997 | Schulze et al. |
| 5,673,842 | A | 10/1997 | Bittner et al. |
| 5,676,674 | A | 10/1997 | Bolanos et al. |
| 5,680,981 | A | 10/1997 | Mililli et al. |
| 5,680,982 | A | 10/1997 | Schulze et al. |
| 5,680,983 | A | 10/1997 | Plyley et al. |
| 5,690,269 | A | 11/1997 | Bolanos et al. |
| 5,692,668 | A | 12/1997 | Schulze et al. |
| 5,697,542 | A | 12/1997 | Knodel et al. |
| 5,702,409 | A | 12/1997 | Rayburn et al. |
| 5,704,534 | A | 1/1998 | Huitema et al. |
| 5,706,997 | A | 1/1998 | Green et al. |
| 5,709,334 | A | 1/1998 | Sorrentino et al. |
| 5,711,472 | A | 1/1998 | Bryan |
| 5,713,505 | A | 2/1998 | Huitema |
| 5,715,988 | A | 2/1998 | Palmer |
| 5,716,366 | A | 2/1998 | Yates |
| 5,718,359 | A * | 2/1998 | Palmer et al. ............. 227/175.2 |
| 5,725,536 | A | 3/1998 | Oberlin et al. |
| 5,725,554 | A | 3/1998 | Simon et al. |
| 5,728,110 | A | 3/1998 | Vidal et al. |
| 5,732,806 | A | 3/1998 | Foshee et al. |
| 5,735,848 | A | 4/1998 | Yates et al. |
| 5,743,456 | A | 4/1998 | Jones et al. |
| 5,749,893 | A | 5/1998 | Vidal et al. |
| 5,752,644 | A | 5/1998 | Bolanos et al. |
| 5,762,255 | A | 6/1998 | Chrisman et al. |
| 5,762,256 | A | 6/1998 | Mastri et al. |
| 5,769,303 | A | 6/1998 | Knodel et al. |
| 5,769,892 | A | 6/1998 | Kingwell |
| 5,772,099 | A | 6/1998 | Gravener |
| 5,772,673 | A | 6/1998 | Cuny et al. |
| 5,779,130 | A | 7/1998 | Alesi et al. |
| 5,779,131 | A | 7/1998 | Knodel et al. |
| 5,779,132 | A | 7/1998 | Knodel et al. |
| 5,782,396 | A | 7/1998 | Mastri et al. |
| 5,782,397 | A | 7/1998 | Koukline |
| 5,782,834 | A | 7/1998 | Lucey et al. |
| 5,785,232 | A | 7/1998 | Vidal et al. |
| 5,797,536 | A | 8/1998 | Smith et al. |
| 5,797,537 | A | 8/1998 | Oberlin et al. |
| 5,797,538 | A | 8/1998 | Heaton et al. |
| 5,810,811 | A | 9/1998 | Yates et al. |
| 5,810,855 | A | 9/1998 | Rayburn et al. |
| 5,814,055 | A | 9/1998 | Knodel et al. |
| 5,814,057 | A | 9/1998 | Oi et al. |
| 5,816,471 | A | 10/1998 | Plyley et al. |
| 5,817,109 | A | 10/1998 | McGarry et al. |
| 5,820,009 | A | 10/1998 | Melling et al. |
| 5,823,066 | A | 10/1998 | Huitema et al. |
| 5,826,776 | A | 10/1998 | Schulze et al. |
| 5,829,662 | A | 11/1998 | Allen et al. |
| 5,833,695 | A | 11/1998 | Yoon |
| 5,836,147 | A | 11/1998 | Schnipke |
| 5,862,972 | A | 1/1999 | Green et al. |
| 5,865,361 | A | 2/1999 | Milliman et al. |
| 5,871,135 | A | 2/1999 | Williamson, IV et al. |
| 5,873,873 | A | 2/1999 | Smith et al. |
| 5,878,938 | A | 3/1999 | Bittner et al. |
| 5,893,506 | A * | 4/1999 | Powell ............. 227/175.3 |
| 5,894,979 | A | 4/1999 | Powell |
| 5,897,562 | A | 4/1999 | Bolanos et al. |
| 5,901,895 | A | 5/1999 | Heaton et al. |
| 5,911,352 | A | 6/1999 | Racenet et al. |
| 5,911,353 | A | 6/1999 | Bolanos et al. |
| 5,918,791 | A | 7/1999 | Sorrentino et al. |
| 5,919,198 | A | 7/1999 | Graves, Jr. et al. |
| 5,922,001 | A | 7/1999 | Yoon |
| 5,931,847 | A | 8/1999 | Bittner et al. |
| 5,941,442 | A * | 8/1999 | Geiste et al. ............. 227/175.1 |
| 5,954,259 | A | 9/1999 | Viola et al. |
| 5,964,774 | A | 10/1999 | McKean et al. |
| 5,980,510 | A | 11/1999 | Tsonton et al. |
| 5,988,479 | A * | 11/1999 | Palmer ............. 227/175.4 |
| 6,004,335 | A | 12/1999 | Vaitekunas et al. |
| 6,010,054 | A | 1/2000 | Johnson et al. |
| 6,032,849 | A | 3/2000 | Mastri et al. |
| 6,045,560 | A | 4/2000 | McKean et al. |
| 6,063,097 | A | 5/2000 | Oi et al. |
| 6,079,606 | A | 6/2000 | Milliman et al. |
| 6,099,551 | A | 8/2000 | Gabbay |
| 6,109,500 | A | 8/2000 | Alli et al. |
| 6,131,789 | A | 10/2000 | Schulze et al. |
| 6,131,790 | A | 10/2000 | Piraka |
| 6,155,473 | A | 12/2000 | Tompkins et al. |
| 6,197,017 | B1 | 3/2001 | Brock et al. |
| 6,202,914 | B1 | 3/2001 | Geiste et al. |
| 6,241,139 | B1 | 6/2001 | Milliman et al. |
| 6,250,532 | B1 | 6/2001 | Green et al. |
| 6,264,086 | B1 | 7/2001 | McGuckin, Jr. |
| 6,264,087 | B1 | 7/2001 | Whitman |
| 6,269,977 | B1 | 8/2001 | Moore |
| 6,279,809 | B1 | 8/2001 | Nicolo |
| 6,315,183 | B1 | 11/2001 | Piraka |
| 6,315,184 | B1 | 11/2001 | Whitman |
| 6,325,810 | B1 | 12/2001 | Hamilton et al. |
| 6,330,965 | B1 | 12/2001 | Milliman et al. |
| 6,391,038 | B2 | 5/2002 | Vargas et al. |
| 6,398,797 | B2 | 6/2002 | Bombard et al. |
| 6,436,097 | B1 | 8/2002 | Nardella |
| 6,439,446 | B1 | 8/2002 | Perry et al. |
| 6,443,973 | B1 | 9/2002 | Whitman |
| 6,463,623 | B2 | 10/2002 | Ahn et al. |

(56) References Cited

U.S. PATENT DOCUMENTS

| | | |
|---|---|---|
| 6,478,804 B2 | 11/2002 | Vargas et al. |
| 6,488,196 B1 | 12/2002 | Fenton, Jr. |
| 6,503,257 B2 | 1/2003 | Grant et al. |
| 6,505,768 B2 | 1/2003 | Whitman |
| 6,544,274 B2 | 4/2003 | Danitz et al. |
| 6,554,844 B2 | 4/2003 | Lee et al. |
| 6,565,554 B1 | 5/2003 | Niemeyer |
| 6,587,750 B2 | 7/2003 | Gerbi et al. |
| 6,592,597 B2 | 7/2003 | Grant et al. |
| 6,594,552 B1 | 7/2003 | Nowlin et al. |
| 6,602,252 B2 | 8/2003 | Mollenauer |
| 6,612,053 B2 | 9/2003 | Liao |
| 6,619,529 B2 | 9/2003 | Green et al. |
| D480,808 S | 10/2003 | Wells et al. |
| 6,644,532 B2 | 11/2003 | Green et al. |
| 6,656,193 B2 | 12/2003 | Grant et al. |
| 6,669,073 B2 | 12/2003 | Milliman et al. |
| 6,681,978 B2 | 1/2004 | Geiste et al. |
| 6,698,643 B2 | 3/2004 | Whitman |
| 6,716,232 B1 | 4/2004 | Vidal et al. |
| 6,722,552 B2 | 4/2004 | Fenton, Jr. |
| 6,731,473 B2 | 5/2004 | Li et al. |
| 6,755,338 B2 | 6/2004 | Hahnen et al. |
| 6,783,524 B2 | 8/2004 | Anderson et al. |
| 6,786,382 B1 | 9/2004 | Hoffman |
| 6,808,262 B2 | 10/2004 | Chapoy et al. |
| 6,817,509 B2 | 11/2004 | Geiste et al. |
| 6,830,174 B2 | 12/2004 | Hillstead et al. |
| 6,835,199 B2 | 12/2004 | McGuckin, Jr. et al. |
| 6,843,403 B2 | 1/2005 | Whitman |
| RE38,708 E | 3/2005 | Bolanos et al. |
| 6,877,647 B2 | 4/2005 | Green et al. |
| 6,879,880 B2 | 4/2005 | Nowlin et al. |
| 6,889,116 B2 | 5/2005 | Jinno |
| 6,905,057 B2 | 6/2005 | Swayze et al. |
| 6,945,444 B2 | 9/2005 | Gresham |
| 6,953,138 B1 | 10/2005 | Dworak et al. |
| 6,953,139 B2 | 10/2005 | Milliman et al. |
| 6,959,852 B2 | 11/2005 | Shelton, IV et al. |
| 6,962,594 B1 | 11/2005 | Thevenet |
| 6,964,363 B2 | 11/2005 | Wales et al. |
| 6,978,921 B2 | 12/2005 | Shelton, IV et al. |
| 6,981,628 B2 | 1/2006 | Wales |
| 6,986,451 B1 | 1/2006 | Mastri et al. |
| 6,988,649 B2 | 1/2006 | Shelton, IV et al. |
| 6,991,627 B2 | 1/2006 | Madhani et al. |
| 6,994,714 B2 | 2/2006 | Vargas et al. |
| 7,000,818 B2 | 2/2006 | Shelton, IV et al. |
| 7,000,819 B2 | 2/2006 | Swayze et al. |
| 7,032,799 B2 | 4/2006 | Viola et al. |
| 7,044,352 B2 | 5/2006 | Shelton, IV et al. |
| 7,044,353 B2 | 5/2006 | Mastri et al. |
| 7,055,730 B2 | 6/2006 | Ehrenfels et al. |
| 7,055,731 B2 | 6/2006 | Shelton, IV et al. |
| 7,059,508 B2 | 6/2006 | Shelton, IV et al. |
| 7,070,083 B2 | 7/2006 | Jankowski |
| 7,083,075 B2 | 8/2006 | Swayze et al. |
| 7,097,089 B2 | 8/2006 | Marczyk |
| 7,111,769 B2 | 9/2006 | Wales et al. |
| 7,114,642 B2 | 10/2006 | Whitman |
| 7,121,446 B2 | 10/2006 | Arad et al. |
| 7,128,253 B2 | 10/2006 | Mastri et al. |
| 7,128,254 B2 | 10/2006 | Shelton, IV et al. |
| 7,140,527 B2 | 11/2006 | Ehrenfels et al. |
| 7,140,528 B2 | 11/2006 | Shelton, IV |
| 7,143,923 B2 | 12/2006 | Shelton, IV et al. |
| 7,143,924 B2 | 12/2006 | Scirica et al. |
| 7,143,925 B2 | 12/2006 | Shelton, IV et al. |
| 7,143,926 B2 | 12/2006 | Shelton, IV et al. |
| 7,147,138 B2 | 12/2006 | Shelton, IV |
| 7,159,750 B2 | 1/2007 | Racenet et al. |
| 7,168,604 B2 | 1/2007 | Milliman |
| 7,172,104 B2 | 2/2007 | Scirica et al. |
| 7,188,758 B2 | 3/2007 | Viola et al. |
| 7,207,471 B2 | 4/2007 | Heinrich et al. |
| 7,213,736 B2 | 5/2007 | Wales et al. |
| 7,225,963 B2 | 6/2007 | Scirica |
| 7,225,964 B2 | 6/2007 | Mastri et al. |
| 7,238,195 B2 | 7/2007 | Viola |
| 7,246,734 B2 | 7/2007 | Shelton, IV |
| 7,258,262 B2 | 8/2007 | Mastri et al. |
| 7,278,562 B2 | 10/2007 | Mastri et al. |
| 7,278,563 B1 | 10/2007 | Green |
| 7,287,682 B1 | 10/2007 | Ezzat et al. |
| 7,293,685 B2 | 11/2007 | Ehrenfels et al. |
| 7,296,722 B2 | 11/2007 | Ivanko |
| 7,296,724 B2 | 11/2007 | Green et al. |
| 7,296,772 B2 | 11/2007 | Wang |
| 7,300,444 B1 | 11/2007 | Nielson et al. |
| 7,303,107 B2 | 12/2007 | Milliman et al. |
| 7,303,108 B2 | 12/2007 | Shelton, IV |
| 7,308,998 B2 | 12/2007 | Mastri et al. |
| 7,326,232 B2 | 2/2008 | Viola et al. |
| 7,328,828 B2 | 2/2008 | Ortiz et al. |
| 7,328,829 B2 | 2/2008 | Arad et al. |
| 7,334,717 B2 | 2/2008 | Rethy et al. |
| 7,354,447 B2 | 4/2008 | Shelton, IV et al. |
| 7,357,287 B2 | 4/2008 | Shelton, IV et al. |
| 7,364,061 B2 | 4/2008 | Swayze et al. |
| 7,367,485 B2 | 5/2008 | Shelton, IV et al. |
| 7,377,928 B2 | 5/2008 | Zubik et al. |
| 7,380,695 B2 | 6/2008 | Doll et al. |
| 7,380,696 B2 | 6/2008 | Shelton, IV et al. |
| 7,396,356 B2 | 7/2008 | Mollenauer |
| 7,398,907 B2 | 7/2008 | Racenet et al. |
| 7,399,310 B2 | 7/2008 | Edoga et al. |
| 7,401,720 B1 | 7/2008 | Durrani |
| 7,401,721 B2 | 7/2008 | Holsten et al. |
| 7,404,508 B2 | 7/2008 | Smith et al. |
| 7,404,509 B2 | 7/2008 | Ortiz et al. |
| 7,407,074 B2 | 8/2008 | Ortiz et al. |
| 7,407,075 B2 | 8/2008 | Holsten et al. |
| 7,407,077 B2 | 8/2008 | Ortiz et al. |
| 7,407,078 B2 | 8/2008 | Shelton, IV et al. |
| 7,416,101 B2 | 8/2008 | Shelton, IV et al. |
| 7,419,080 B2 | 9/2008 | Smith et al. |
| 7,419,081 B2 | 9/2008 | Ehrenfels et al. |
| 7,419,495 B2 | 9/2008 | Menn et al. |
| 7,422,139 B2 | 9/2008 | Shelton, IV et al. |
| 7,424,965 B2 | 9/2008 | Racenet et al. |
| 7,431,189 B2 | 10/2008 | Shelton, IV et al. |
| 7,431,730 B2 | 10/2008 | Viola |
| 7,434,715 B2 | 10/2008 | Shelton, IV et al. |
| 7,434,717 B2 | 10/2008 | Shelton, IV et al. |
| 7,438,208 B2 | 10/2008 | Larson |
| 7,438,209 B1 | 10/2008 | Hess et al. |
| 7,441,684 B2 | 10/2008 | Shelton, IV et al. |
| 7,441,685 B1 | 10/2008 | Boudreaux |
| 7,448,525 B2 | 11/2008 | Shelton, IV et al. |
| 7,451,904 B2 | 11/2008 | Shelton, IV |
| 7,455,208 B2 | 11/2008 | Wales et al. |
| 7,455,676 B2 | 11/2008 | Holsten et al. |
| 7,458,494 B2 | 12/2008 | Matsutani et al. |
| 7,461,767 B2 | 12/2008 | Viola et al. |
| 7,462,185 B1 | 12/2008 | Knodel |
| 7,464,846 B2 | 12/2008 | Shelton, IV et al. |
| 7,464,847 B2 | 12/2008 | Viola et al. |
| 7,464,848 B2 | 12/2008 | Green et al. |
| 7,464,849 B2 | 12/2008 | Shelton, IV et al. |
| 7,467,740 B2 | 12/2008 | Shelton, IV et al. |
| 7,472,814 B2 | 1/2009 | Mastri et al. |
| 7,472,815 B2 | 1/2009 | Shelton, IV et al. |
| 7,472,816 B2 | 1/2009 | Holsten et al. |
| 7,473,258 B2 | 1/2009 | Clauson et al. |
| 7,481,347 B2 | 1/2009 | Roy |
| 7,481,348 B2 | 1/2009 | Marczyk |
| 7,481,349 B2 | 1/2009 | Holsten et al. |
| 7,481,824 B2 | 1/2009 | Gillum et al. |
| 7,487,899 B2 | 2/2009 | Shelton, IV et al. |
| 7,490,749 B2 | 2/2009 | Schall et al. |
| 7,494,039 B2 | 2/2009 | Racenet et al. |
| 7,500,979 B2 | 3/2009 | Hueil et al. |
| 7,503,474 B2 | 3/2009 | Hillstead et al. |
| 7,506,790 B2 | 3/2009 | Shelton, IV |

(56) References Cited

U.S. PATENT DOCUMENTS

| | | |
|---|---|---|
| 7,506,791 B2 | 3/2009 | Omaits et al. |
| 7,510,107 B2 | 3/2009 | Timm et al. |
| 7,513,408 B2 | 4/2009 | Shelton, IV et al. |
| 7,517,356 B2 | 4/2009 | Heinrich |
| 7,537,602 B2 | 5/2009 | Whitman |
| 7,543,729 B2 | 6/2009 | Ivanko |
| 7,543,730 B1 | 6/2009 | Marczyk |
| 7,543,731 B2 | 6/2009 | Green et al. |
| 7,552,854 B2 | 6/2009 | Wixey et al. |
| 7,556,185 B2 | 7/2009 | Viola |
| 7,556,186 B2 | 7/2009 | Milliman |
| 7,559,450 B2 | 7/2009 | Wales et al. |
| 7,559,452 B2 | 7/2009 | Wales et al. |
| 7,559,453 B2 | 7/2009 | Heinrich et al. |
| 7,559,937 B2 | 7/2009 | de la Torre et al. |
| 7,565,993 B2 | 7/2009 | Milliman et al. |
| 7,568,603 B2 | 8/2009 | Shelton, IV et al. |
| 7,568,604 B2 | 8/2009 | Ehrenfels et al. |
| 7,571,845 B2 | 8/2009 | Viola |
| 7,575,144 B2 | 8/2009 | Ortiz et al. |
| 7,584,880 B2 | 9/2009 | Racenet et al. |
| 7,588,174 B2 | 9/2009 | Holsten et al. |
| 7,588,175 B2 | 9/2009 | Timm et al. |
| 7,588,176 B2 | 9/2009 | Timm et al. |
| 7,588,177 B2 | 9/2009 | Racenet |
| 7,597,229 B2 | 10/2009 | Boudreaux et al. |
| 7,597,230 B2 | 10/2009 | Racenet et al. |
| 7,600,663 B2 | 10/2009 | Green |
| 7,604,150 B2 | 10/2009 | Boudreaux |
| 7,604,151 B2 | 10/2009 | Hess et al. |
| 7,607,557 B2 | 10/2009 | Shelton, IV et al. |
| 7,611,038 B2 | 11/2009 | Racenet et al. |
| 7,617,961 B2 | 11/2009 | Viola |
| 7,624,902 B2 | 12/2009 | Marczyk et al. |
| 7,624,903 B2 | 12/2009 | Green et al. |
| 7,631,793 B2 | 12/2009 | Rethy et al. |
| 7,631,794 B2 | 12/2009 | Rethy et al. |
| 7,635,073 B2 | 12/2009 | Heinrich |
| 7,635,074 B2 | 12/2009 | Olson et al. |
| 7,635,373 B2 | 12/2009 | Ortiz |
| 7,637,409 B2 | 12/2009 | Marczyk |
| 7,637,410 B2 | 12/2009 | Marczyk |
| 7,641,091 B2 | 1/2010 | Olson et al. |
| 7,641,093 B2 | 1/2010 | Doll et al. |
| 7,641,095 B2 | 1/2010 | Viola |
| 7,644,848 B2 | 1/2010 | Swayze et al. |
| 7,648,055 B2 | 1/2010 | Marczyk |
| 7,651,017 B2 | 1/2010 | Oritz et al. |
| 7,654,431 B2 | 2/2010 | Hueil et al. |
| 7,658,311 B2 | 2/2010 | Boudreaux |
| 7,658,312 B2 | 2/2010 | Vidal et al. |
| 7,665,646 B2 | 2/2010 | Prommersberger |
| 7,665,647 B2 | 2/2010 | Shelton, IV et al. |
| 7,669,746 B2 | 3/2010 | Shelton, IV |
| 7,670,334 B2 | 3/2010 | Hueil et al. |
| 7,673,780 B2 | 3/2010 | Shelton, IV et al. |
| 7,673,781 B2 | 3/2010 | Swayze et al. |
| 7,673,782 B2 | 3/2010 | Hess et al. |
| 7,673,783 B2 | 3/2010 | Morgan et al. |
| 7,678,121 B1 | 3/2010 | Knodel |
| 7,681,772 B2 | 3/2010 | Green et al. |
| 7,682,367 B2 | 3/2010 | Shah et al. |
| 7,682,368 B1 | 3/2010 | Bombard et al. |
| 7,690,547 B2 | 4/2010 | Racenet et al. |
| 7,694,865 B2 | 4/2010 | Scirica |
| 7,699,205 B2 | 4/2010 | Ivanko |
| 7,703,653 B2 | 4/2010 | Shah et al. |
| 7,721,930 B2 | 5/2010 | McKenna et al. |
| 7,721,931 B2 | 5/2010 | Shelton et al. |
| 7,721,933 B2 | 5/2010 | Ehrenfels et al. |
| 7,721,935 B2 | 5/2010 | Racenet et al. |
| 7,726,537 B2 | 6/2010 | Olson et al. |
| 7,726,538 B2 | 6/2010 | Holsten et al. |
| 7,726,539 B2 | 6/2010 | Holsten et al. |
| 7,731,072 B2 | 6/2010 | Timm et al. |
| 7,735,703 B2 | 6/2010 | Morgan et al. |
| 7,740,159 B2 | 6/2010 | Shelton et al. |
| 7,740,160 B2 | 6/2010 | Viola |
| 7,743,960 B2 | 6/2010 | Whitman |
| 7,744,628 B2 | 6/2010 | Viola |
| 7,753,245 B2 | 7/2010 | Boudreaux et al. |
| 7,753,248 B2 | 7/2010 | Viola |
| 7,757,924 B2 | 7/2010 | Gerbi et al. |
| 7,757,925 B2 | 7/2010 | Viola et al. |
| 7,762,445 B2 | 7/2010 | Heinrich et al. |
| 7,766,209 B2 | 8/2010 | Baxter, III et al. |
| 7,766,210 B2 | 8/2010 | Shelton, IV et al. |
| 7,766,924 B1 | 8/2010 | Bombard et al. |
| 7,766,928 B2 | 8/2010 | Ezzat et al. |
| 7,770,774 B2 | 8/2010 | Mastri et al. |
| 7,770,775 B2 | 8/2010 | Shelton, IV et al. |
| 7,776,060 B2 | 8/2010 | Mooradian et al. |
| 7,780,055 B2 | 8/2010 | Scirica et al. |
| 7,784,662 B2 | 8/2010 | Wales et al. |
| 7,789,283 B2 | 9/2010 | Shah |
| 7,789,889 B2 | 9/2010 | Zubik et al. |
| 7,793,812 B2 | 9/2010 | Moore et al. |
| 7,793,814 B2 | 9/2010 | Racenet et al. |
| 7,794,475 B2 | 9/2010 | Hess et al. |
| 7,798,385 B2 | 9/2010 | Boyden et al. |
| 7,798,386 B2 | 9/2010 | Schall et al. |
| 7,799,039 B2 | 9/2010 | Shelton, IV et al. |
| 7,810,690 B2 | 10/2010 | Bilotti et al. |
| 7,810,691 B2 | 10/2010 | Boyden et al. |
| 7,810,692 B2 | 10/2010 | Hall et al. |
| 7,810,693 B2 | 10/2010 | Broehl et al. |
| 7,815,090 B2 | 10/2010 | Marczyk |
| 7,815,091 B2 | 10/2010 | Marczyk |
| 7,815,092 B2 | 10/2010 | Whitman et al. |
| 7,819,296 B2 | 10/2010 | Hueil et al. |
| 7,819,297 B2 | 10/2010 | Doll et al. |
| 7,819,298 B2 | 10/2010 | Hall et al. |
| 7,819,299 B2 | 10/2010 | Shelton, IV et al. |
| 7,819,896 B2 | 10/2010 | Racenet |
| 7,823,760 B2 * | 11/2010 | Zemlok et al. ............ 227/175.1 |
| 7,823,761 B2 | 11/2010 | Boyden et al. |
| 7,824,426 B2 | 11/2010 | Racenet et al. |
| 7,828,186 B2 | 11/2010 | Wales |
| 7,828,187 B2 | 11/2010 | Green et al. |
| 7,828,188 B2 | 11/2010 | Jankowski |
| 7,828,189 B2 | 11/2010 | Holsten et al. |
| 7,832,408 B2 | 11/2010 | Shelton, IV et al. |
| 7,832,611 B2 | 11/2010 | Boyden et al. |
| 7,832,612 B2 * | 11/2010 | Baxter et al. ............ 227/175.2 |
| 7,837,079 B2 | 11/2010 | Holsten et al. |
| 7,837,081 B2 | 11/2010 | Holsten et al. |
| 7,841,503 B2 | 11/2010 | Sonnenschein et al. |
| 7,845,533 B2 | 12/2010 | Marczyk et al. |
| 7,845,534 B2 | 12/2010 | Viola et al. |
| 7,845,535 B2 | 12/2010 | Scircia |
| 7,845,537 B2 | 12/2010 | Shelton, IV et al. |
| 7,845,538 B2 | 12/2010 | Whitman |
| 7,850,703 B2 | 12/2010 | Bombard et al. |
| 7,857,183 B2 | 12/2010 | Shelton, IV |
| 7,857,184 B2 | 12/2010 | Viola |
| 7,857,185 B2 | 12/2010 | Swayze et al. |
| 7,857,186 B2 | 12/2010 | Baxter, III et al. |
| 7,861,906 B2 | 1/2011 | Doll et al. |
| 7,861,907 B2 | 1/2011 | Green et al. |
| 7,866,524 B2 | 1/2011 | Krehel |
| 7,866,525 B2 | 1/2011 | Scirica |
| 7,866,526 B2 | 1/2011 | Green et al. |
| 7,866,527 B2 | 1/2011 | Hall et al. |
| 7,866,528 B2 | 1/2011 | Olson et al. |
| 7,870,989 B2 | 1/2011 | Viola et al. |
| 7,886,952 B2 | 2/2011 | Scirica et al. |
| 7,891,532 B2 | 2/2011 | Mastri et al. |
| 7,891,533 B2 | 2/2011 | Green et al. |
| 7,891,534 B2 | 2/2011 | Wenchell et al. |
| 7,896,214 B2 | 3/2011 | Farascioni |
| 7,900,805 B2 | 3/2011 | Shelton, IV et al. |
| 7,901,416 B2 | 3/2011 | Nolan et al. |
| 7,905,380 B2 | 3/2011 | Shelton, IV et al. |
| 7,905,381 B2 | 3/2011 | Baxter, III et al. |

(56) References Cited

U.S. PATENT DOCUMENTS

| | | | |
|---|---|---|---|
| 7,909,039 B2 | 3/2011 | Hur |
| 7,909,220 B2 | 3/2011 | Viola |
| 7,909,221 B2 | 3/2011 | Viola et al. |
| 7,909,224 B2 | 3/2011 | Prommersberger |
| 7,913,891 B2 | 3/2011 | Doll et al. |
| 7,913,893 B2 | 3/2011 | Mastri et al. |
| 7,914,543 B2 | 3/2011 | Roth et al. |
| 7,918,230 B2 | 4/2011 | Whitman et al. |
| 7,918,276 B2 | 4/2011 | Guignard et al. |
| 7,922,061 B2 | 4/2011 | Shelton, IV et al. |
| 7,922,063 B2 | 4/2011 | Zemlok et al. |
| 7,922,064 B2 | 4/2011 | Boyden et al. |
| 7,926,691 B2 | 4/2011 | Viola et al. |
| 7,926,692 B2 | 4/2011 | Racenet et al. |
| 7,934,628 B2 | 5/2011 | Wenchell et al. |
| 7,934,630 B2 | 5/2011 | Shelton, IV et al. |
| 7,934,631 B2 | 5/2011 | Balbierz et al. |
| 7,942,300 B2 | 5/2011 | Rethy et al. |
| 7,942,303 B2 | 5/2011 | Shah |
| 7,950,560 B2 | 5/2011 | Zemlok et al. |
| 7,950,561 B2 | 5/2011 | Aranyi |
| 7,950,562 B2 | 5/2011 | Beardsley et al. |
| 7,954,682 B2 | 6/2011 | Giordano et al. |
| 7,954,683 B1 | 6/2011 | Knodel et al. |
| 7,954,684 B2 | 6/2011 | Boudreaux |
| 7,954,685 B2 | 6/2011 | Viola |
| 7,954,686 B2 | 6/2011 | Baxter, III et al. |
| 7,954,687 B2 | 6/2011 | Zemlok et al. |
| 7,959,051 B2 | 6/2011 | Smith et al. |
| 7,963,431 B2 | 6/2011 | Scirica |
| 7,963,432 B2 | 6/2011 | Knodel et al. |
| 7,963,433 B2 | 6/2011 | Whitman et al. |
| 7,967,178 B2 | 6/2011 | Scirica et al. |
| 7,967,179 B2 | 6/2011 | Olson et al. |
| 7,967,180 B2 | 6/2011 | Scirica et al. |
| 7,975,894 B2 | 7/2011 | Boyden et al. |
| 7,980,443 B2 | 7/2011 | Scheib et al. |
| 7,988,026 B2 | 8/2011 | Knodel et al. |
| 7,988,027 B2 | 8/2011 | Olson et al. |
| 7,988,028 B2 | 8/2011 | Farascioni et al. |
| 7,992,758 B2 | 8/2011 | Whitman et al. |
| 7,997,468 B2 | 8/2011 | Farascioni |
| 7,997,469 B2 | 8/2011 | Olson et al. |
| 8,002,795 B2 | 8/2011 | Beetel |
| 8,006,885 B2 | 8/2011 | Marczyk |
| 8,006,887 B2 | 8/2011 | Marczyk |
| 8,007,505 B2 | 8/2011 | Weller et al. |
| 8,007,513 B2 | 8/2011 | Nalagatla et al. |
| 8,011,550 B2 | 9/2011 | Aranyi et al. |
| 8,011,551 B2 | 9/2011 | Marczyk et al. |
| 8,011,552 B2 | 9/2011 | Ivanko |
| 8,011,553 B2 | 9/2011 | Mastri et al. |
| 8,011,555 B2 | 9/2011 | Tarinelli et al. |
| 8,012,170 B2 | 9/2011 | Whitman et al. |
| 8,015,976 B2 | 9/2011 | Shah |
| 8,016,177 B2 | 9/2011 | Bettuchi et al. |
| 8,016,178 B2 | 9/2011 | Olson et al. |
| 8,020,742 B2 | 9/2011 | Marczyk |
| 8,020,743 B2 | 9/2011 | Shelton, IV |
| 8,028,882 B2 | 10/2011 | Viola |
| 8,028,883 B2 | 10/2011 | Stopek |
| 8,028,884 B2 | 10/2011 | Sniffen et al. |
| 8,033,438 B2 | 10/2011 | Scirica |
| 8,033,440 B2 | 10/2011 | Wenchell et al. |
| 8,033,441 B2 | 10/2011 | Marczyk |
| 8,033,442 B2 | 10/2011 | Racenet et al. |
| 8,034,077 B2 | 10/2011 | Smith et al. |
| 8,038,044 B2 | 10/2011 | Viola |
| 8,038,045 B2 | 10/2011 | Bettuchi et al. |
| 8,052,024 B2 | 11/2011 | Viola et al. |
| 8,056,787 B2 | 11/2011 | Boudreaux et al. |
| 8,056,788 B2 | 11/2011 | Mastri et al. |
| 8,056,791 B2 | 11/2011 | Whitman |
| 8,061,577 B2 | 11/2011 | Racenet et al. |
| 8,066,166 B2 | 11/2011 | Demmy et al. |
| 8,070,033 B2 | 12/2011 | Milliman et al. |
| 8,070,035 B2 | 12/2011 | Holsten et al. |
| 8,074,858 B2 | 12/2011 | Marczyk et al. |
| 8,074,859 B2 | 12/2011 | Kostrzewski |
| 8,074,862 B2 | 12/2011 | Shah |
| 8,083,118 B2 | 12/2011 | Milliman et al. |
| 8,083,119 B2 | 12/2011 | Prommersberger |
| 8,083,120 B2 | 12/2011 | Shelton et al. |
| 8,087,563 B2 | 1/2012 | Milliman et al. |
| 8,091,753 B2 | 1/2012 | Viola |
| 8,091,754 B2 | 1/2012 | Ehrenfels et al. |
| 8,091,756 B2 | 1/2012 | Viola |
| 8,096,459 B2 | 1/2012 | Ortiz et al. |
| 8,096,460 B2 | 1/2012 | Blier et al. |
| 8,100,309 B2 | 1/2012 | Marczyk |
| 8,100,310 B2 | 1/2012 | Zemlok |
| 8,113,406 B2 | 2/2012 | Holsten et al. |
| 8,113,407 B2 | 2/2012 | Holsten et al. |
| 8,113,408 B2 | 2/2012 | Wenchell et al. |
| 8,113,409 B2 | 2/2012 | Cohen et al. |
| 8,113,410 B2 | 2/2012 | Hall et al. |
| 8,123,101 B2 | 2/2012 | Racenet et al. |
| 8,127,975 B2 | 3/2012 | Olson et al. |
| 8,127,976 B2 | 3/2012 | Scirica et al. |
| 8,132,703 B2 | 3/2012 | Milliman et al. |
| 8,132,705 B2 | 3/2012 | Viola et al. |
| 8,132,706 B2 | 3/2012 | Marczyk et al. |
| 8,136,713 B2 | 3/2012 | Hathaway et al. |
| 8,141,762 B2 | 3/2012 | Bedi et al. |
| 8,152,041 B2 | 4/2012 | Kostrzewski |
| 8,157,148 B2 | 4/2012 | Scirica |
| 8,157,151 B2 | 4/2012 | Ingmanson et al. |
| 8,167,185 B2 | 5/2012 | Shelton, IV et al. |
| 8,167,186 B2 | 5/2012 | Racenet et al. |
| 8,172,121 B2 | 5/2012 | Krehel |
| 8,172,124 B2 | 5/2012 | Shelton, IV et al. |
| 8,181,837 B2 | 5/2012 | Roy |
| 8,186,555 B2 | 5/2012 | Shelton, IV et al. |
| 8,186,558 B2 | 5/2012 | Sapienza |
| 8,186,560 B2 | 5/2012 | Hess et al. |
| 8,196,795 B2 | 6/2012 | Moore et al. |
| 8,196,796 B2 | 6/2012 | Shelton, IV et al. |
| 8,205,619 B2 | 6/2012 | Shah et al. |
| 8,205,780 B2 | 6/2012 | Sorrentino et al. |
| 8,205,781 B2 | 6/2012 | Baxter, III et al. |
| 8,216,236 B2 | 7/2012 | Heinrich et al. |
| 8,220,688 B2 | 7/2012 | Laurent et al. |
| 8,220,690 B2 | 7/2012 | Hess et al. |
| 8,225,979 B2 | 7/2012 | Farascioni et al. |
| 8,231,040 B2 | 7/2012 | Zemlok et al. |
| 8,231,041 B2 | 7/2012 | Marczyk et al. |
| 8,235,272 B2 | 8/2012 | Nicholas et al. |
| 8,236,010 B2 | 8/2012 | Ortiz et al. |
| 8,241,322 B2 | 8/2012 | Whitman et al. |
| 8,245,897 B2 | 8/2012 | Tzakis et al. |
| 8,245,898 B2 | 8/2012 | Smith et al. |
| 8,245,899 B2 | 8/2012 | Swensgard et al. |
| 8,252,009 B2 | 8/2012 | Weller et al. |
| 8,267,300 B2 | 9/2012 | Boudreaux |
| 8,272,554 B2 | 9/2012 | Whitman et al. |
| 2004/0108357 A1 | 6/2004 | Milliman |
| 2004/0199180 A1 | 10/2004 | Knodel et al. |
| 2004/0199181 A1 | 10/2004 | Knodel et al. |
| 2004/0232201 A1 | 11/2004 | Wenchell |
| 2004/0243151 A1 | 12/2004 | Demmy |
| 2004/0267310 A1 | 12/2004 | Racenet |
| 2005/0023324 A1* | 2/2005 | Doll et al. .................. 227/175.2 |
| 2005/0103819 A1 | 5/2005 | Racenet |
| 2005/0119669 A1 | 6/2005 | Demmy |
| 2005/0189397 A1 | 9/2005 | Jankowski |
| 2005/0216055 A1 | 9/2005 | Scirica et al. |
| 2005/0222616 A1* | 10/2005 | Rethy et al. .................. 606/215 |
| 2005/0230453 A1* | 10/2005 | Viola .......................... 227/176.1 |
| 2005/0263562 A1 | 12/2005 | Shelton, IV et al. |
| 2006/0049229 A1 | 3/2006 | Milliman et al. |
| 2006/0180634 A1 | 8/2006 | Shelton, IV et al. |
| 2006/0219752 A1* | 10/2006 | Arad et al. .................. 227/176.1 |
| 2006/0289602 A1 | 12/2006 | Wales et al. |
| 2007/0027469 A1 | 2/2007 | Smith et al. |

(56) References Cited

U.S. PATENT DOCUMENTS

| | | |
|---|---|---|
| 2007/0073341 A1 | 3/2007 | Smith et al. |
| 2007/0084897 A1 | 4/2007 | Shelton, IV et al. |
| 2007/0084899 A1 | 4/2007 | Taylor |
| 2007/0102472 A1 | 5/2007 | Shelton, IV |
| 2007/0106317 A1 | 5/2007 | Shelton, IV |
| 2007/0119901 A1 | 5/2007 | Ehrenfels et al. |
| 2007/0145096 A1 | 6/2007 | Viola et al. |
| 2007/0170225 A1 | 7/2007 | Shelton, IV et al. |
| 2007/0175949 A1 | 8/2007 | Shelton, IV et al. |
| 2007/0175950 A1 | 8/2007 | Shelton, IV et al. |
| 2007/0175951 A1 | 8/2007 | Shelton, IV et al. |
| 2007/0175955 A1 | 8/2007 | Shelton, IV et al. |
| 2007/0179528 A1 | 8/2007 | Soltz et al. |
| 2007/0194079 A1 | 8/2007 | Hueil et al. |
| 2007/0194081 A1 | 8/2007 | Hueil et al. |
| 2007/0194082 A1 | 8/2007 | Morgan et al. |
| 2007/0221700 A1 | 9/2007 | Ortiz et al. |
| 2007/0295780 A1 | 12/2007 | Shelton et al. |
| 2008/0029570 A1 | 2/2008 | Shelton et al. |
| 2008/0029573 A1 | 2/2008 | Shelton et al. |
| 2008/0029574 A1 | 2/2008 | Shelton et al. |
| 2008/0078800 A1 | 4/2008 | Hess et al. |
| 2008/0078802 A1 | 4/2008 | Hess et al. |
| 2008/0078803 A1 | 4/2008 | Shelton et al. |
| 2008/0078804 A1 | 4/2008 | Shelton et al. |
| 2008/0078806 A1 | 4/2008 | Omaits et al. |
| 2008/0078808 A1 | 4/2008 | Hess et al. |
| 2008/0110961 A1 | 5/2008 | Voegele et al. |
| 2008/0149685 A1 | 6/2008 | Smith et al. |
| 2008/0169328 A1 | 7/2008 | Shelton |
| 2008/0169329 A1 | 7/2008 | Shelton et al. |
| 2008/0169330 A1 | 7/2008 | Shelton et al. |
| 2008/0169331 A1 | 7/2008 | Shelton et al. |
| 2008/0169332 A1 | 7/2008 | Shelton et al. |
| 2008/0169333 A1 | 7/2008 | Shelton et al. |
| 2008/0287987 A1 | 11/2008 | Boyden et al. |
| 2008/0296344 A1 | 12/2008 | Cropper et al. |
| 2008/0296346 A1 | 12/2008 | Shelton, IV et al. |
| 2008/0302854 A1 | 12/2008 | Rethy et al. |
| 2008/0308602 A1 | 12/2008 | Timm et al. |
| 2008/0308603 A1 | 12/2008 | Shelton, IV et al. |
| 2009/0001121 A1 | 1/2009 | Hess et al. |
| 2009/0001124 A1 | 1/2009 | Hess et al. |
| 2009/0001130 A1 | 1/2009 | Hess et al. |
| 2009/0005808 A1 | 1/2009 | Hess et al. |
| 2009/0065549 A1 | 3/2009 | Viola |
| 2009/0078739 A1 | 3/2009 | Viola |
| 2009/0090763 A1 | 4/2009 | Zemlok et al. |
| 2009/0090766 A1 | 4/2009 | Knodel |
| 2009/0209946 A1 | 8/2009 | Swayze et al. |
| 2009/0209990 A1 | 8/2009 | Yates et al. |
| 2009/0236395 A1 | 9/2009 | Scirica |
| 2009/0242610 A1 | 10/2009 | Shelton, IV et al. |
| 2009/0255974 A1 | 10/2009 | Viola |
| 2009/0272787 A1 | 11/2009 | Scirica |
| 2009/0277946 A1 | 11/2009 | Marczyk |
| 2009/0277949 A1 | 11/2009 | Viola et al. |
| 2009/0283568 A1 | 11/2009 | Racenet et al. |
| 2009/0306708 A1 | 12/2009 | Shah |
| 2009/0308907 A1 | 12/2009 | Nalagatla et al. |
| 2009/0308909 A1* | 12/2009 | Nalagatla et al. ......... 227/180.1 |
| 2010/0012703 A1 | 1/2010 | Calabrese et al. |
| 2010/0012704 A1 | 1/2010 | Racenet et al. |
| 2010/0065604 A1* | 3/2010 | Weng .......................... 227/175.2 |
| 2010/0069942 A1 | 3/2010 | Shelton, IV et al. |
| 2010/0072254 A1 | 3/2010 | Aranyi et al. |
| 2010/0076429 A1 | 3/2010 | Heinrich |
| 2010/0076459 A1 | 3/2010 | Farascioni |
| 2010/0089970 A1 | 4/2010 | Smith |
| 2010/0127041 A1 | 5/2010 | Morgan et al. |
| 2010/0127042 A1 | 5/2010 | Shelton, IV |
| 2010/0133317 A1 | 6/2010 | Shelton, IV et al. |
| 2010/0133318 A1 | 6/2010 | Boudreaux |
| 2010/0147921 A1 | 6/2010 | Olson |
| 2010/0147922 A1 | 6/2010 | Olson |
| 2010/0155453 A1 | 6/2010 | Bombard et al. |
| 2010/0170931 A1 | 7/2010 | Viola |
| 2010/0193566 A1 | 8/2010 | Scheib et al. |
| 2010/0213241 A1 | 8/2010 | Bedi |
| 2010/0224668 A1 | 9/2010 | Fontayne et al. |
| 2010/0230468 A1 | 9/2010 | Viola |
| 2010/0237130 A1 | 9/2010 | Scirica |
| 2010/0243709 A1 | 9/2010 | Hess et al. |
| 2010/0249802 A1 | 9/2010 | May et al. |
| 2010/0252611 A1 | 10/2010 | Ezzat et al. |
| 2010/0252612 A1 | 10/2010 | Viola |
| 2010/0264192 A1 | 10/2010 | Marczyk |
| 2010/0264193 A1 | 10/2010 | Huang et al. |
| 2010/0264194 A1 | 10/2010 | Huang et al. |
| 2010/0294828 A1 | 11/2010 | Bindra et al. |
| 2010/0294829 A1 | 11/2010 | Giordano et al. |
| 2010/0301095 A1 | 12/2010 | Shelton, IV et al. |
| 2010/0305552 A1 | 12/2010 | Shelton, IV et al. |
| 2010/0308100 A1 | 12/2010 | Boudreaux |
| 2010/0320252 A1 | 12/2010 | Viola et al. |
| 2010/0320254 A1 | 12/2010 | Zemlok et al. |
| 2011/0006099 A1 | 1/2011 | Hall et al. |
| 2011/0006101 A1 | 1/2011 | Hall et al. |
| 2011/0006103 A1 | 1/2011 | Laurent et al. |
| 2011/0011914 A1 | 1/2011 | Baxter, III et al. |
| 2011/0011915 A1 | 1/2011 | Shelton, IV |
| 2011/0017801 A1 | 1/2011 | Zemlok et al. |
| 2011/0024477 A1 | 2/2011 | Hall |
| 2011/0024478 A1 | 2/2011 | Shelton, IV |
| 2011/0036887 A1 | 2/2011 | Zemlok et al. |
| 2011/0036888 A1 | 2/2011 | Pribanic et al. |
| 2011/0036890 A1 | 2/2011 | Ma |
| 2011/0036891 A1 | 2/2011 | Zemlok et al. |
| 2011/0036892 A1 | 2/2011 | Marczyk et al. |
| 2011/0036895 A1 | 2/2011 | Marczyk et al. |
| 2011/0042439 A1 | 2/2011 | Johnson et al. |
| 2011/0042441 A1 | 2/2011 | Shelton, IV et al. |
| 2011/0062213 A1 | 3/2011 | Scirica et al. |
| 2011/0068145 A1 | 3/2011 | Bedi et al. |
| 2011/0068148 A1 | 3/2011 | Hall et al. |
| 2011/0084114 A1 | 4/2011 | Marczyk et al. |
| 2011/0084115 A1 | 4/2011 | Bedi et al. |
| 2011/0087276 A1 | 4/2011 | Bedi et al. |
| 2011/0089221 A1 | 4/2011 | Masiakos et al. |
| 2011/0095067 A1 | 4/2011 | Ohdaira |
| 2011/0101067 A1 | 5/2011 | Johnson et al. |
| 2011/0101069 A1 | 5/2011 | Bombard et al. |
| 2011/0108603 A1 | 5/2011 | Racenet et al. |
| 2011/0114702 A1 | 5/2011 | Farascioni |
| 2011/0121049 A1 | 5/2011 | Malinouskas et al. |
| 2011/0132961 A1 | 6/2011 | Whitman et al. |
| 2011/0132963 A1 | 6/2011 | Giordano et al. |
| 2011/0132964 A1 | 6/2011 | Weisenburgh, II et al. |
| 2011/0132965 A1 | 6/2011 | Moore et al. |
| 2011/0139851 A1 | 6/2011 | McCuen |
| 2011/0144640 A1 | 6/2011 | Heinrich et al. |
| 2011/0147433 A1 | 6/2011 | Shelton, IV et al. |
| 2011/0147434 A1 | 6/2011 | Hueil et al. |
| 2011/0155781 A1 | 6/2011 | Swensgard et al. |
| 2011/0155784 A1 | 6/2011 | Shelton, IV et al. |
| 2011/0155786 A1 | 6/2011 | Shelton, IV |
| 2011/0155787 A1 | 6/2011 | Baxter, III et al. |
| 2011/0155788 A1 | 6/2011 | Hillstead et al. |
| 2011/0163146 A1 | 7/2011 | Ortiz et al. |
| 2011/0163147 A1 | 7/2011 | Laurent et al. |
| 2011/0163149 A1 | 7/2011 | Viola |
| 2011/0163150 A1 | 7/2011 | Farascioni |
| 2011/0168757 A1 | 7/2011 | Viola et al. |
| 2011/0168760 A1 | 7/2011 | Viola et al. |
| 2011/0174862 A1 | 7/2011 | Shelton, IV et al. |
| 2011/0174863 A1 | 7/2011 | Shelton, IV et al. |
| 2011/0180585 A1 | 7/2011 | Czernik et al. |
| 2011/0186614 A1 | 8/2011 | Kasvikis |
| 2011/0192881 A1 | 8/2011 | Balbierz et al. |
| 2011/0192882 A1 | 8/2011 | Hess et al. |
| 2011/0192883 A1 | 8/2011 | Whitman et al. |
| 2011/0198385 A1 | 8/2011 | Whitman et al. |
| 2011/0198386 A1 | 8/2011 | Viola |
| 2011/0204119 A1 | 8/2011 | McCuen |

(56) References Cited

U.S. PATENT DOCUMENTS

| | | | |
|---|---|---|---|
| 2011/0204120 A1 | 8/2011 | Crainich | |
| 2011/0210157 A1 | 9/2011 | Knodel et al. | |
| 2011/0215132 A1 | 9/2011 | Aranyi et al. | |
| 2011/0215133 A1 | 9/2011 | Aranyi | |
| 2011/0226837 A1* | 9/2011 | Baxter et al. | 227/175.1 |
| 2011/0233258 A1 | 9/2011 | Boudreaux | |
| 2011/0233259 A1 | 9/2011 | Olson | |
| 2011/0240713 A1 | 10/2011 | Scirica et al. | |
| 2011/0240714 A1 | 10/2011 | Whitman et al. | |
| 2011/0253765 A1 | 10/2011 | Nicholas et al. | |
| 2011/0257679 A1 | 10/2011 | Ishitsuki et al. | |
| 2012/0312858 A1* | 12/2012 | Patankar | A61B 17/07207 227/176.1 |
| 2012/0312859 A1* | 12/2012 | Gupta | A61B 17/07207 227/176.1 |
| 2012/0312861 A1* | 12/2012 | Gurumurthy et al. | 227/177.1 |
| 2013/0037594 A1* | 2/2013 | Dhakad | A61B 17/07207 227/175.2 |
| 2013/0037595 A1* | 2/2013 | Gupta | A61B 17/07207 227/175.2 |
| 2013/0037597 A1* | 2/2013 | Katre | A61B 17/072 227/176.1 |
| 2014/0353357 A1* | 12/2014 | Agarwal | A61B 17/07207 227/176.1 |

FOREIGN PATENT DOCUMENTS

| | | |
|---|---|---|
| DE | 2744824 | 4/1978 |
| DE | 2903159 | 1/1980 |
| DE | 3114135 | 10/1982 |
| DE | 4213426 | 10/1992 |
| DE | 4300307 | 7/1994 |
| EP | 0041022 | 12/1981 |
| EP | 0136950 | 4/1985 |
| EP | 0140552 | 5/1985 |
| EP | 0156774 | 10/1985 |
| EP | 0178940 A2 | 4/1986 |
| EP | 0216532 | 4/1987 |
| EP | 0220029 | 4/1987 |
| EP | 0213817 | 11/1987 |
| EP | 0273468 | 7/1988 |
| EP | 0324166 | 7/1989 |
| EP | 0324635 | 7/1989 |
| EP | 0324637 | 7/1989 |
| EP | 0324638 | 7/1989 |
| EP | 0369324 | 5/1990 |
| EP | 0373762 | 6/1990 |
| EP | 0380025 | 8/1990 |
| EP | 0380025 A2 | 8/1990 |
| EP | 0399701 | 11/1990 |
| EP | 0449394 | 10/1991 |
| EP | 0484677 | 5/1992 |
| EP | 0489436 | 6/1992 |
| EP | 0503662 | 9/1992 |
| EP | 0514139 | 11/1992 |
| EP | 0536903 | 4/1993 |
| EP | 0537572 | 4/1993 |
| EP | 0539762 | 5/1993 |
| EP | 0545029 | 6/1993 |
| EP | 0552050 | 7/1993 |
| EP | 0552423 | 7/1993 |
| EP | 0579038 | 1/1994 |
| EP | 0589306 | 3/1994 |
| EP | 0591946 | 4/1994 |
| EP | 0592243 | 4/1994 |
| EP | 0593920 | 4/1994 |
| EP | 0598202 | 5/1994 |
| EP | 0598579 | 5/1994 |
| EP | 0600182 | 6/1994 |
| EP | 0621006 | 10/1994 |
| EP | 0621009 | 10/1994 |
| EP | 0656188 | 6/1995 |
| EP | 0365153 | 8/1995 |
| EP | 0666057 | 8/1995 |
| EP | 0705571 | 4/1996 |
| EP | 0760230 | 3/1997 |
| EP | 2018826 A2 | 1/2009 |
| EP | 2090233 A2 | 8/2009 |
| EP | 2532311 A2 | 12/2012 |
| EP | 2532313 A2 | 12/2012 |
| FR | 2542188 | 9/1984 |
| FR | 2660851 | 10/1991 |
| FR | 2681775 | 10/1991 |
| GB | 1352554 | 4/1971 |
| GB | 0411985 | 10/1976 |
| GB | 1452185 | 10/1976 |
| GB | 1555455 | 11/1979 |
| GB | 2048685 | 12/1980 |
| GB | 2070499 | 9/1981 |
| GB | 2141066 | 12/1984 |
| SU | 659146 | 4/1979 |
| SU | 728848 | 5/1980 |
| SU | 980703 | 12/1982 |
| SU | 990220 | 1/1983 |
| WO | WO 8302247 | 7/1983 |
| WO | WO 89/10094 | 11/1989 |
| WO | WO 9210976 | 7/1992 |
| WO | WO 9308754 | 5/1993 |
| WO | WO 9314706 | 8/1993 |
| WO | WO03/094743 A1 | 11/2003 |
| WO | WO2013/022703 A1 | 2/2013 |
| WO | WO2013/109445 A2 | 7/2013 |

OTHER PUBLICATIONS

International Search Report for PCT/US12/49343 date of completion is Oct. 30, 2012 (6 pages).

International Search Report for PCT/US12/49347 date of completion is Oct. 4, 2012 (6 pages).

International Search Report for PCT/US13/68216 date of completion is Sep. 5, 2014 (9 pages).

Chinese Office Action issued in corresponding application No. 201280038907.6 on Aug. 24, 2015.

Chinese Office Action issued in corresponding application No. 201280038907.6 on May 3, 2016.

Chinese Office Action issued in corresponding application No. 201280038907.6 on Nov. 9, 2016.

* cited by examiner

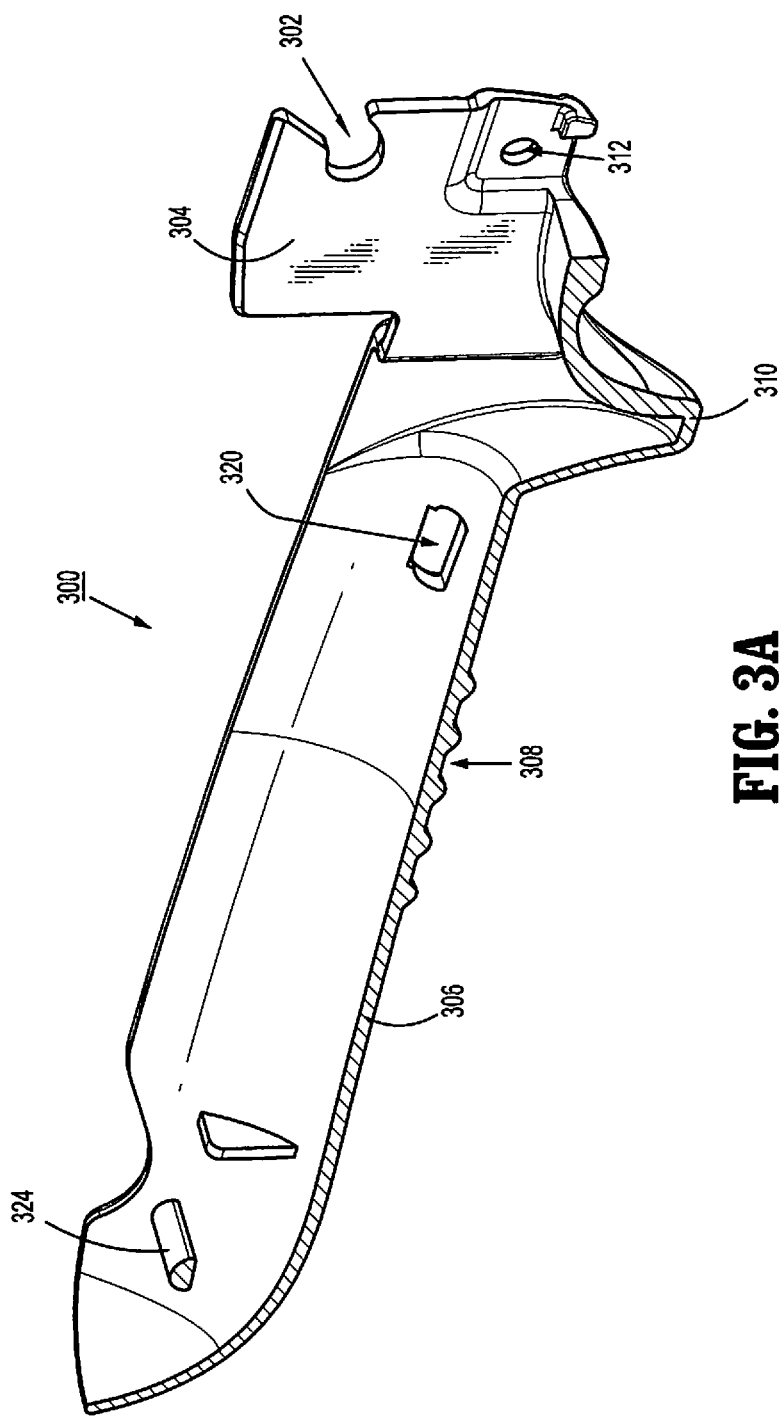

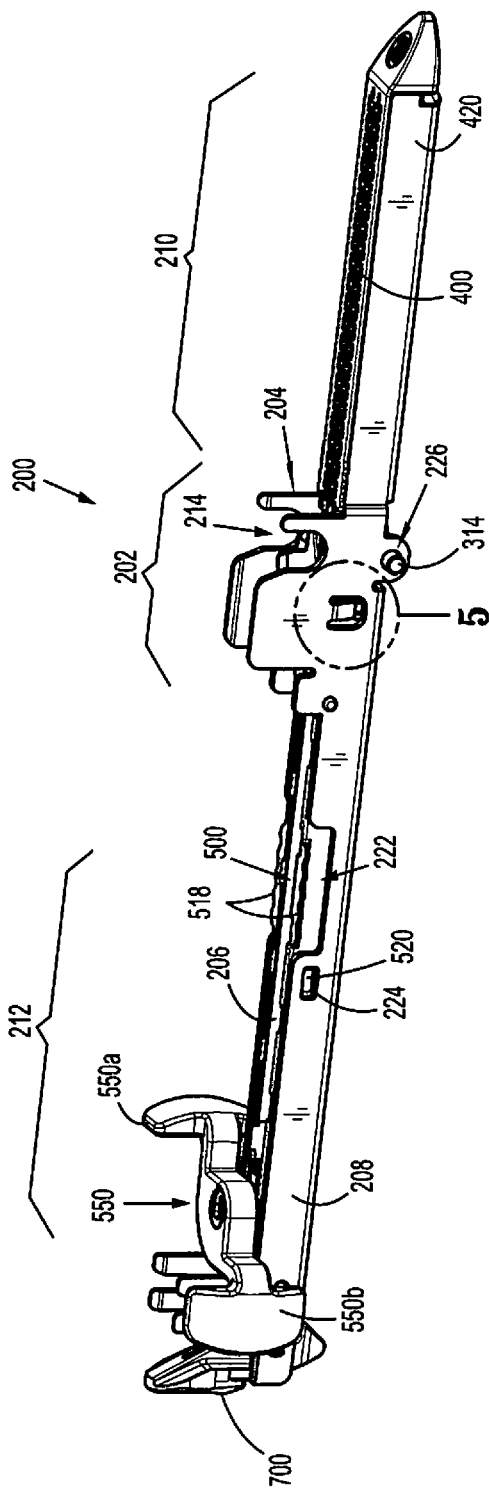
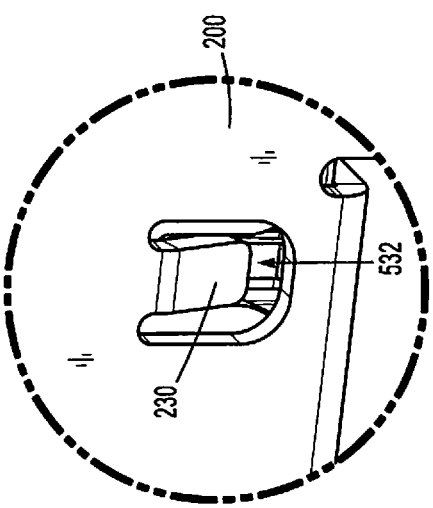
FIG. 4
FIG. 5

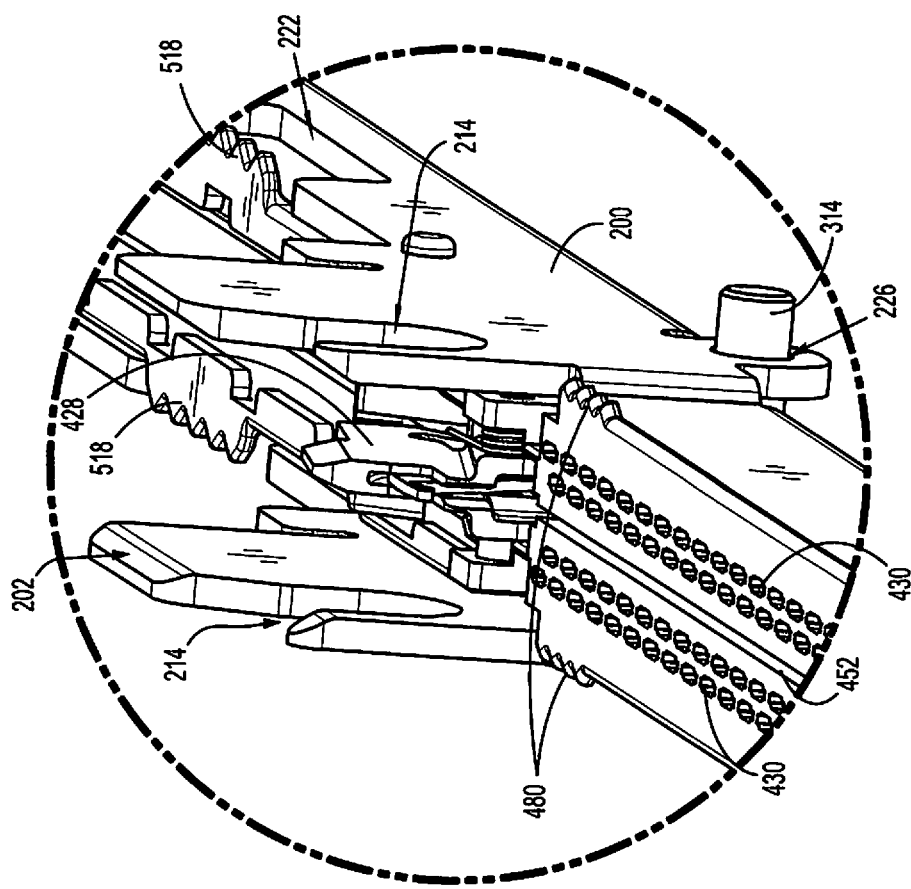
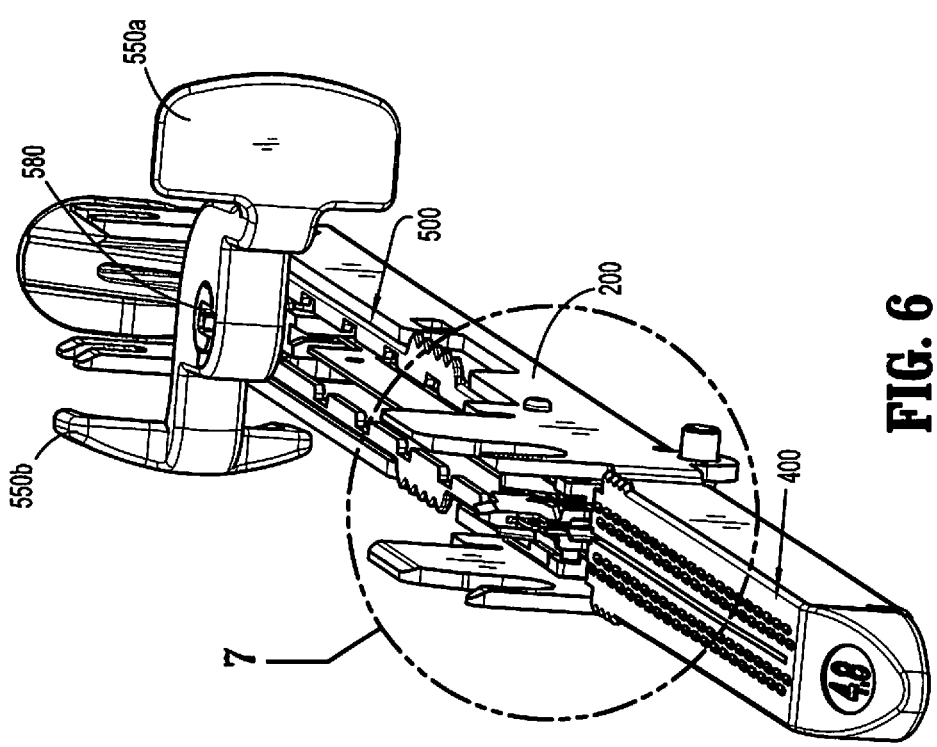
FIG. 7
FIG. 6

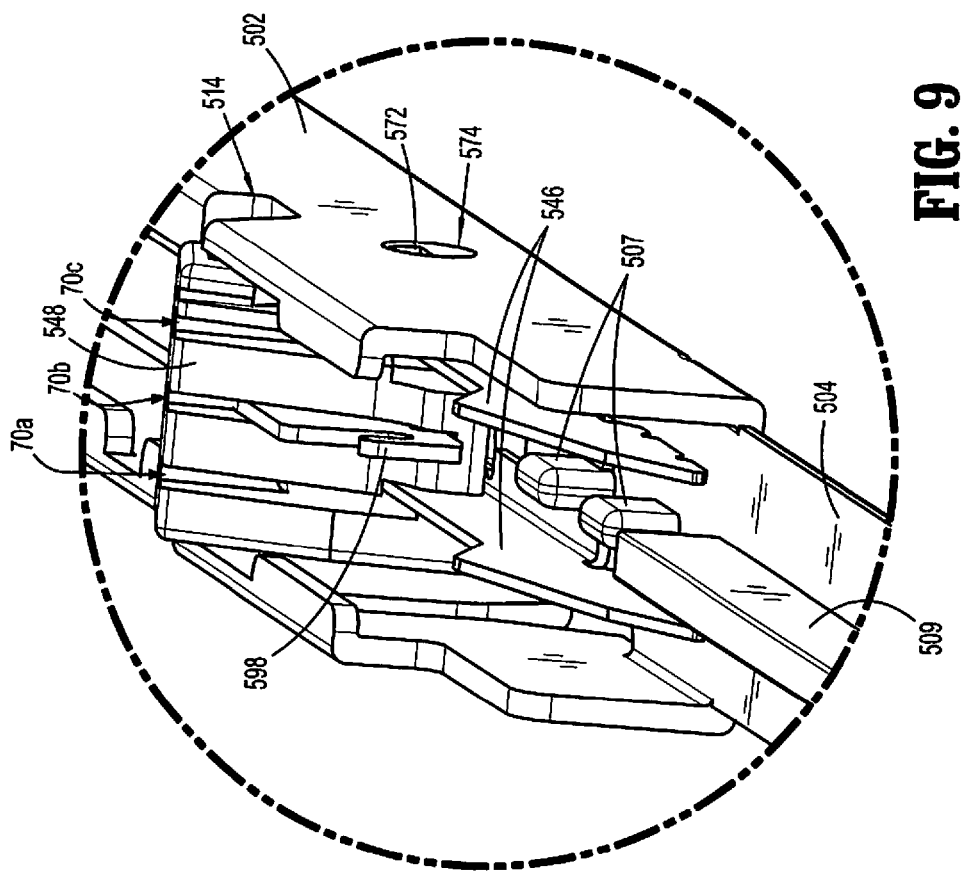
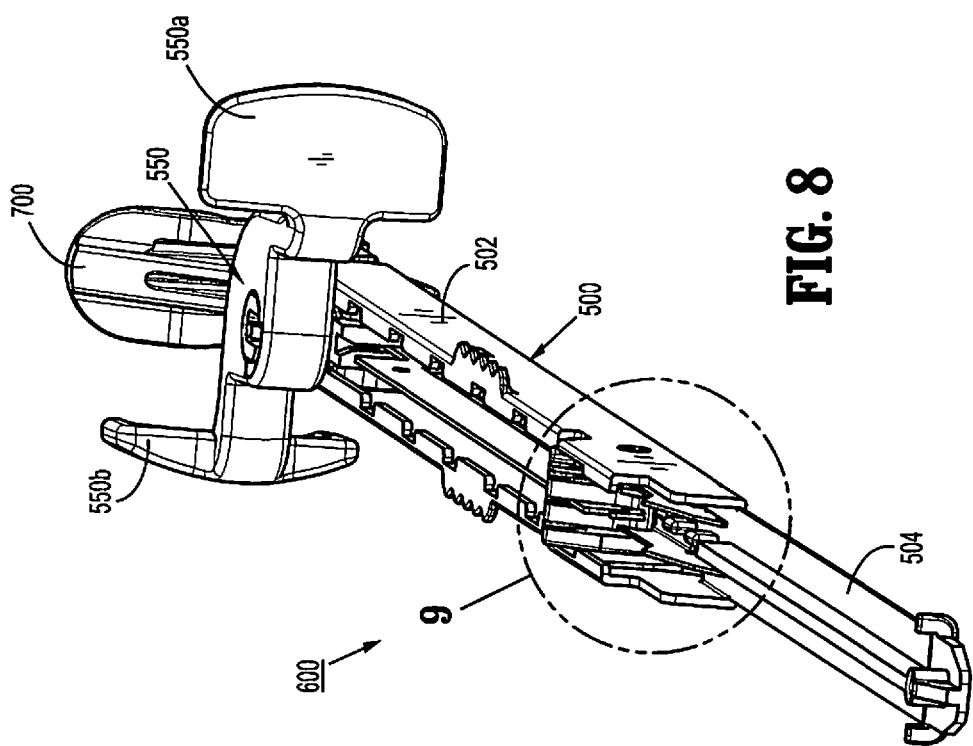

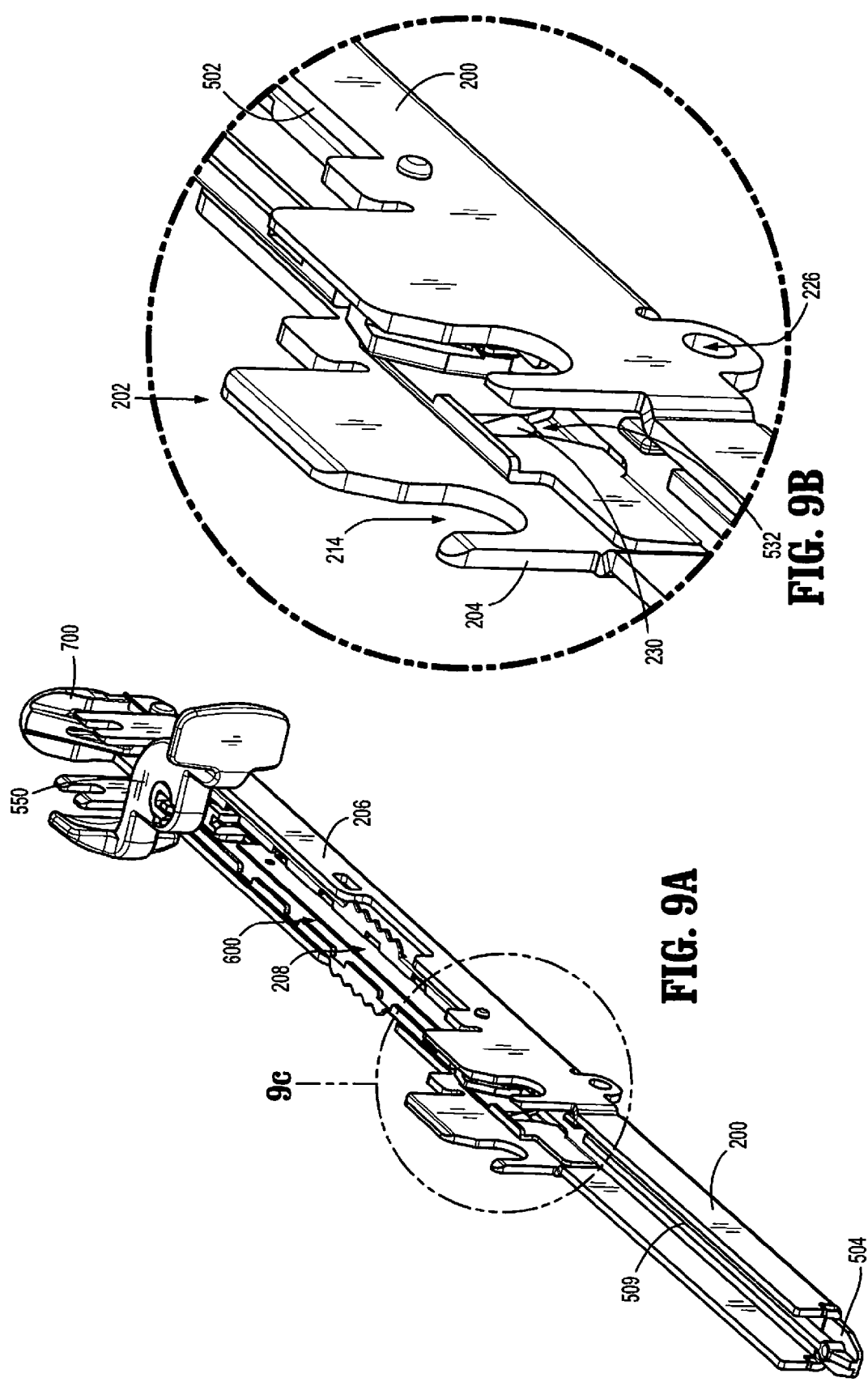

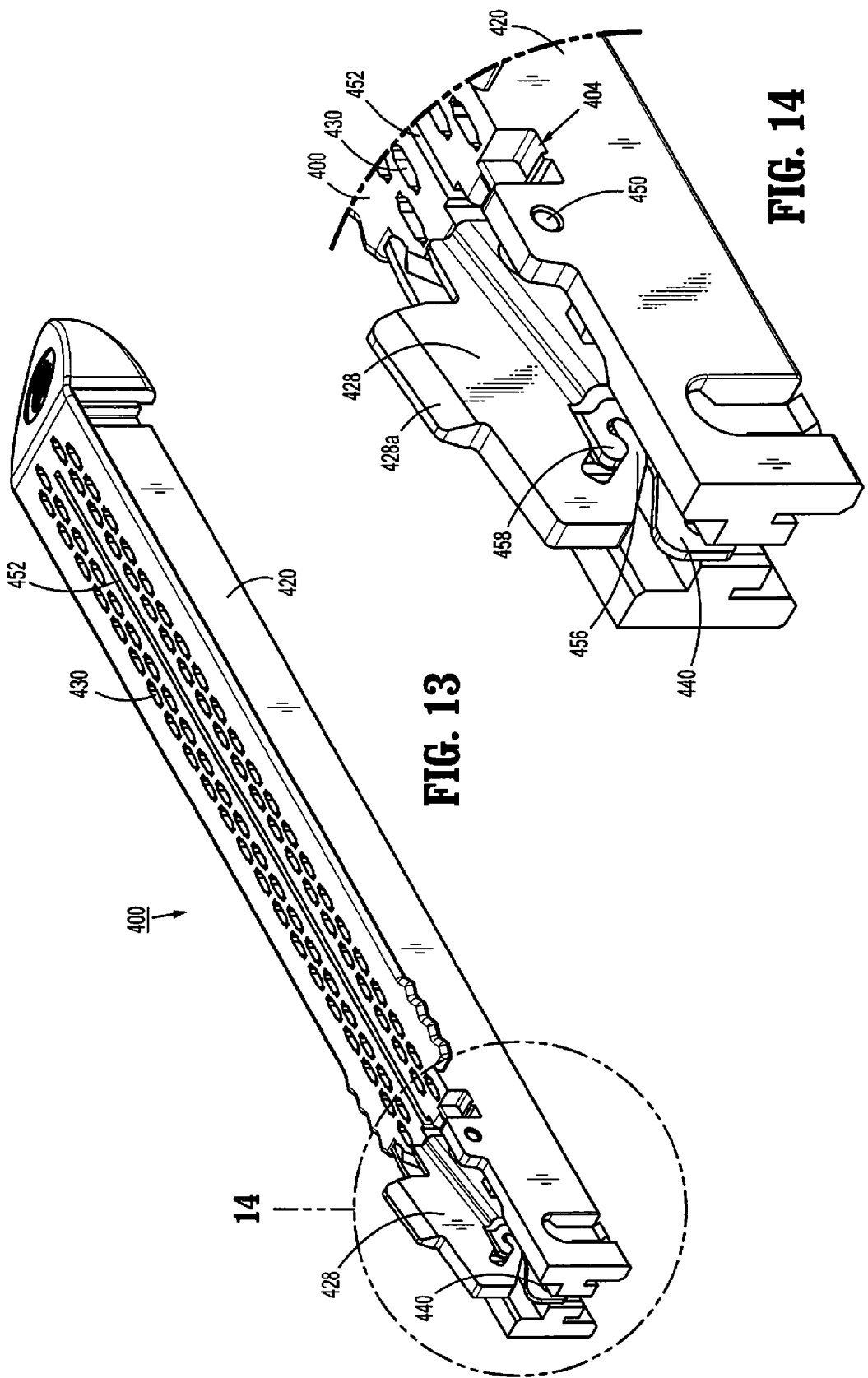

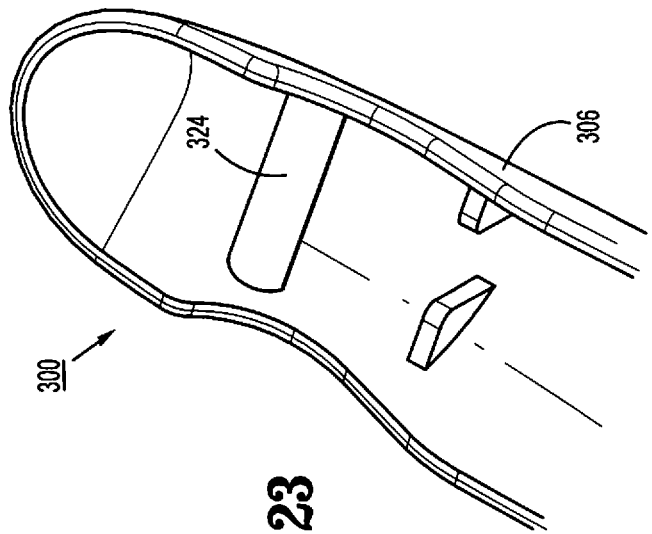
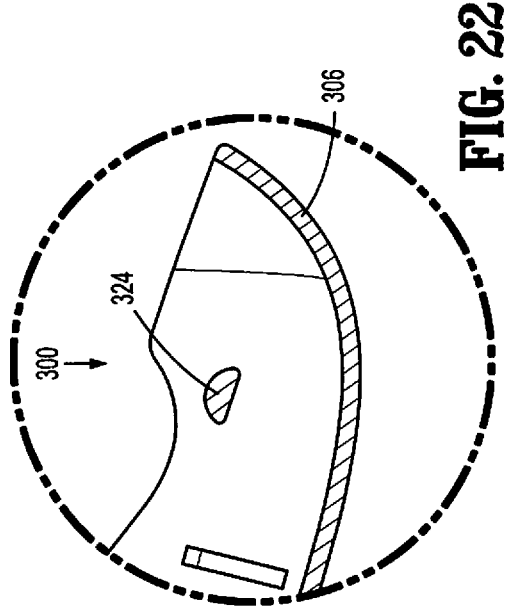
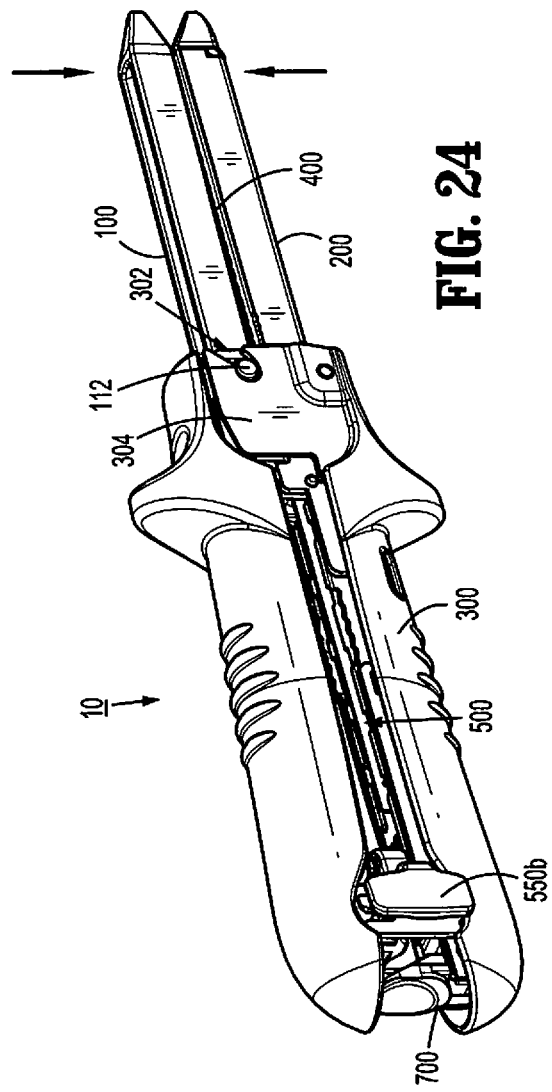
FIG. 22
FIG. 23
FIG. 24

SURGICAL FASTENER APPLYING APPARATUS

This application claims priority from provisional application Ser. No. 61/521,070, filed Aug. 8, 2011, the entire contents of which are incorporated herein by reference.

BACKGROUND

Technical Field

The present disclosure relates to a surgical fastener applying apparatus and, more particularly, to a surgical fastener applying apparatus having both reusable and disposable components.

Background of Related Art

Surgical fastener applying apparatus grasp or clamp tissue between opposing jaw structures and join the tissue by means of surgical fasteners. In some such apparatus, a knife is provided to cut the tissue which has been joined by the fasteners. The fasteners are typically in the form of surgical staples, although other surgical fasteners may also be utilized, such as, for example, clips or two part polymeric surgical fasteners.

Surgical fastener applying apparatus typically include two elongated beam members which are used to capture or clamp tissue therebetween. Typically, one of the beam members carries a disposable cartridge assembly which houses a plurality of staples arranged in at least two lateral rows, while the other beam member includes an anvil which defines a surface for forming the staple legs as the staples are driven from the cartridge assembly. Where two part fasteners are used, the beam member which includes the anvil carries a mating part of the two part fastener, e.g. the receiver. Generally, the staple formation process is affected by the interaction between one or more longitudinally moving camming members and a series of individual staple pushers. As the camming members travel longitudinally through the cartridge carrying beam member, the individual staple pushers are biased upwardly into a backspan of the staples supported within the cartridge assembly to sequentially eject the staples from the cartridge. A knife may be provided to travel with the camming members between the staple rows to cut the tissue between the rows of formed staples. An example of such an instrument is disclosed in U.S. Pat. No. 7,631,794, which is incorporated herein in its entirety by reference.

Although reusable fastener applying apparatus have been developed, such apparatus can be overly complex and prove difficult to sterilize. Because of the difficulties associated with properly sterilizing a fastener applying apparatus for reuse, fastener applying apparatus are typically configured as disposable apparatus. In such disposable apparatus, the cartridge assembly may be replaced to perform multiple fastener applying operations on a single patient, although the fastener applying apparatus is typically disposed after the surgical procedure has been completed. This need for disposability may increase the costs associated with surgical procedures.

Therefore, a need exists in the art for a fastener applying apparatus which includes reusable components, is not overly complex, and is configured to facilitate proper sterilization after use in a surgical procedure.

SUMMARY

In accordance with one aspect of the present disclosure, a surgical fastener applying apparatus is provided. The apparatus includes an anvil half-section including a distal anvil portion and a proximal handle portion and a cartridge-receiving half-section including an elongated channel member. A pair of opposed openings are defined through sidewalls of the elongated channel member of the cartridge-receiving half-section. A clamping lever is secured to the cartridge receiving half-section and includes a proximal end, a distal end and a handle portion. A disposable assembly including a single use loading unit and a firing unit is configured to be releasably supported within the cartridge-receiving half-section. The disposable assembly includes a stationary housing for supporting the firing unit. The stationary housing includes a distal extension extending therefrom for supporting the single use loading unit. The stationary housing further includes a pair of flared tabs extending outwardly therefrom. The flared tabs are configured to be releasably received within the opposed openings of the cartridge-receiving half-section to releasably engage the disposable assembly within the cartridge-receiving half-section. The clamping lever is operably associated with the anvil half-section and the cartridge receiving half-section and is movable relative thereto from an unclamped position to a clamped position to releasably secure the anvil portion of the anvil half-section in close approximation with the single use loading unit.

In one embodiment, the stationary housing further defines a pair of opposed slots positioned towards a proximal end thereof. The cartridge-receiving half-portion can include a pair of protrusions disposed at the proximal end thereof and extending inwardly from the sidewalls thereof, the protrusions configured to be received within the slots when the disposable assembly is positioned within the cartridge-receiving half-section.

The disposable assembly may further include a pivotal locking member coupled to the stationary housing and configured to engage an engagement member positioned on the clamping lever to lock the clamping member in the clamped position.

In one embodiment, the firing unit includes a firing lever and a cam bar fixedly secured to the firing lever, the firing lever selectively translatable relative to the stationary housing to similarly translate the cam bar through the single use loading unit to eject fasteners therefrom.

The firing unit may further include a guide block pivotably supported within the stationary housing, the guide block configured to guide translation of the cam bar through the single use loading unit. The guide block can be pivotable between a locked position inhibiting translation of the cam bar, and an unlocked position permitting translation of the cam bar. The firing assembly may further include a knife actuating bar wherein, in the locked position, the guide block is engaged with the knife actuating bar. The anvil half-section may include one or more extensions extending therefrom that are configured to urge the guide block to the unlocked position upon movement of the clamping lever to the clamped position.

In one embodiment, the stationary housing includes a pair of outwardly-extending serrated gripping surfaces to facilitate insertion and removal of the disposable assembly in relation to the cartridge-receiving half-section. The cartridge-receiving half-section may include a pair of cut-out portions configured to receive the serrated surface upon insertion of the disposable assembly into the cartridge-receiving half-section.

In one embodiment, the flared tabs are biased into engagement with the opposed openings. Sidewalls of the stationary housing can in one embodiment be manually movable toward each other to retract the flared tabs from two opposed openings to permit withdrawal of the stationary housing from the cartridge-receiving half section.

In accordance with another aspect of the present disclosure, a surgical fastener applying apparatus is provided which includes an anvil half-section including a distal anvil portion and a proximal handle portion and a cartridge-receiving half-section including an elongated channel member. A clamping lever is secured to the cartridge receiving half-section and has a proximal end and a distal end and includes a handle portion. A disposable assembly including a single use loading unit and a single use firing unit is also provided. The disposable assembly is configured to be releasably supported within the cartridge-receiving half-section and includes a stationary housing for supporting the firing unit that has a distal extension extending therefrom for supporting the single use loading unit. The single use loading unit is engaged to the distal extension at both the distal end thereof and the proximal end thereof via independent engagements. The clamping lever is operably associated with the anvil half-section and the cartridge receiving half-section and is movable from an unclamped position to a clamped position to releasably secure the anvil portion of the anvil half-section in close approximation with the single use loading unit.

In one embodiment, the single use loading unit is engaged to the distal extension at the distal end of the single use loading unit via a male-female connection secured via a snap-fit engagement. The male-female connection at the distal end of the single use loading unit may include a post extending from the single use loading unit that is configured to be received within a lumen defined within the distal extension. The snap-fit engagement at the distal end of the single use loading unit may include a pair of cantilever arms extending from the distal extension that are configured to engage a pair of cutouts defined within the single use loading unit.

In one embodiment, the single use loading unit is engaged to the distal extension at the proximal end of the single use loading unit via a male-female connection secured via a snap-fit engagement. The male-female connection at the proximal end of the single use loading unit may include one or more slots defined within the single use loading unit that are configured to receive one or more protrusions extending from the distal extension. The snap-fit engagement at the proximal end of the single use loading unit may include a pair of inwardly-extending tabs disposed on the stationary housing and configured to snap-over the proximal end of the single use loading unit.

Also provided in accordance with another aspect of the present disclosure is a surgical fastener applying apparatus that includes an anvil half-section including a distal anvil portion and a proximal handle portion and a cartridge-receiving half-section including an elongated channel member. A clamping lever is secured to the cartridge receiving half-section and has a proximal end and a distal end and including a handle portion. A disposable assembly including a single use loading unit and a single use firing unit is also provided. The disposable assembly is configured to be releasably supported within the cartridge-receiving half-section and includes a stationary housing for supporting the firing unit. The stationary housing includes a distal extension extending therefrom for supporting the single use loading unit. Each of the single use loading unit and the stationary housing include a pair of opposed serrated gripping surfaces extending therefrom. Each pair of serrated gripping surfaces is configured to facilitate insertion and removal of the disposable assembly from the cartridge-receiving half-section. The clamping lever is operably associated with the anvil half-section and the cartridge receiving half-section and is movable from an unclamped position to a clamped position to releasably secure the anvil portion of the anvil half-section in close approximation with the single use loading unit.

In one embodiment, the cartridge-receiving half-section includes a pair of cut-out portions configured to receive the serrated gripping surfaces of the stationary housing upon insertion of the disposable assembly into the cartridge-receiving half-section.

In one embodiment, a pivotal locking member is coupled to the disposable assembly, the locking member configured to engage an engagement member positioned on the clamping lever to lock the clamping member in the clamped position.

BRIEF DESCRIPTION OF THE DRAWINGS

Various embodiments of the presently disclosed surgical fastener applying apparatus are described herein with reference to the drawings wherein:

FIG. 3A is a side, cross-sectional view of the clamp lever of the fastener applying apparatus shown in FIG. 1;

FIG. 4 is a side, perspective view of the cartridge receiving half-section of the surgical fastener applying apparatus shown in FIG. 1 with the disposable assembly supported within the cartridge receiving half-section;

FIG. 5 is an enlarged view of the indicated area of detail shown in FIG. 4;

FIG. 6 is a perspective view from above of the cartridge receiving half-section of the surgical fastener applying apparatus with the disposable assembly supported therein;

FIG. 7 is an enlarged view of the indicated area of detail shown in FIG. 6;

FIG. 8 is a front end, perspective view from above of the disposable assembly of the surgical fastener applying apparatus shown in FIG. 3 with the SULU removed;

FIG. 9 is an enlarged view of the indicated area of detail shown in FIG. 8;

FIG. 9A is a top, perspective view of the channel member with the firing unit of the disposable assembly mounted therein;

FIG. 9B is an enlarged view of the indicated area of detail shown in FIG. 9A;

FIG. 13 is a side, perspective view of the SULU of the surgical fastener applying apparatus shown in FIG. 1;

FIG. 14 is an enlarged view of the indicated area of detail shown in FIG. 13;

FIG. 22 is an enlarged view of the indicated area of detail shown in FIG. 18;

FIG. 23 is a perspective view from below of the proximal end of the clamping lever of the surgical fastener applying apparatus shown in FIG. 1;

FIG. 24 is a side, perspective view of the surgical fastener applying apparatus shown in FIG. 1 in the clamped position;

DETAILED DESCRIPTION

Figure 1:
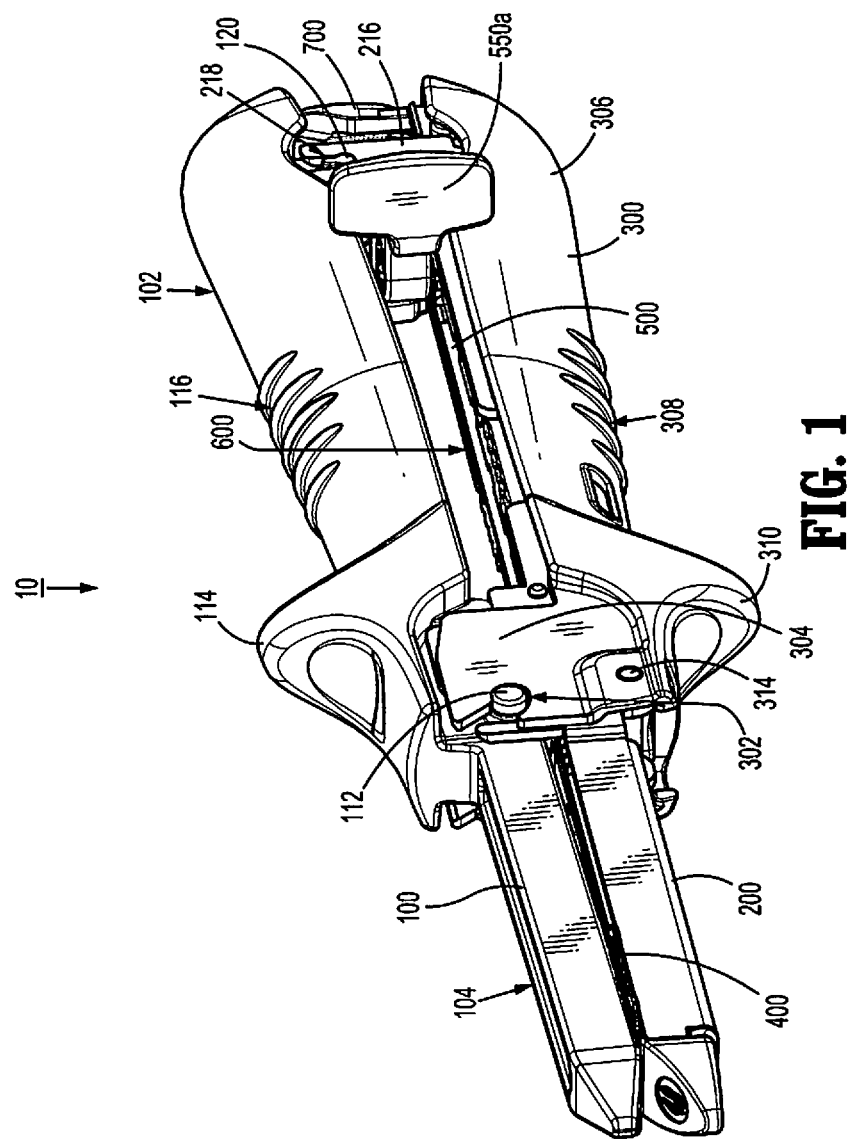
FIG. 1 is a side, perspective view from the distal end of one embodiment of the presently disclosed surgical fastener applying apparatus in the clamped position.

Embodiments of the presently disclosed surgical fastener applying apparatus in accordance with the present disclosure will now be described in detail with reference to FIGS. 1-34, wherein like reference numerals identify similar or identical structural elements. As used herein, as is traditional, the term "proximal" refers to the end of the apparatus which is closer to the user and the term distal refers to the end of the apparatus which is further away from the user.

Figure 2:
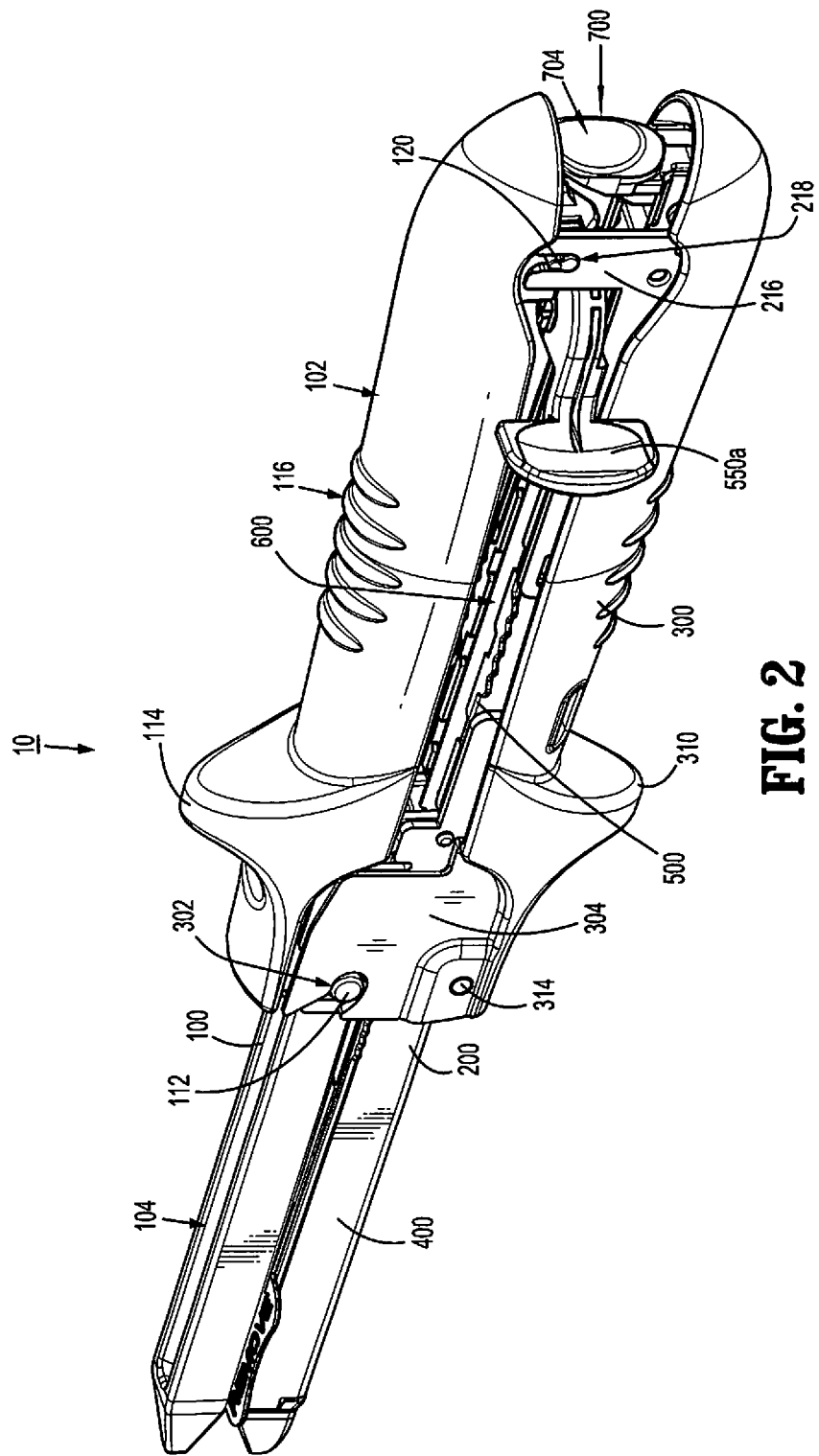
FIG. 2 is a side, perspective view from the proximal end of the surgical fastener applying apparatus shown in FIG. 1 in the clamped position.
Figure 3:
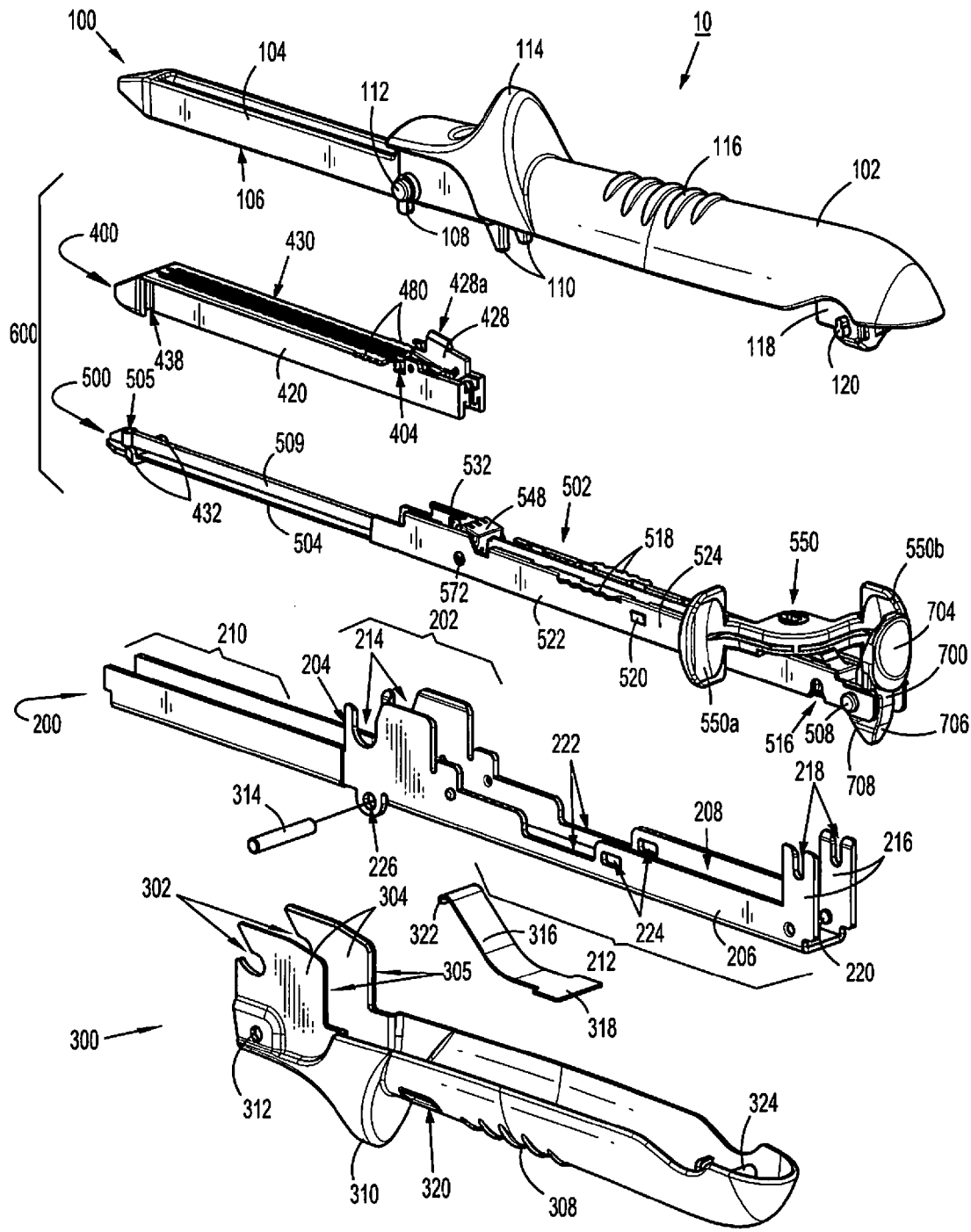
FIG. 3 is a side, perspective view with parts separated of the surgical fastener applying apparatus shown in FIG. 1.
Figure 9C:
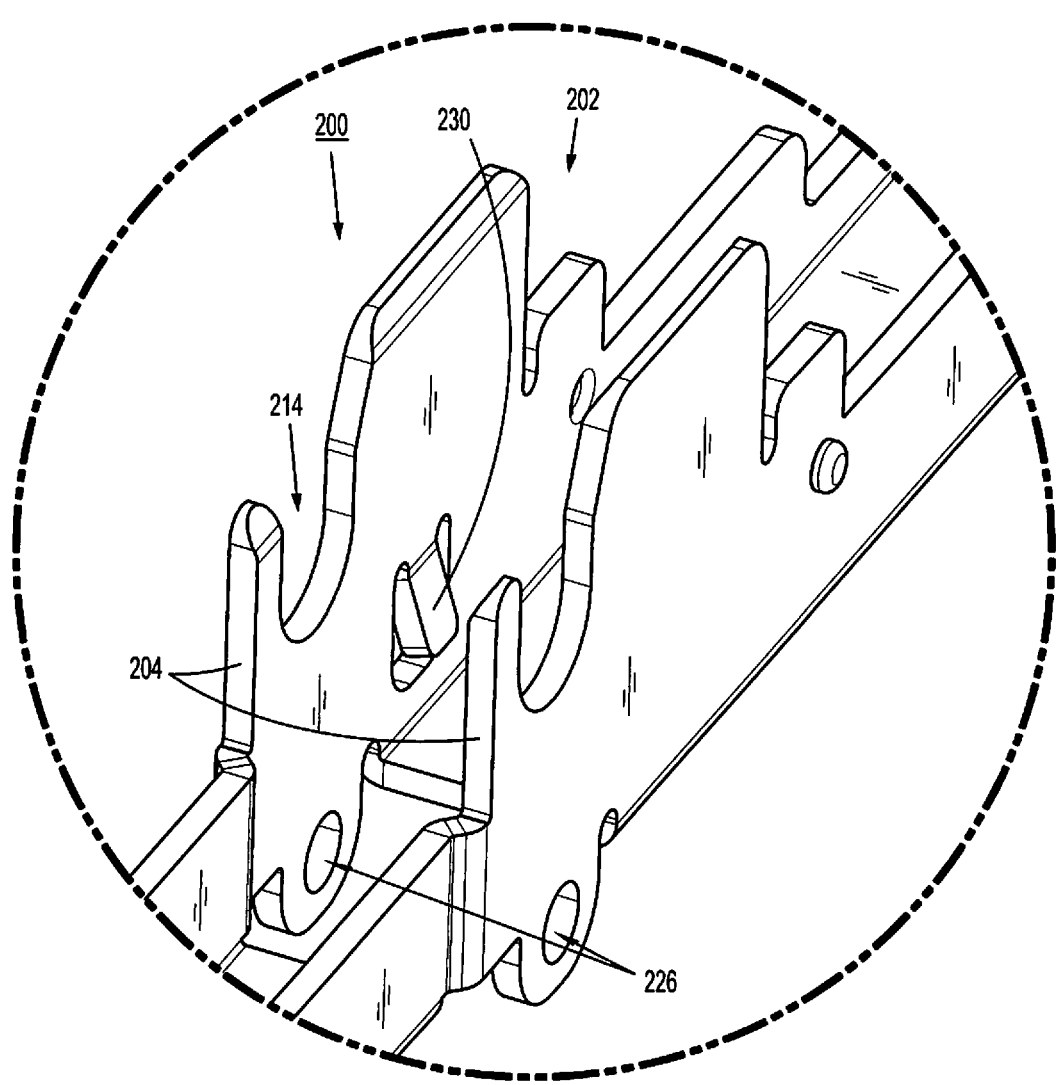
FIG. 9C is a top, perspective view of a central portion of the channel member.
Figure 11:
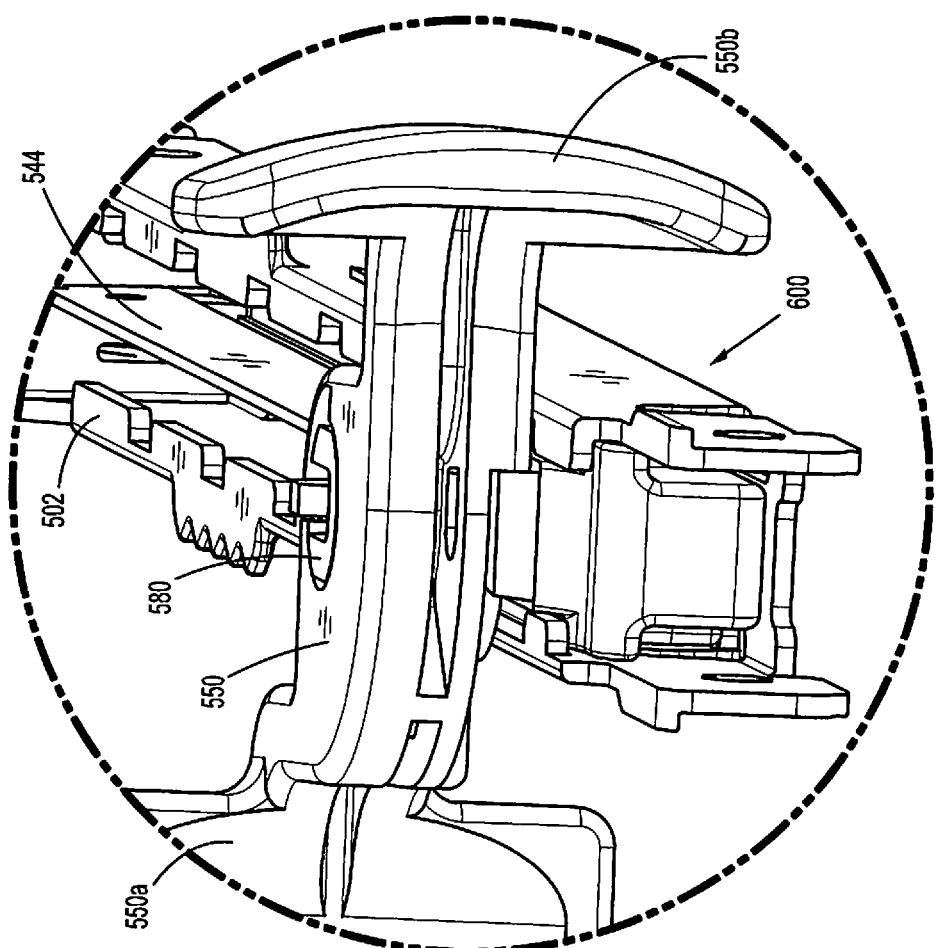
FIG. 11 is an enlarged view of the indicated area of detail shown in FIG. 10.
Figure 10:
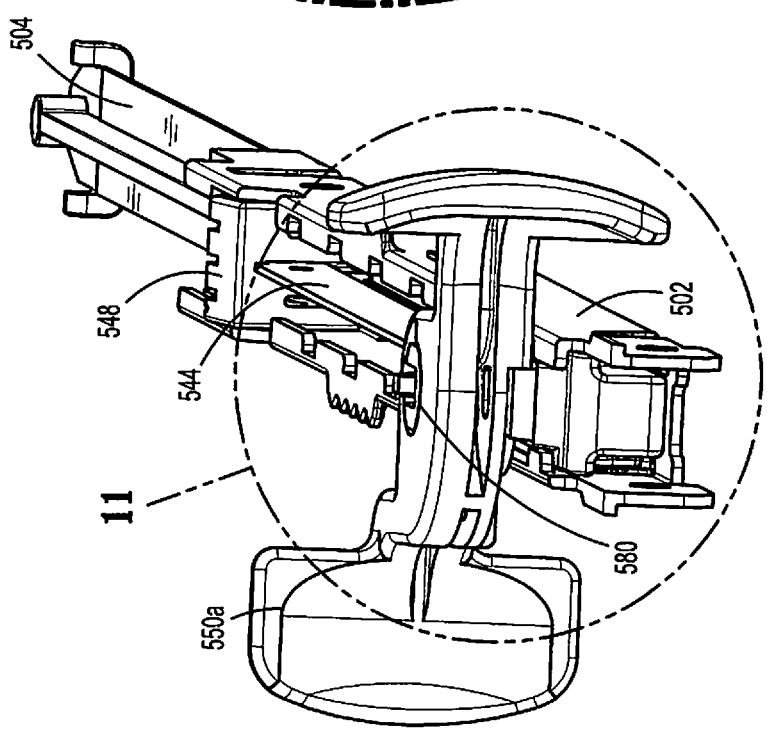
FIG. 10 is a rear end, perspective view from above of the disposable assembly absent the SULU shown in FIG. 8.

Turning to FIGS. 1-3, one embodiment of the presently disclosed surgical fastener applying apparatus is shown generally identified as surgical stapler 10. Surgical stapler 10 includes an anvil half-section 100, a cartridge-receiving half-section 200, a clamping lever 300, and a disposable assembly 600 including a single use loading unit 400 (hereinafter "SULU") and a firing unit 500. Each of these components or assemblies will be described in greater detail hereinbelow.

Anvil half-section 100, cartridge-receiving half-section 200 and clamping lever 300 may be configured as reusable components and, as such, are constructed from biocompatible materials suitable for sterilization and repeated use, e.g., stainless steel. SULU 400 and firing unit 500, on the other hand, are integrated with one another to form disposable assembly 600. The integration of SULU 400 and firing unit 500 into a single disposable assembly 600 facilitates disengagement and separation of the disposable components of surgical stapler 10 from the reusable components of surgical stapler 10 as a single unit, thus facilitating disposal of the disposable components and preparation of the reusable components for sterilization. Such a configuration also facilitates engagement of a new disposable assembly 600 with the sterilized reusable components in preparation for subsequent use. The integration of SULU 400 and firing unit 500 also facilitates removal of the used disposable assembly and replacement with a fresh disposable assembly for subsequent firings in a single surgical procedure. Disposable assembly 600, e.g., SULU 400 and firing unit 500, may be constructed from any suitable biocompatible materials, e.g., plastics, metals, or combinations thereof. Further, surgical stapler 10 may be configured to receive or accommodate disposable assemblies of various different configurations, e.g., disposable assemblies including SULU's and firing assemblies for firing staples of different staple line lengths (e.g., 60 mm, 80 mm and 100 mm).

As will be described in greater detail below, anvil half-section 100 and cartridge-receiving half-section 200 are releasably pivotably engagable with one another, while clamping lever 300 is pivotably coupled to cartridge-receiving half-section 200 about a central portion 202 thereof. Clamping lever 300 is pivotable relative to cartridge-receiving half-section 200 between a spaced-apart position (FIG. 2A) and an approximated position (FIGS. 1-2) for moving cartridge-receiving half-section 200 and anvil half-section 100 relative to one another between an open, or un-clamped position (FIG. 2A, FIG. 33) and a closed, or clamped position (FIGS. 1-2) for clamping tissue therebetween. With surgical stapler 10 in the clamped position, firing unit 500 may be operated to sequentially fire and form a plurality of surgical staples 402 (FIG. 17) about tissue clamped between anvil half-section 100 and cartridge-receiving half-section 200 and for advancing a knife 440 (FIG. 17) to divide tissue between the stapled portions thereof.

Continuing with reference to FIGS. 1-3, anvil half-section 100 includes a proximal handle portion 102 and a distal anvil portion 104. Anvil portion 104 includes staple deforming portion 106 which includes a plurality of staple deforming recesses (not shown) defined therein. Staple deforming portion 106 is disposed in opposing relation relative to SULU 400 when disposable assembly 600 is engaged within channel member 206 of cartridge-receiving half-section 200. Further, staple deforming portion 106 includes a central longitudinal slot (not shown) for receiving knife 440 of SULU 400 (FIG. 17) as the knife 440 is advanced through SULU 400 to divide the stapled tissue. Staple deforming portion 106 can be formed integrally with anvil half-section 100 or, alternatively, may be secured to anvil half-section 100 by any suitable fastening process, e.g., welding.

Figure 26:
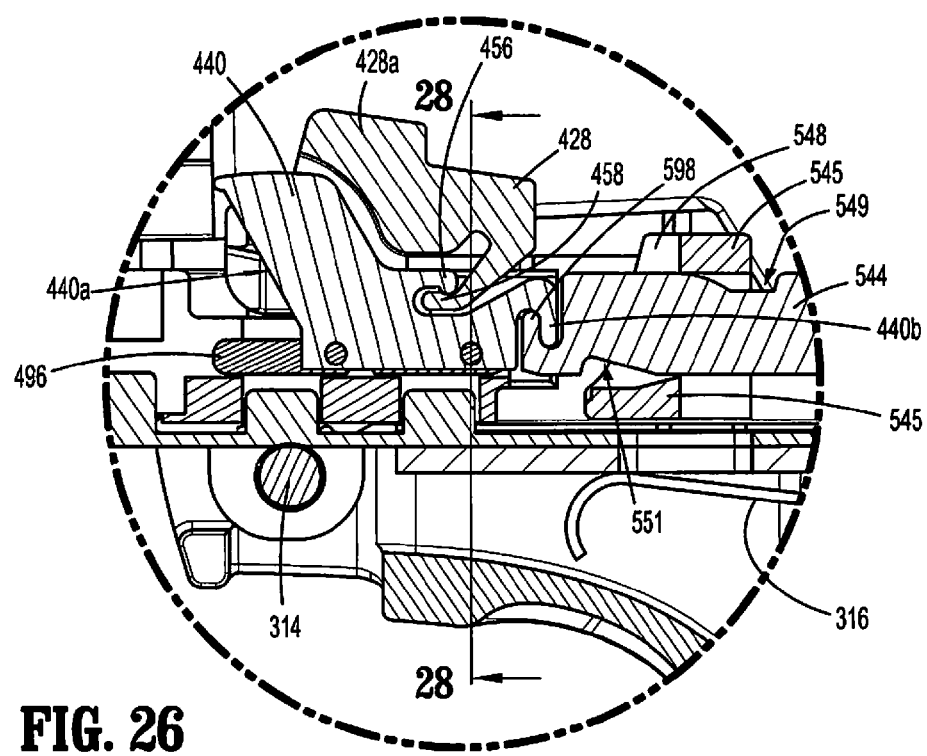
FIG. 26 is an enlarged view of the indicated area of detail shown in FIG. 25.

A pair of locating fingers 108 (FIG. 2A) disposed on a central portion of anvil half-section 100 and positioned adjacent the proximal end of the staple deforming portion 106 of anvil portion 104 extend from anvil half-section 100 towards SULU 400 of disposable assembly 600. Upon approximation of anvil half-section 100 and cartridge-receiving half-section 200, locating fingers 108 are at least partially received within grooves 404 (FIG. 2E) defined within SULU 400 to properly align SULU 400 with staple deforming portion 106 as surgical stapler 10 is moved to the clamped position. Anvil half-section 100 further includes a pair of transversely-spaced extensions 110 (FIG. 2A) positioned proximally of fingers 108 which extend downwardly towards disposable assembly 600. Extensions 110 each define an angled distal surface and are configured for engagement within notches 514 (FIG. 2E) of stationary housing 502 of disposable assembly 600 upon movement of surgical stapler 10 to the clamped position such that the angled distal surfaces of extensions 110 and notches 514 mate with one another. The angled surfaces of extensions 110 are each also configured to contact an upper surface of guide block 548 (FIG. 2E) as extensions 110 are translated towards notches 514, i.e., as surgical stapler 10 is moved towards the clamped position, such that, as will be described in greater detail below, guide block 548 is pivoted from a first, locked position (FIG. 19) to a second, unlocked position (FIG. 26).

Figure 2A:
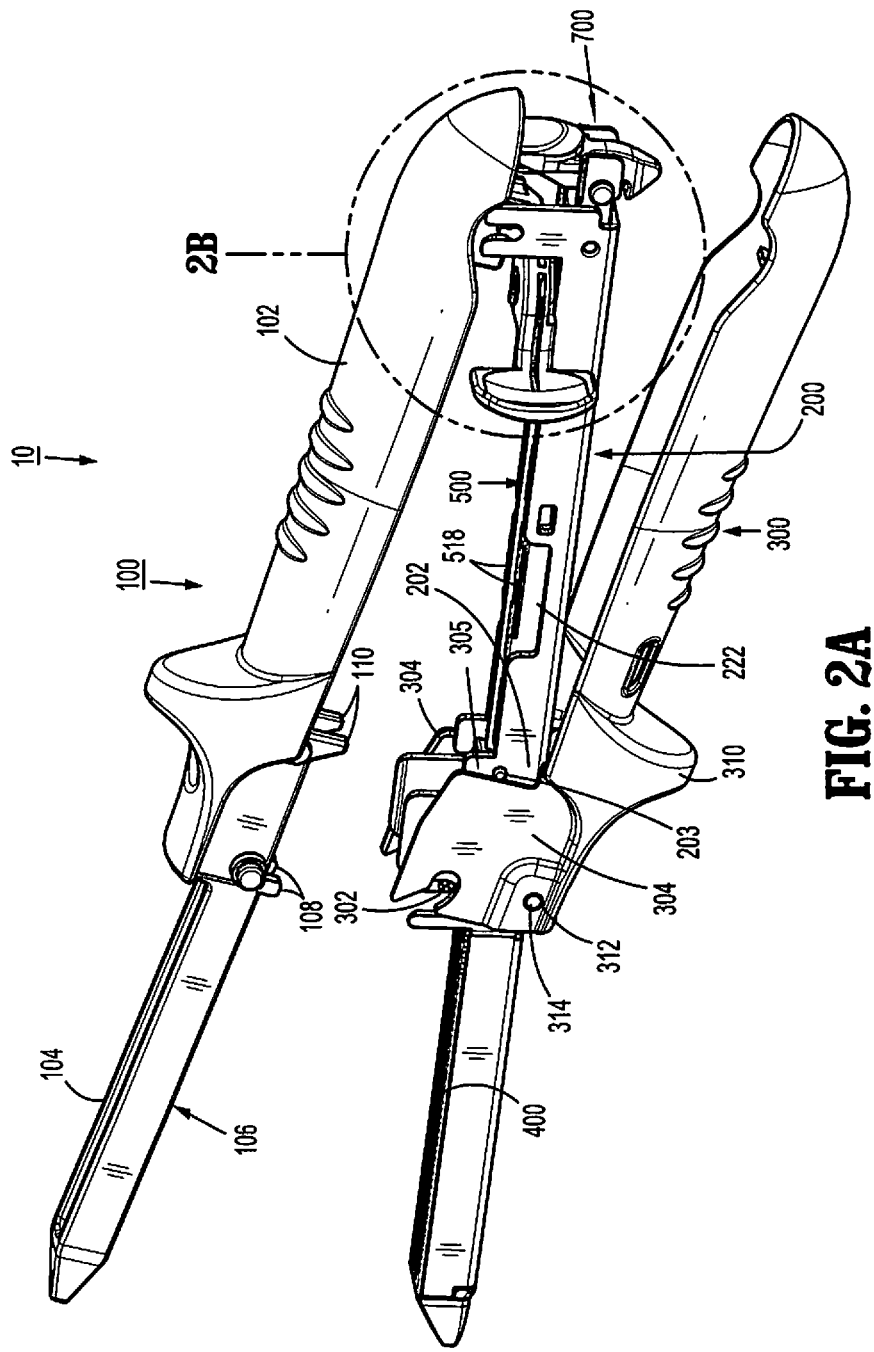
FIG. 2A is a side, perspective view of the surgical fastener applying apparatus shown in FIG. 1 in the open position.

Referring to FIGS. 2A and 3, a central portion of anvil half-section 100 includes a pair of cylindrical lateral support members 112. During assembly of anvil half-section 100 and cartridge-receiving half-section 200, lateral support members 112 are supported in U-shaped recesses 214 defined in a central portion 202 of cartridge-receiving half-section 200 (FIG. 3). A distal wall 204 of central portion 202 defines a tissue stop (FIG. 3). Lateral support members 112 are also positioned to be received in cutouts 302 formed on spaced flange portions 304 of clamping lever 300 when the clamping lever 300 is moved to the clamped position (FIG. 2). Proximal handle portion 102 is ergonomically formed and includes a thumb-engaging abutment 114 and a gripping portion 116. A proximal end of handle portion 102 includes a downwardly extending finger 118 which includes a pair of opposed teardrop shaped protrusions 120 (FIG. 3) which will be discussed in further detail below. Alternatively, protrusions 120 may assume a variety of other configurations.

Referring to FIGS. 3-7, cartridge-receiving half-section 200 includes an elongated channel member 206 having a substantially U-shaped channel 208 defined therein that is configured to releasably receive disposable assembly 600. More specifically, U-shaped channel 208 includes a distal portion 210 dimensioned to releasably receive distal extension 504 of stationary housing 502 of disposable assembly 600 which supports SULU 400, and a proximal portion 212 dimensioned to releasably receive the proximal portion of stationary housing 502 of disposable assembly 600 which supports firing unit 500. Disposable assembly 600 and the components thereof, i.e., SULU 400 and firing unit 500, will be described in greater detail hereinbelow.

As mentioned above, cartridge-receiving half-section 200 includes spaced centrally disposed U-shaped recesses 214 positioned to support lateral support members 112 of anvil half-section 100. The proximal end of cartridge-receiving half-section 200 includes a pair of vertical support members 216. Each vertical support member 216 includes an elongated vertical slot 218 having a rounded bottom surface. Vertical slots 218 are dimensioned to receive protrusions 120 formed on finger 118 of anvil half-section 100 (FIG. 21) when the anvil half-section 100 is supported on the cartridge-receiving half-section 200 during assembly. By positioning protrusion 120 within the vertical slots 218, anvil half-section 100 can be pivoted in a scissor-like manner with respect to the cartridge-receiving half-section 200 between the open and closed positions. In one embodiment, protrusions 120 have a teardrop profile. Alternatively, other protrusion configurations are envisioned.

Cartridge-receiving half-section 200 further includes a pair of generally cylindrical protrusions 220 disposed at the proximal end thereof and extending inwardly into U-shaped channel 208. Protrusions 220 are configured to be received within arcuate slots 516 defined in stationary housing 502 of disposable assembly 600 to facilitate engagement of disposable assembly 600 within cartridge-receiving half-section 200. Cartridge-receiving half-section 200 also includes a pair of opposed cut-out sections 222 configured to receive outwardly-extending serrated surfaces 518 of stationary housing 502. Serrated surfaces 518 provide a grippable surface to facilitate removal and/or replacement of disposable assembly 600 from channel member 206 of cartridge-receiving half-section 200. A pair of opposed openings 224 defined through the sidewalls of channel member 206 are configured to engage flared tabs 520 of stationary housing 502 to releasably secure disposable assembly 600 within cartridge-receiving half-section 200.

Figure 2B:
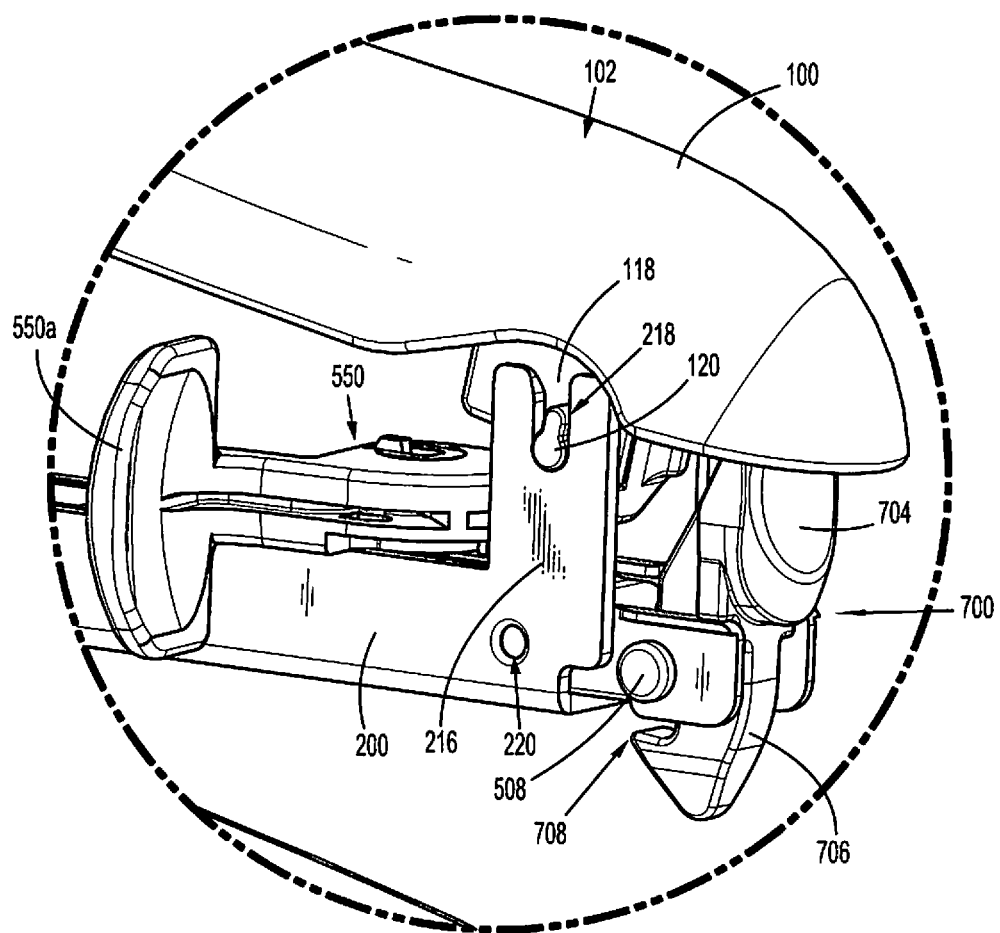
FIG. 2B is an enlarged view of the indicated area of detail shown in FIG. 2A.
Figure 27:
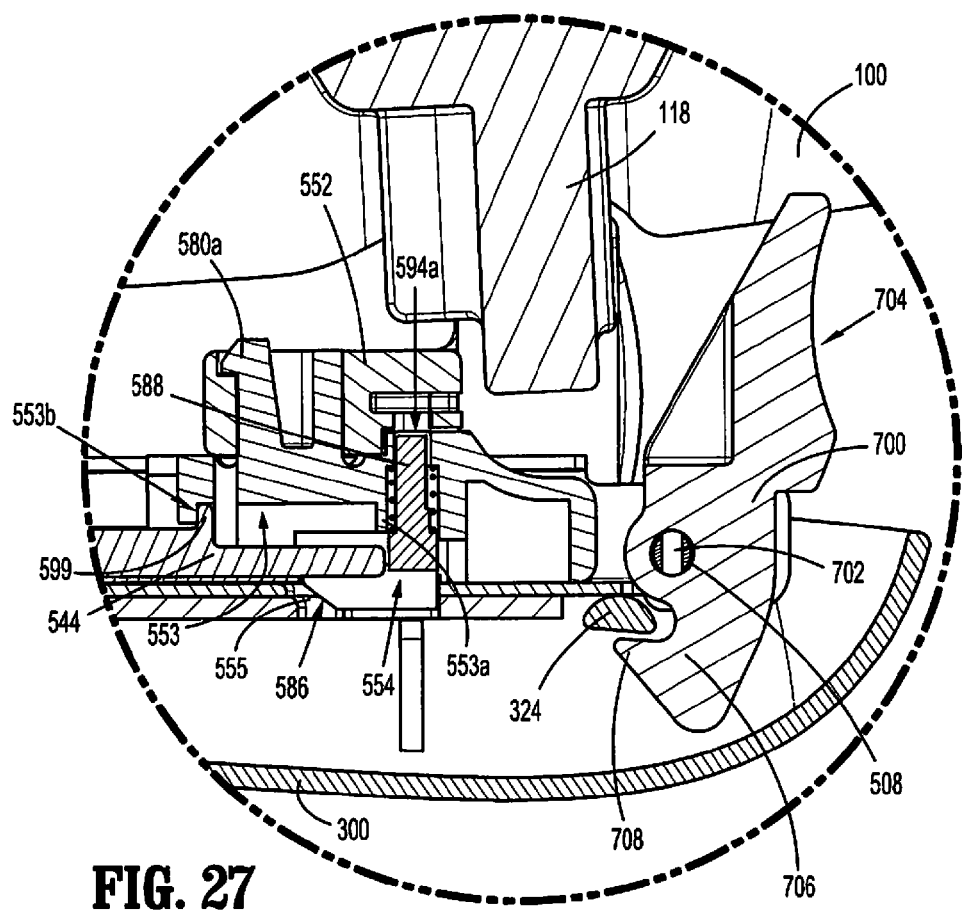
FIG. 27 is an enlarged view of the indicated area of detail shown in FIG. 25.

Clamping lever 300, as best shown in FIGS. 3 and 3A, includes a handle portion 306 including a grip 308 and a thumb engaging abutment 310. As discussed above, a pair of spaced flange portions 304 are supported on the distal end of clamping lever 300. Each flange portion 304 defines a cutout 302 dimensioned to receive a respective lateral support member 112 of anvil half-section 100 when stapler 10 is moved towards the clamped position (FIG. 2B). The distal end of clamping lever 300 also defines a pair of openings 312 which are dimensioned to receive a pivot member 314, e.g. a pin. Pivot member 314 is dimensioned to extend through openings 226 in cartridge-receiving half-section 200 and openings 312 in clamp lever 300 to pivotally secure clamp lever 300 to cartridge-receiving half-section 200. A spring member 316 includes a folded-under, T-shaped proximal end 318 that is engaged within opposed slots 320 defined within opposed side walls of clamping lever 300 and may be secured therein in any suitable fashion, e.g., mechanical engagement, welding, adhesion, etc. The distal end 322 of spring member 200 is configured to abut an undersurface of cartridge-receiving half-section 200 to bias clamping lever 300 apart from cartridge-receiving half-section 200, i.e., to bias clamping lever 300 towards the spaced-apart, or un-clamped position. Clamping lever 300 further includes an engagement member, e.g., semi-cylindrical post 324, which, as will be described in greater detail below, is configured to engage latch portion 706 of locking member 700 of firing unit 500 when clamp lever 300 is moved to the clamped position (FIG. 27). Although a semi-cylindrical post 324 is illustrated, other engagement member configurations are also envisioned.

Turning now to FIGS. 2C-3 and 8-12, disposable assembly 600 includes SULU 400 and firing unit 500 integrated with one another to form a single component, i.e., disposable assembly 600. More specifically, disposable assembly 600 includes a stationary housing 502 configured to house the working components of firing unit 500, which will be described below, and a distal extension 504 that is configured to engage and retain SULU 400 thereon, thus forming an integrated disposable assembly 600. Distal extension 504 of disposable assembly 600 extends distally from stationary housing 502.

Figure 12:
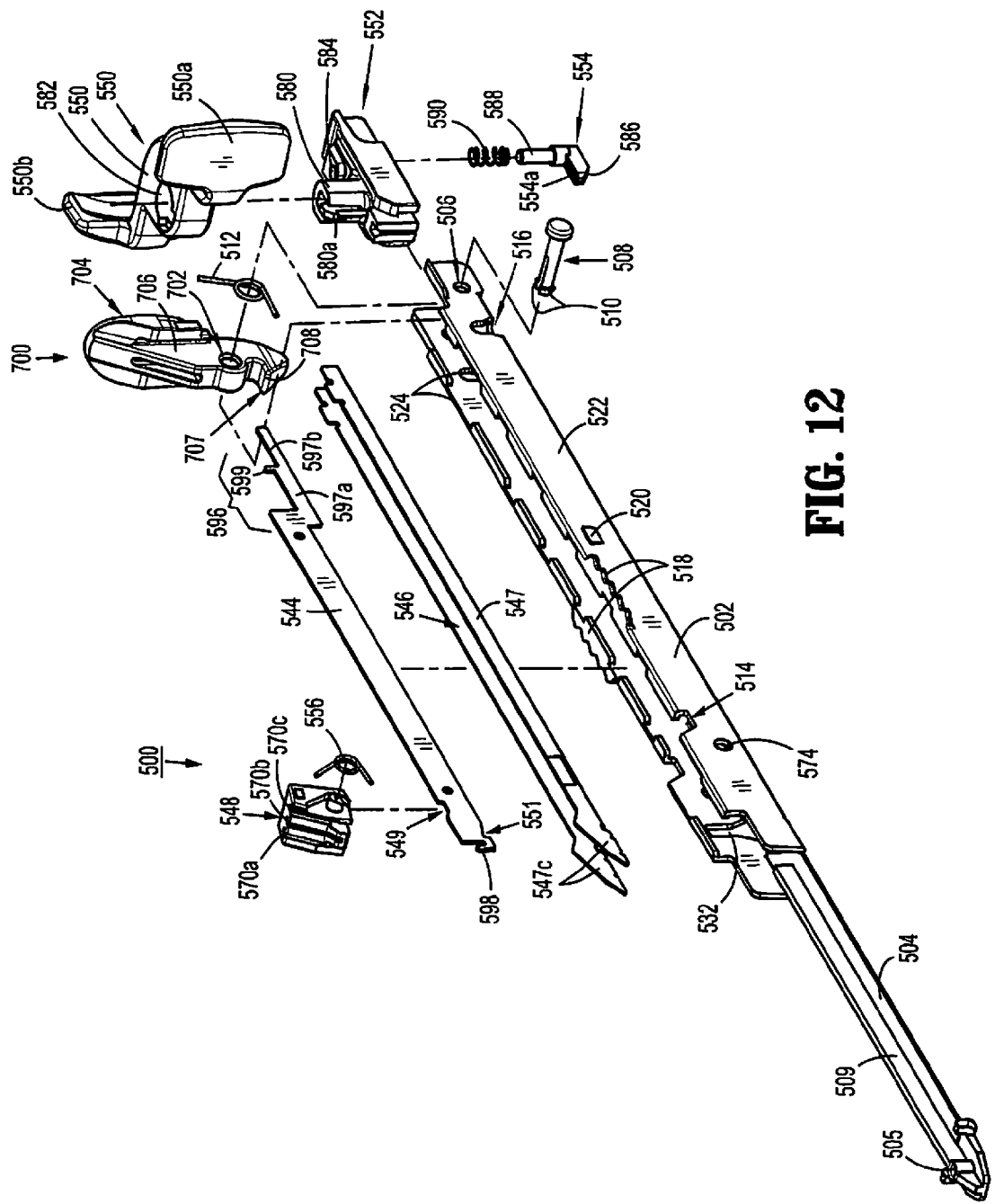
FIG. 12 is a side, perspective view of the disposable assembly absent the SULU shown in FIG. 10 with parts separated.

Stationary housing 502 includes a proximal end including opposed openings 506 (FIG. 2D) which receive pivot member 508 (FIG. 12). Pivot member 508 extends through openings 506 defined within each of the sidewalls of stationary housing 502 and through bore 702 defined transversely though locking member 700. Locking member 700 is pivotably coupled between sidewalls of stationary housing 502 adjacent the proximal end of firing unit 500 of disposable assembly 600. Pivot member 508 may include a bifurcated insertion end defining a pair of resilient locking tabs 510 (FIG. 12) such that, upon insertion of pivot member 508 through the first opening 506, bore 702, and out of the second opening 506, resilient locking tabs 510 bias outwardly to lock pivot member 508 in pivotable engagement therethrough.

Referring also to FIG. 12, locking member 700 includes a push-button 704 disposed on one side of pivot member 508 and a latch portion 706 including a hook member 708 disposed on the opposed side of pivot member 508. A biasing member 512 is positioned about pivot member 508 to urge latch portion 706 inwardly towards stationary housing 502 of disposable assembly 600, thus urging push-button 704 outwardly therefrom. Latch portion 706 extends downwardly beyond the proximal end of stationary housing 502 to a position below a bottom surface of channel member 206 (FIG. 20) such that hook member 708 of latch portion 706 is exposed. The exposed hook member 708 of locking member 700, facilitated by the bias of biasing member 512, is configured to engage semi-cylindrical post 324 (FIG. 3) of clamping lever 300 upon movement of clamping lever 300 to the clamped position, thereby locking clamping lever 300 in the clamped position. Push-button 704 is selectively depressible against the bias of spring 512 to disengage hook member 708 from post 324 to unlock clamping lever 300, this allowing clamping lever 300 to return under bias of spring 316 back to the open, or unclamped position.

Figure 2C:
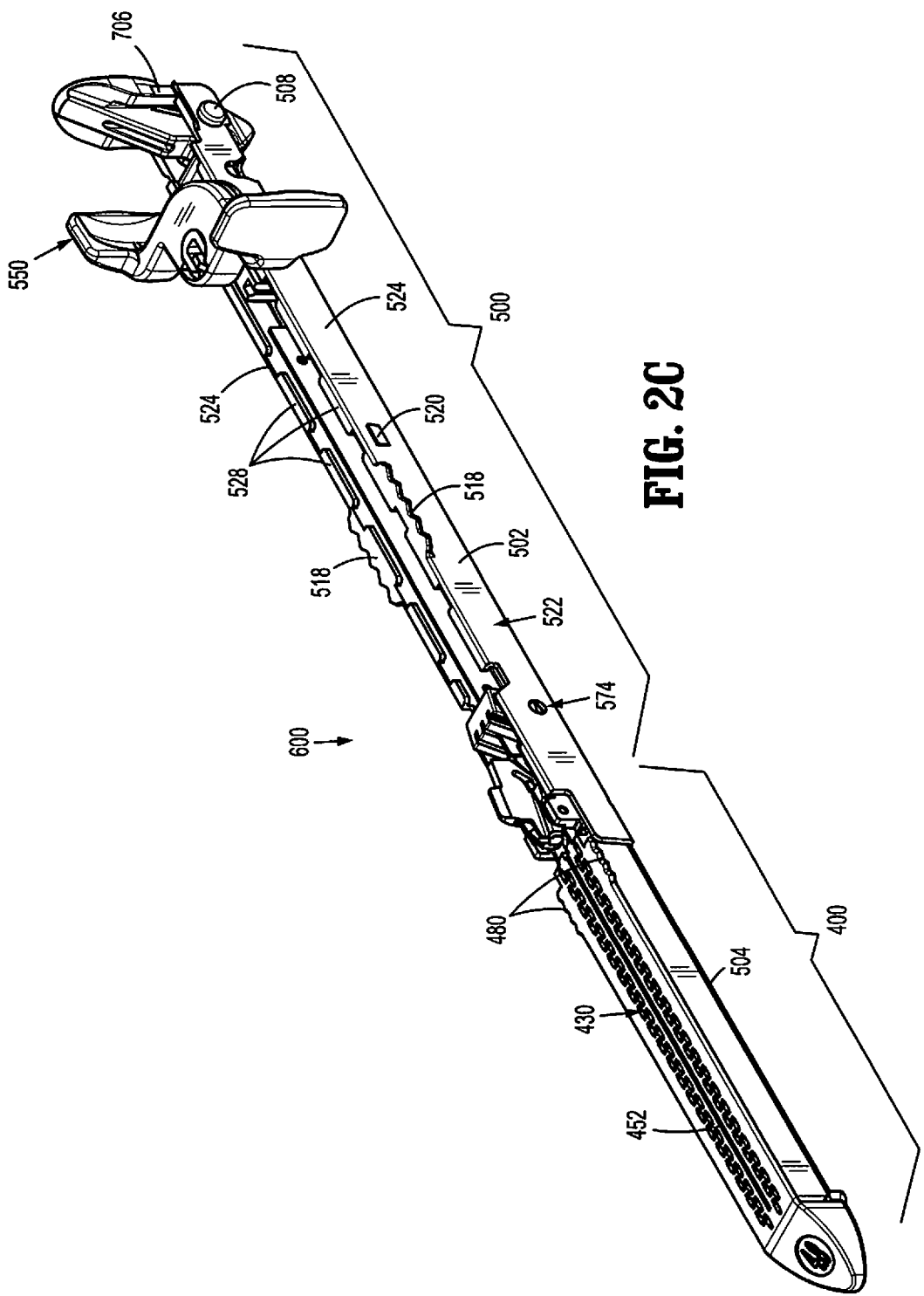
FIG. 2C is a side, perspective view of the disposable assembly of the surgical fastener applying apparatus shown in FIG. 1.
Figure 2D:
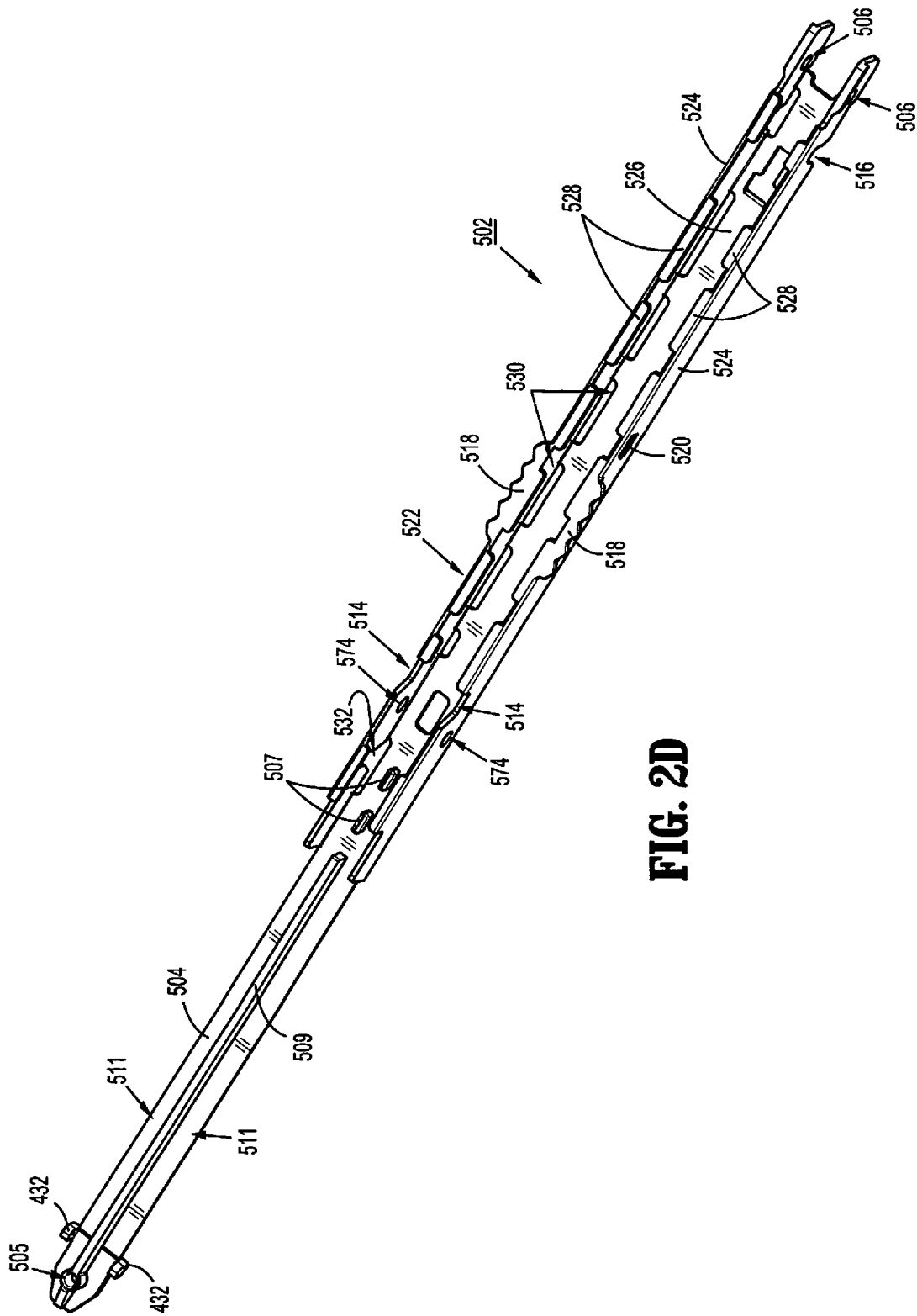
FIG. 2D is top, perspective view of the frame of the disposable assembly shown in FIG. 2C.

Referring to FIGS. 2D and 8-12, the components and features of firing unit 500 are described. Firing unit 500 is supported within stationary housing 502 of disposable assembly 600 and includes a knife actuating bar 544, a cam bar 546, a guide block 548, a firing lever 550, a slide block 552, a pedal 554 and the pivotal locking member 700 (FIG. 12). As shown in FIG. 2D, stationary housing 502 includes a U-shaped frame 522 including a pair of sidewalls 524 and a bottom wall 526 which extends distally beyond sidewalls 524 to form distal extension 504. Sidewalls 524 each include a plurality of spaced-apart, inwardly-extending tabs 528 disposed along the free ends thereof and bottom wall 526 includes a plurality of spaced-apart slots 530 defined therethrough adjacent each of sidewalls 524, each of which is positioned to oppose one of the tabs 530. This slotted and tabbed configuration of frame 522 of stationary housing 502 provides increased flexibility and resiliency to stationary housing 502, thus facilitating insertion and removal of disposable assembly 600 from cartridge-receiving half-section 200 and engagement of disposable assembly 600 within cartridge-receiving half-section 200 (FIG. 9A), e.g., facilitating pinching, or squeezing of serrated surfaces 518 of stationary housing 502 to insert and/or remove stationary housing 502 from cartridge-receiving half-section 200. The distal-most tabs 528 of stationary housing 502 may also be configured to engage the proximal end of SULU 400 to facilitate the engagement of SULU 400 on distal extension 504. As mentioned above, stationary housing 502 is configured for releasable engagement within U-shaped channel 208 of cartridge-receiving half-section 200 via the engagement of flared tabs 520 of stationary housing 502 within opposed openings 224 of cartridge-receiving half-section 200 (FIG. 4) and protrusions 220 of cartridge-receiving half-section 200 within arcuate slots 516 of stationary housing 502 (FIG. 3). More specifically, flared tabs 520 are configured to bias into engagement within opposed openings 224 upon insertion of stationary housing 502 into cartridge-receiving half-section 200. Sidewalls 524 may be squeezed inwardly to facilitate such insertion of stationary housing 502 within cartridge-receiving half-section 200. In order to remove stationary housing 502 from cartridge-receiving half-section 200, sidewalls 524 of stationary housing 502 may be squeezed, or pinched toward one another (e.g., via grasping and squeezing serrated surfaces 518 toward one another) to facilitate retraction of flared tabs 520 from openings 224, thus permitting withdrawal of stationary housing 502 from cartridge-receiving half-section 200. To this end, stationary housing 502 may be formed from a plastic, or other suitable material capable of resiliently flexing to facilitate engagement and disengagement of stationary housing 502 within cartridge-receiving half-section 200, One (or both) of the sidewalls 524 of stationary housing 502 includes a bottleneck opening 532 defined therethrough that is configured to receive resilient finger 230 (FIGS. 9B-9C) of cartridge-receiving half-section 200, to ensure engagement between disposable assembly 600 and cartridge-receiving half-section 200.

With reference to FIGS. 1-3 and 8-12, the distal ends of sidewalls 524 each define a notch 514 having an angled distal surface. Notches 514 are configured to receive extensions 110 of anvil half-section 100, as mentioned above, to ensure proper alignment between SULU 400 and staple deforming portion 106 when surgical stapler 10 is moved to the clamped position. Each sidewall 524 also includes an outwardly extending serrated surface 518 that is positionable within the opposed cut-out sections 222 of cartridge-receiving half-section 200 to facilitate gripping and squeezing of the disposable assembly 600 to allow for removal and/or replacement of disposable assembly 600 from channel member 206 of cartridge-receiving half-section 200 and to ensure a substantially flush-fit of disposable assembly 600 within cartridge-receiving half-section 200, i.e., such that serrated surfaces 518 are substantially flush with the free ends of channel member 206 of cartridge-receiving half-section 200.

Figure 19:
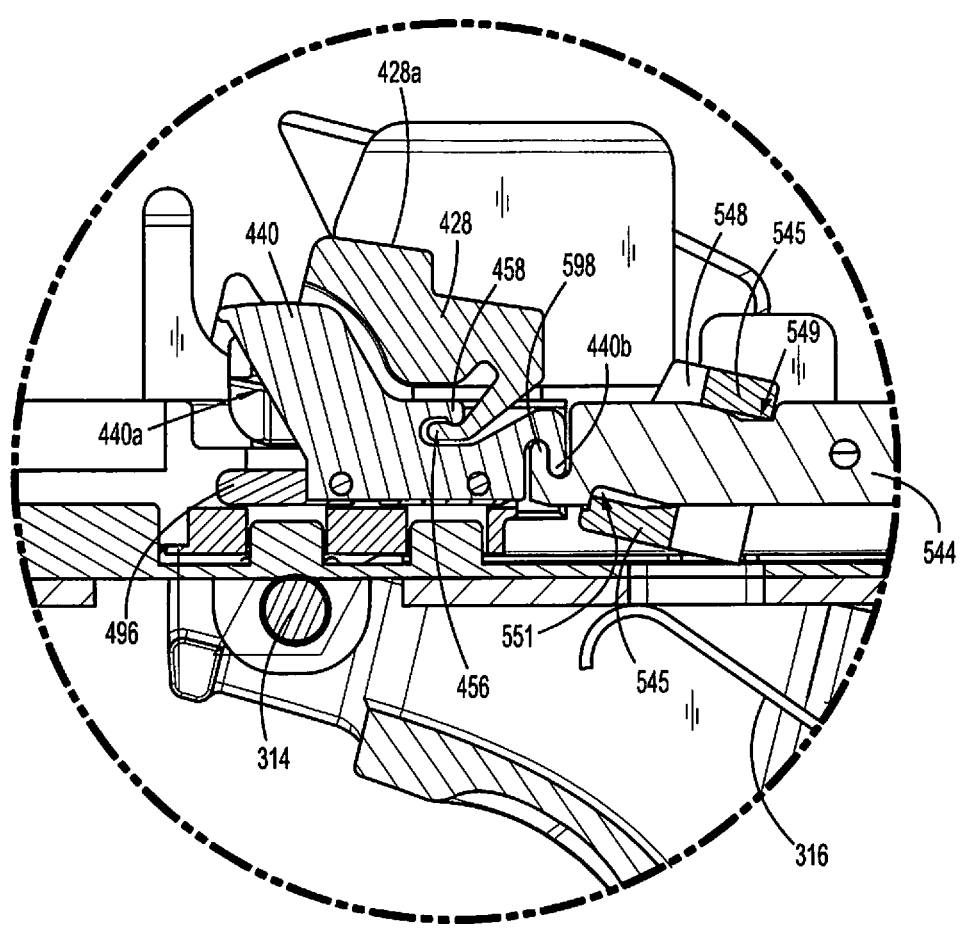
FIG. 19 is an enlarged view of the indicated area of detail shown in FIG. 18.

Guide block 548 includes a body defining three longitudinal slots 570a-c and a pair of outwardly extending protrusions 572. In one embodiment, each protrusion 572 is substantially cylindrical and includes a tapered portion (FIG. 9). Alternatively, other protrusion configurations are envisioned. Protrusions 572 are dimensioned to be received in openings 574 (FIG. 12) formed in sidewalls 524 of stationary housing 502 to axially fix guide block 548 within the distal end of stationary housing 502. Protrusions 572 allow for a degree of pivotal movement of guide block 548 within U-shaped frame 522. As will be discussed in further detail below, guide block 548 is pivotal from the first position (FIG. 19) in locking engagement with notches 549 and 551 of knife actuating bar 544 to the second position (FIG. 26) disengaged from notches 549 and 551 of knife actuating bar 544 in response to movement of stapler 10 to the clamped position. More specifically, as anvil half-section 100 is approximated relative to cartridge-receiving half-section 200 to achieve the clamped position, extensions 110 of anvil half-section 100 urge guide block 548 to pivot from the first position (FIG. 19) to the second position (FIG. 26) to disengage the lockout mechanism. A torsion spring 556 is disposed about one or both of the protrusions 572 to urge guide block 548 into locking engagement with notches 549 and 551, i.e., to bias guide block 548 into the first, locked position (FIG. 19). Each of slots 570a and 570c is dimensioned to slidably receive a respective sidewall 547 of cam bar 546. Similarly, slot 570b is dimensioned to slidably receive knife actuating bar 544.

Figure 20:
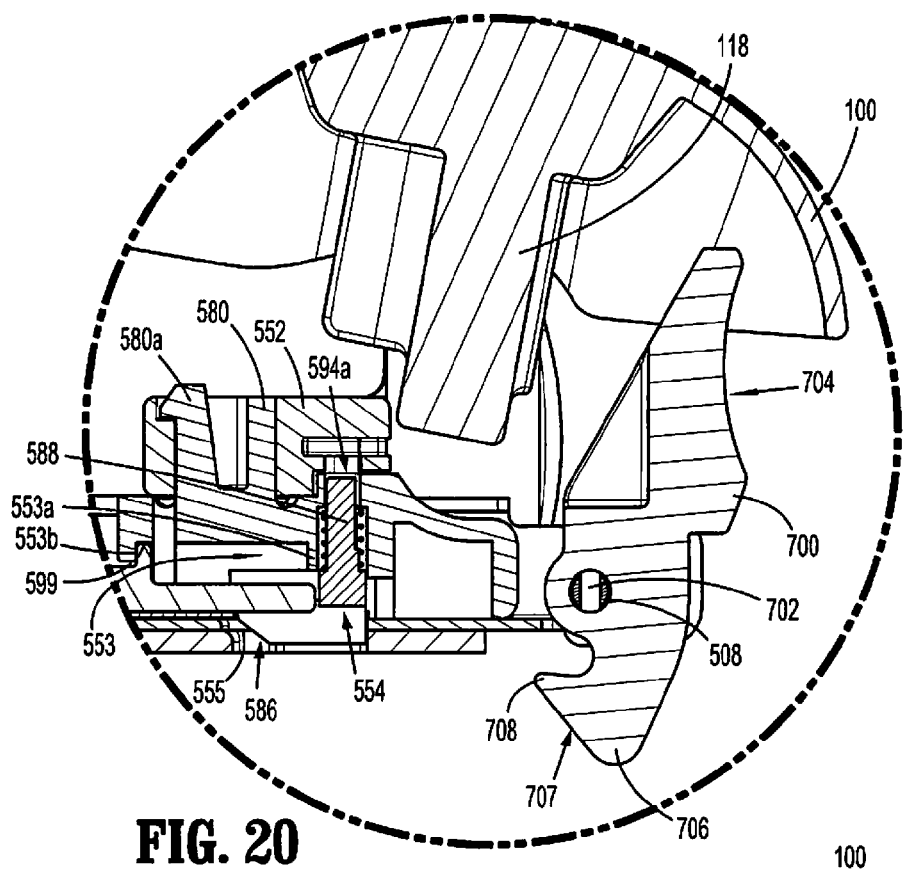
FIG. 20 is an enlarged view of the indicated area of detail shown in FIG. 18.
Figure 21:
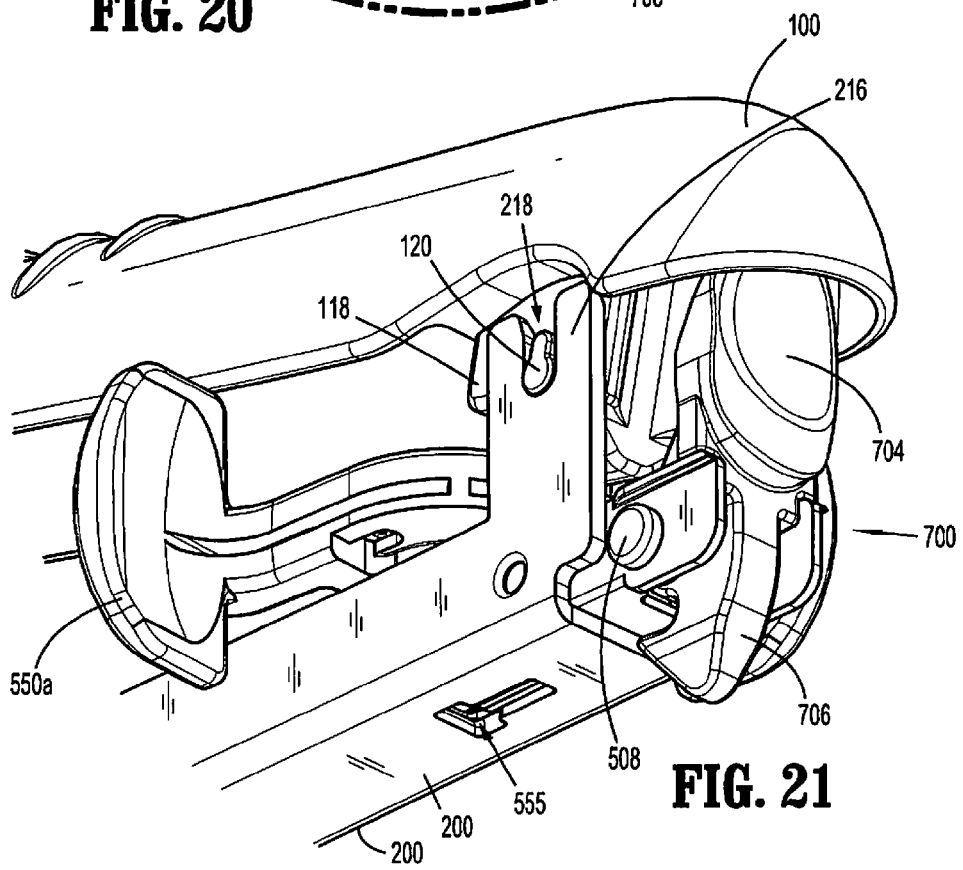
FIG. 21 is a perspective view of the proximal end of the surgical fastener applying apparatus shown in FIG. 18 in the open position.
Figure 25:
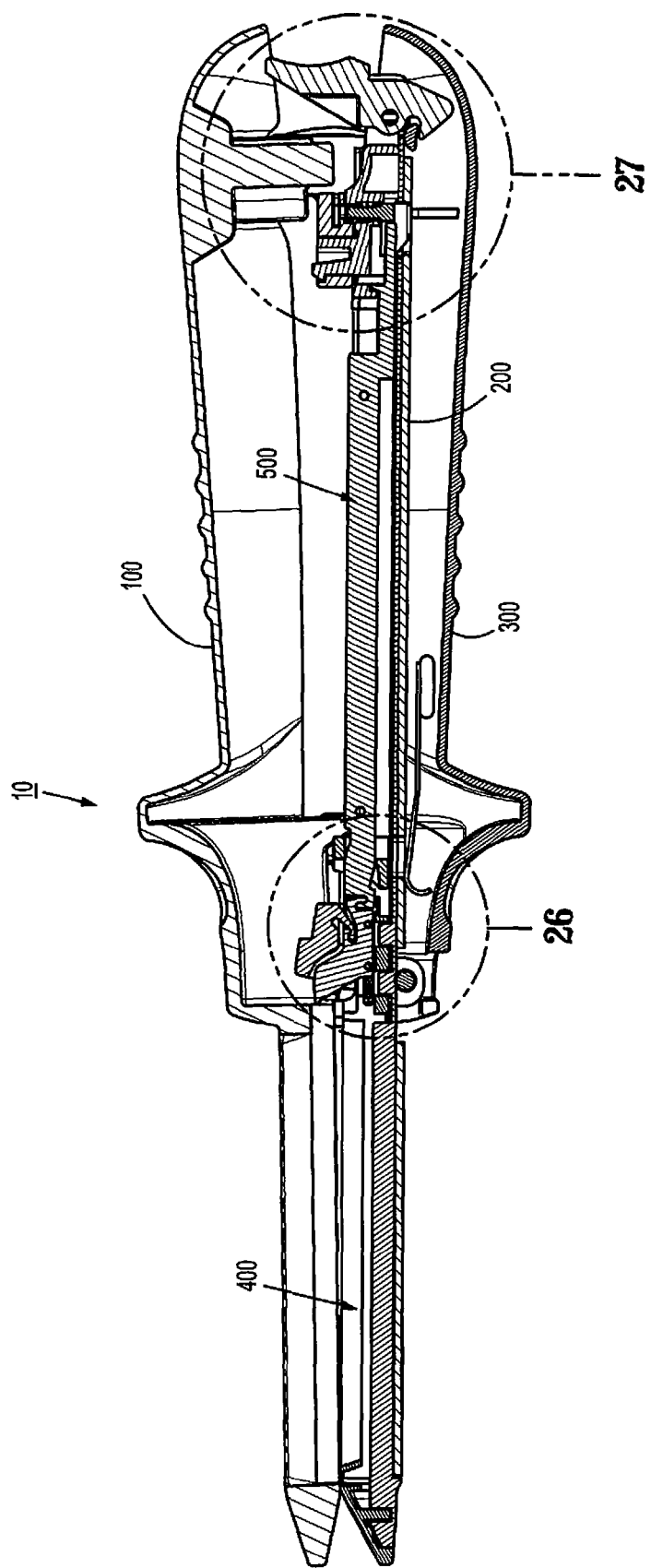
FIG. 25 is a side, cross-sectional view of the surgical fastener applying apparatus shown in FIG. 24 in the clamped position.

Referring to FIGS. 8-17, slide block 552 includes a hub 580 which includes a resilient finger 580a configured to be snap-fit into a pivot hole 582 formed in firing lever 550. Firing lever 550 is pivotal about hub 580 when the slide block 552 is in a retracted position to facilitate actuation of the firing unit 500 from either side of stapler 10. Pedal 554 is reciprocally received within a hole 584 formed in slide block 552. Pedal 554 includes a split body portion 554a which is configured to straddle a proximal end 558 of knife actuating bar 544. In one embodiment, split body portion 554a includes an angled distal surface 586. A pin 588 extends upwardly from pedal 554 through hole 584 in slide block 552. A biasing member 590 is positioned between split body portion 554a and slide block 552, about pin 588 to urge pedal 554 downwardly away from slide block 552 to an extended position. In the retracted position of slide block 552, pedal 554 is received in a cutout 555 formed in a bottom wall of channel member 206 (FIG. 20).

Figure 30:
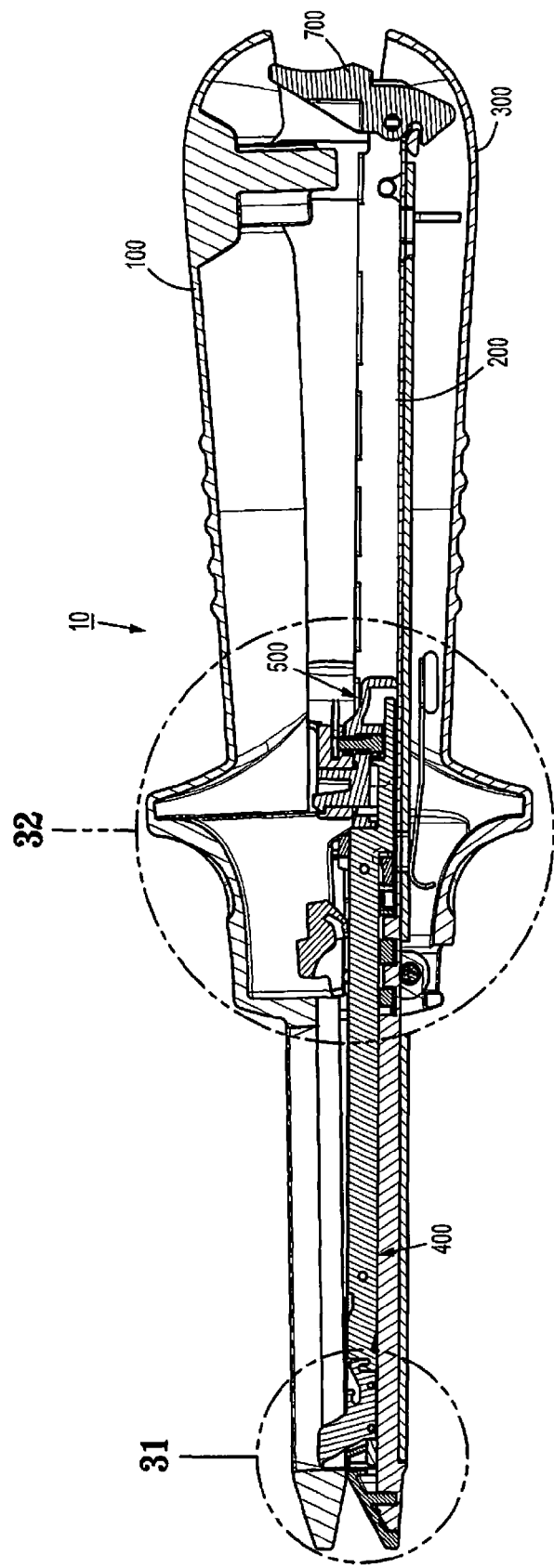
FIG. 30 is a side, cross-sectional view of the surgical fastener applying apparatus shown in FIG. 29 with the firing unit in the actuated position.

Firing lever 550, as best shown in FIGS. 2C, 3 and 20-24, includes first and second finger engagement members 550a and 550b, either one of which can be selectively engaged to move the firing lever 550 through a firing stroke from either side of stapler 10. An arcuate recess 594 (FIG. 12B) is formed in a bottom surface of firing lever 550 which slidably receives pin 588 of pedal 554 to define the range of rotation through which firing lever 550 can pivot about hub 580 of slide block 552. As used herein, a firing stroke is defined as movement of firing lever 550 from a fully retracted position (FIG. 25) to a fully advanced position (FIG. 30). A stop recess 594a is formed at each end of arcuate recess 594. Stop recesses 594a are configured and dimensioned to receive the end of pin 588 of pedal 554 to prevent pivotal movement of firing lever 550 about hub 580 during a firing stroke of surgical stapler 10. More specifically, when the firing unit 500 is actuated to advance slide block 552 distally within stationary housing 502, angled distal surface 586 of pedal 554 engages channel member 206 and is cammed out of cutout 555 (FIG. 27) to urge pin 588 upwardly into a stop recess 594a to prevent pivotal movement of firing lever 550 during movement of firing lever 550 through a firing stroke. As is evident, pin 588 must be positioned beneath a stop recess 594a to allow pedal 554 to lift upwardly from cutout 555 to allow firing lever 550 to be moved through the firing stroke. Thus, firing lever 550 must be pivoted to one side or the other of firing unit 500 before the firing lever 550 can be moved through a firing stroke.

Knife actuating bar 544 includes a proximal end having a stepped portion 596 which includes a proximal first step 597a having a first height and a second step 597b having a second height which is greater than the first height (FIG. 12). A distal end of actuating bar 544 includes an upturned hook portion 598 and upper and lower notches 549 and 551. A finger 599 projects upwardly from knife actuating bar 544 between first and second steps 597a and 597b. As shown in FIG. 27, finger 599 is slidably received within a recess 553 formed in an underside of slide block 352. When slide block 552 is advanced distally within stationary housing 502, finger 599 moves within recess 553 such that slide block 552 moves in relation to knife actuating bar 544 until finger 599 engages a wall 553a defining the proximal end of recess 553. When finger 599 engages wall 553a, further distal movement of slide block 552 will also effect distal movement of knife actuating bar 544. As will be evident below, this arrangement allows for staples to be ejected from SULU 400 prior to cutting of tissue.

Figure 12A:
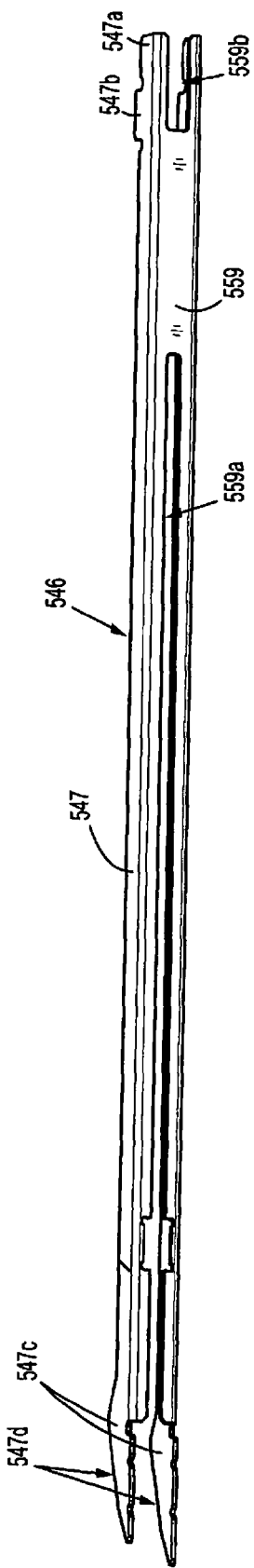
FIG. 12a is a bottom, perspective view of the cam bar of the firing unit of the disposable assembly shown in FIG. 12.
Figure 12B:
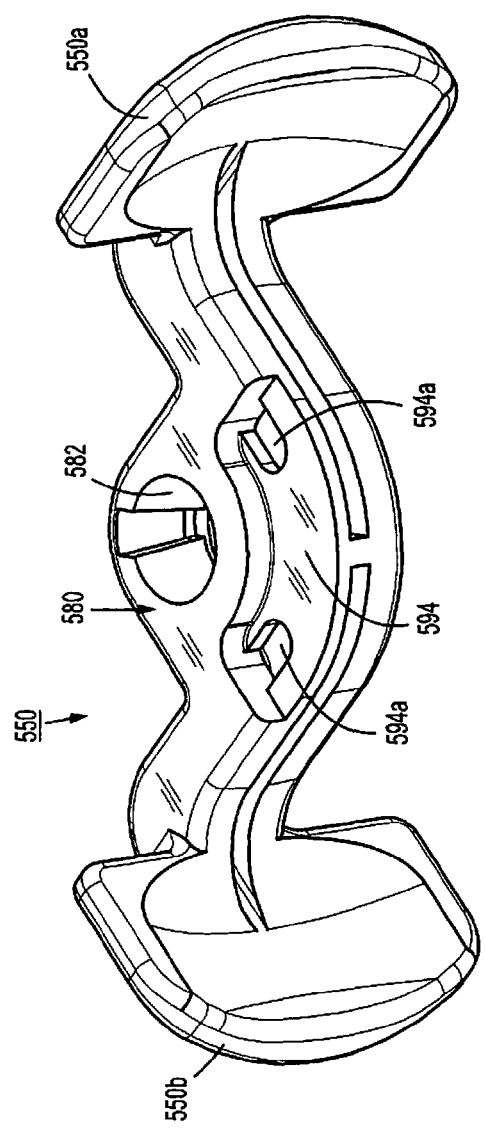
FIG. 12b is a bottom, perspective view of the firing lever of the firing unit of the disposable assembly shown in FIG. 12.
Figure 16:
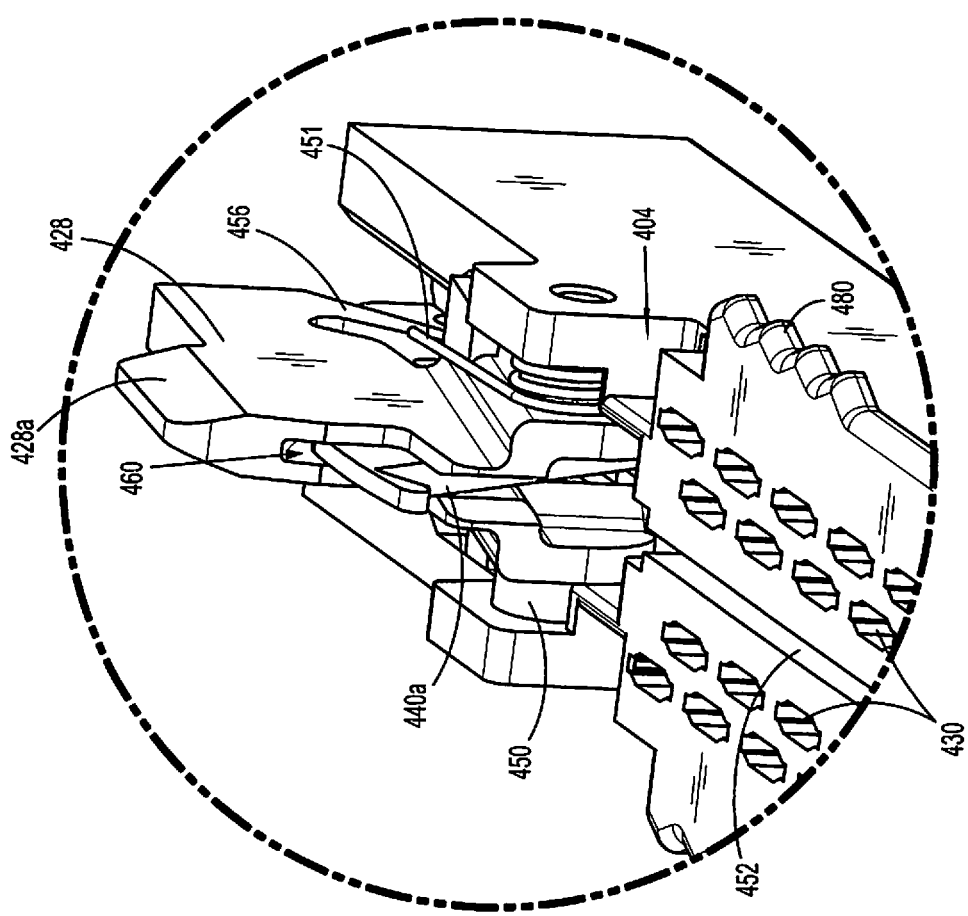
FIG. 16 is an enlarged view of the indicated area of detail shown in FIG. 15.
Figure 15:
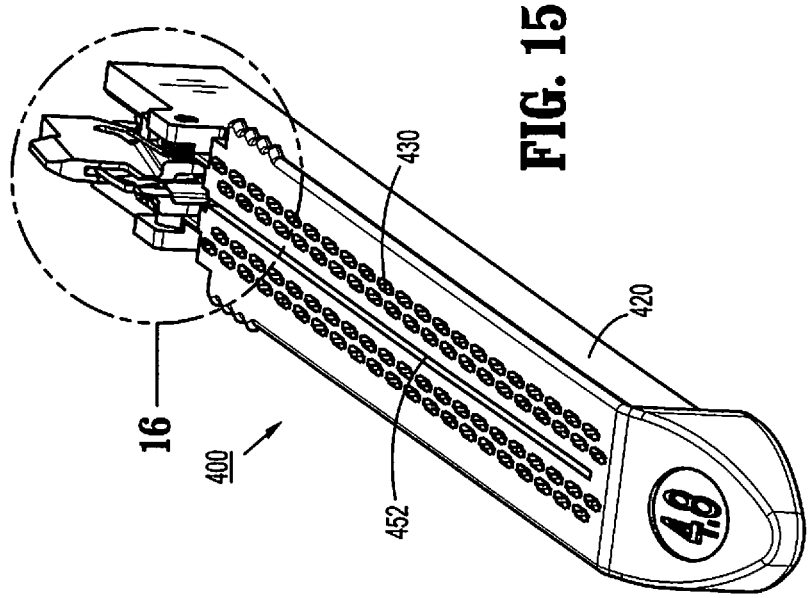
FIG. 15 is a front, perspective view of the SULU shown in FIG. 13.

Referring to FIGS. 12 and 12A, cam bar 546 includes a pair of sidewalls 547 and a base wall 559. The proximal end 547a of each sidewall 547 includes a raised wall portion 547b. Each raised wall portion 547b is configured to be fixedly received in a slot (not shown) formed in an underside of slide block 552 to fixedly secure the proximal end of cam bar 546 to slide block 552. Alternately, slide block 552 may be molded about the proximal end of cam bar 546. The distal end 547c of each sidewall 547 includes an angled camming surface 547d. Base wall 559 defines a distally extending elongated slot 559a (FIG. 12A) which extends from the distal end of cam bar 546 along a substantial length of the cam bar 546 and a proximally extending longitudinal slot 559b. Slot 559b is positioned to facilitate the passage of pedal 554 through cutout 555 of channel member 206 when slide block 552 is in the retracted position (see FIG. 27).

Sidewalls 547 of cam bar 546 are slidably positioned in slots 570a and 570c of guide block 548 and knife actuating bar 544 is slidably positioned in longitudinal slot 570b of guide block 548. When firing unit 500 is supported in channel member 206 and firing lever 550 is pivoted to one side of stationary housing 502 and pushed distally, slide block 552 is moved distally within stationary housing 502. As slide block 552 begins to move distally, tapered surface 586 of pedal 554 engages a proximal edge of channel member 206 defining cutout 555 to urge pedal 554 upwardly out of cutout 555, through slot 559b of cam bar 546, and onto an inner surface of stationary housing 502 of disposable assembly 600 (FIG. 27). As this occurs, pin 588 of pedal 554 moves into a stop recess 594a to prevent further pivotal movement of firing lever 550. If firing lever 550 is not pivoted to a position in which pin 588 is positioned beneath a stop recess 594a, pedal 554 will be prevented from moving upwardly out of cutout 555 and firing lever 550 will be prevented from moving through a firing stroke. As firing lever 550 is moved distally, finger 599 moves within recess 553 such that knife actuating bar 544 remains stationary as cam bar 546 is advanced distally. When finger 599 engages proximal wall 553a defining recess 553, knife actuating bar 544 is moved distally with slide block 552 and cam bar 546. As will be discussed below, when cam bar 546 and knife actuating bar 544 are moved distally within stationary housing 502 of disposable assembly 600 and channel member 206, angled camming surfaces 547d of cam bar 546 are moved through SULU 400 to eject staples 402 from SULU 400. Simultaneously, although with a preset delay equal to the length of recess 553 (FIG. 32), knife actuating bar 544 drives a knife blade 540 through SULU 400 to dissect tissue.

Figure 2E:
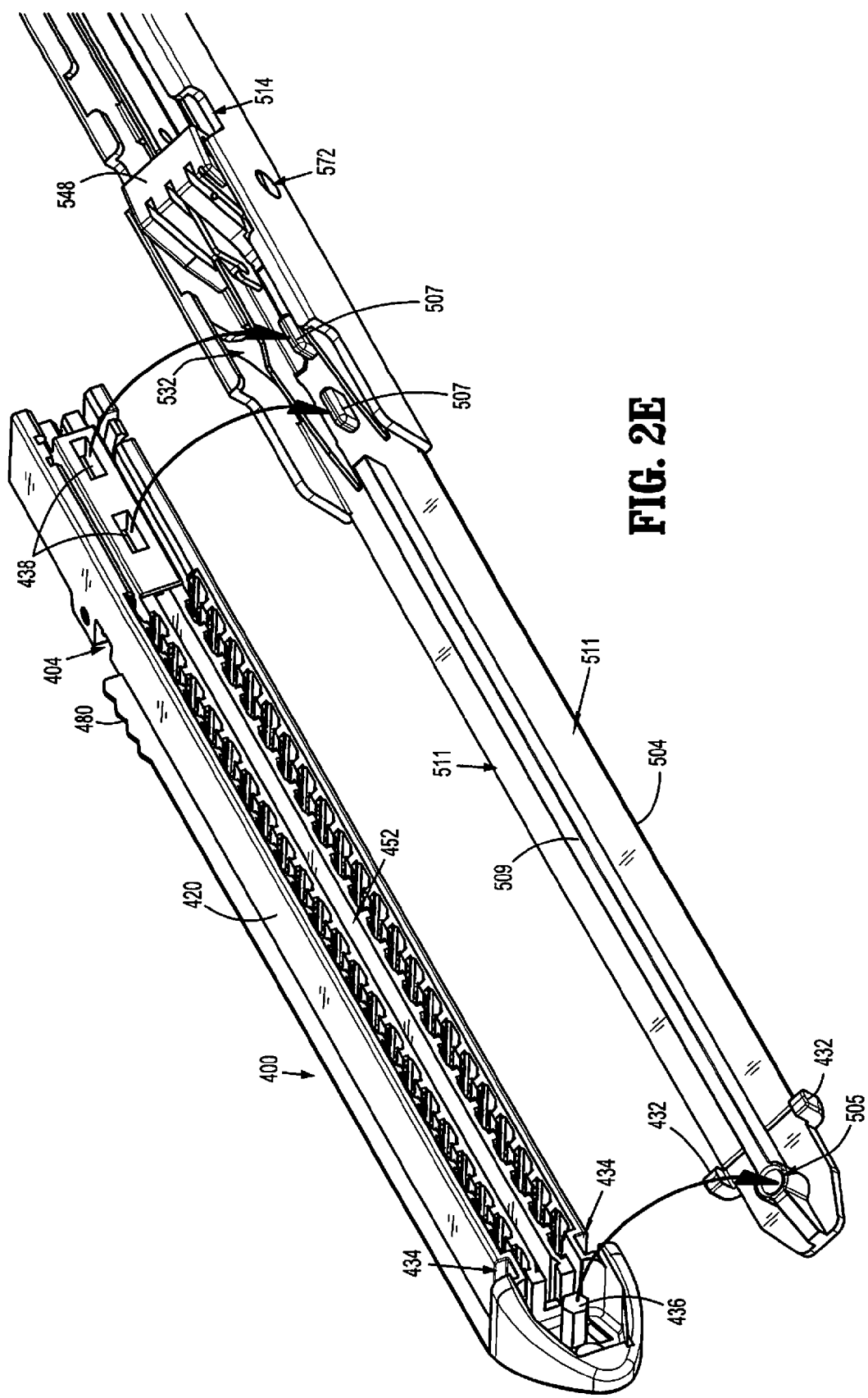
FIG. 2E is a top, perspective view of the distal portion of the disposable assembly shown in FIG. 2C with the SULU separated from the frame of the disposable assembly.
Figure 2F:
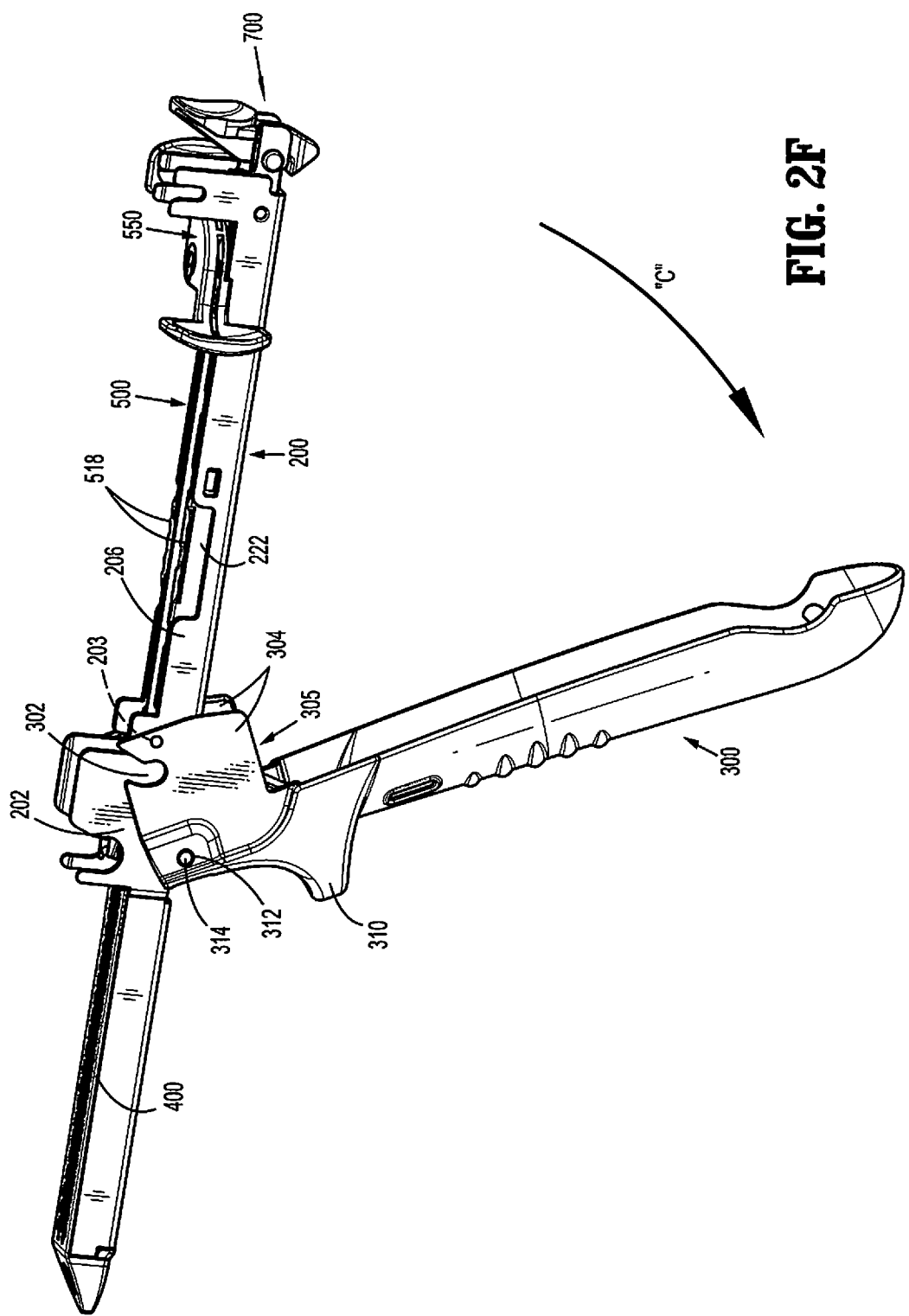
FIG. 2F is a side, perspective view of the cartridge receiving half-section of the surgical fastener applying apparatus shown in FIG. 1 with the handle in the open position.

Distal extension 504 of stationary housing 502, as mentioned above, is configured to engage and retain SULU 400 thereon to form the integrated disposable assembly 600. As best shown in FIGS. 2C-2E, distal extension 504 engages SULU 400 to enclose the underside of cartridge body 420 of SULU 400, e.g., distal extension 504 forms the bottom cover of cartridge body 420 of SULU 400. More specifically, a pair of cantilever arms 432 extending from opposed sides of distal extension 504 engage cutouts 434 formed at the distal end of cartridge body 420 of SULU 400; a central lumen 505 defined towards the distal end of distal extension 504 receives a post 436 extending from the distal tip portion of cartridge body 420; proximal protrusions 507 extending from the proximal end of distal extension 504 are received within corresponding slots 438 defined within the proximal portion of SULU 400; and the distal-most tabs 528 of sidewalls 524 of stationary housing 502 are engaged about the proximal end of SULU 400 to engage SULU 400 and distal extension 504 of firing unit 500 to one another. Thus, SULU 400 is fixedly secured to distal extension 504 via a snap-fit engagement and a male-female connection at both the distal end of SULU 400 and at the proximal end of SULU 400. That is, the engagement, e.g., snap-fit engagement, of cantilever arms 432 within cutouts 434 retains post 436 within central lumen 505 at the distal end of SULU 400, while the engagement, e.g., snap-fit engagement, of distal-most tabs 528 of sidewalls 524 about the proximal end of SULU 400 retains proximal protrusions 507 within slots 438 at the proximal end of SULU 400. Further, these engagements may be further facilitated by friction fitting, e.g., post 436 may be frictionally retained within lumen 505 and/or proximal protrusions 507 may be frictionally retained within slots 438 and/or in any other suitable fashion, e.g., gluing or adhesion, ultrasonic or other suitable welding process, heat staking, etc. Distal extension 504 of firing unit 500 further includes a longitudinal ridge 509 formed on an upper surface thereof that is received within cartridge body 420 of SULU 400, the importance of which will be described below.

Referring to FIGS. 13-17, SULU 400 is described. SULU 400 includes cartridge body 420, a plurality of staple pushers 422 (only one is shown), a knife 440 having an angled sharpened leading edge or blade 440a, a plurality of staples 402 (only one is shown), and a pivotally mounted safety lockout 428. Body 420 has a plurality of rows of staple retaining slots 430, e.g., four, six, etc. and a linear slotted knife track 452 centrally disposed in body 420. Knife 440 includes a downturned hook portion 440b which is positioned to engage upturned hook portion 598 (FIG. 12) of knife actuating bar 544 of firing unit 500. In the illustrated embodiment, body 420 includes two staggered rows of slots 430 formed on either side of linear slotted knife track 452. The staggered rows of slots 430 extend beyond the distal end of knife track 452 to facilitate staple formation beyond the distal end of the stroke of the knife blade 440a, although other configurations are contemplated.

Figure 17:
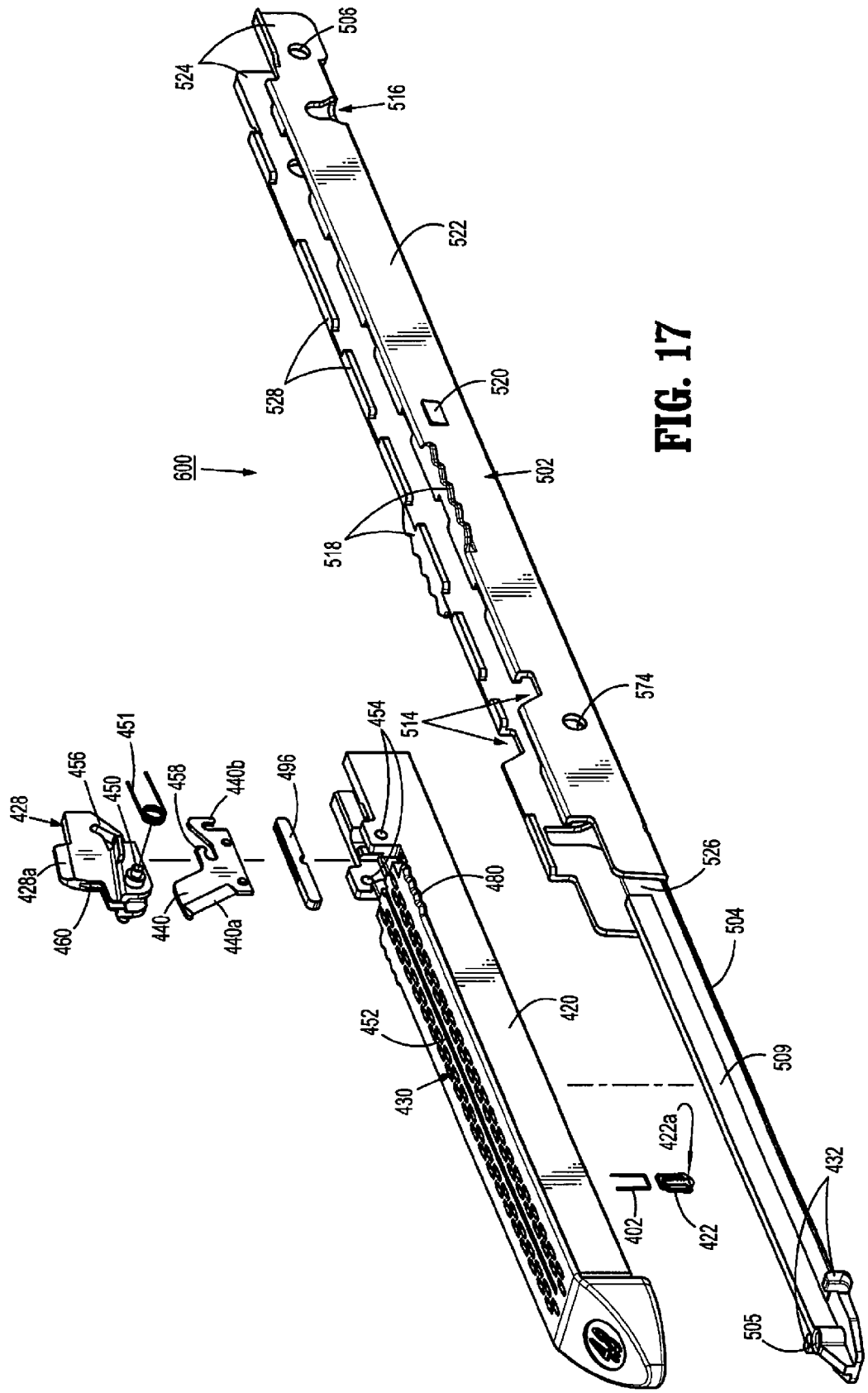
FIG. 17 is a side, perspective view with parts separated of the disposable assembly shown in FIG. 2C (absent the firing unit)
Figure 18:
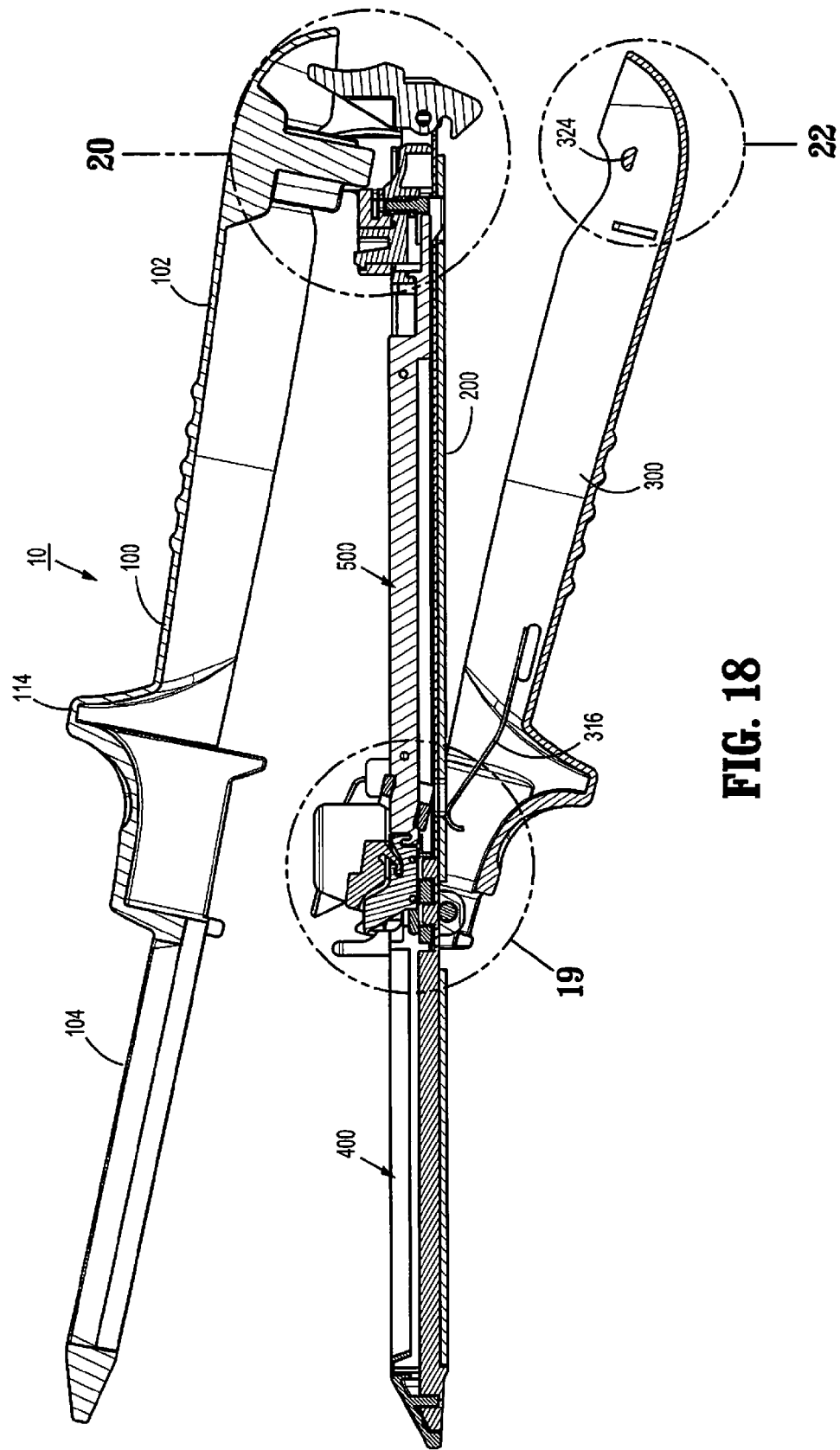
FIG. 18 is a side, cross-sectional view of the surgical fastener applying apparatus shown in FIG. 1 in the open position.

Staple pushers 422 may be configured to extend into one or more slots 430. In one embodiment, a single pusher is associated with each slot 430. Alternatively, as illustrated in FIG. 17, each pusher 422 can be configured to extend into two adjacent slots 430 and is positioned beneath respective staples 402 which are retained in slots 430. Further, each pusher 422 includes a lower cam surface 422a which is positioned to engage one of cam surfaces 547d (FIGS. 12, 12A) on the distal end of cam bar 546 such that movement of cam bar 546 through SULU 400 sequentially lifts each respective pusher 422 within its respective slot or slots 430 to eject staples from slots 430.

Longitudinal ridge 509 of distal extension 504 (FIG. 2E), as mentioned above, is received within cartridge body 420 of SULU 400. Longitudinal ridge 509 provides a bearing surface for a knife supporting member 496 (FIG. 17), which is secured to a bottom edge of knife 440. Knife 440 may be secured to supporting member 496 via pins, welding or other known fastening techniques. During a firing stroke, as will be described below, knife 440 is guided along knife track 452 as the firing lever 550 is advanced through channel member 206. A pair of slots 511 (FIG. 2D) are defined between the sides of ridge 509 and an outer wall of cartridge body 420. Longitudinal ridge 509 is positioned within body 420 and dimensioned to be slidably received within slot 559a (FIG. 12A) of cam bar 446 such that cam bar 446 is slidably movable through cartridge body 420 about longitudinal ridge 509 to eject staples 402 from SULU 400.

A proximal end of SULU 400 includes opposed, outwardly extending serrated surfaces 480 (FIG. 7) to facilitate gripping of the proximal end of SULU 400 to allow for removal and/or replacement of disposable assembly 600 from channel member 206 of cartridge-receiving half-section 200. Thus, removal and/or replacement of disposable assembly 600 may be effectuated by grasping either or both of serrated surfaces 480 of SULU 400 and serrated surfaces 518 of stationary housing 502.

Figure 34:
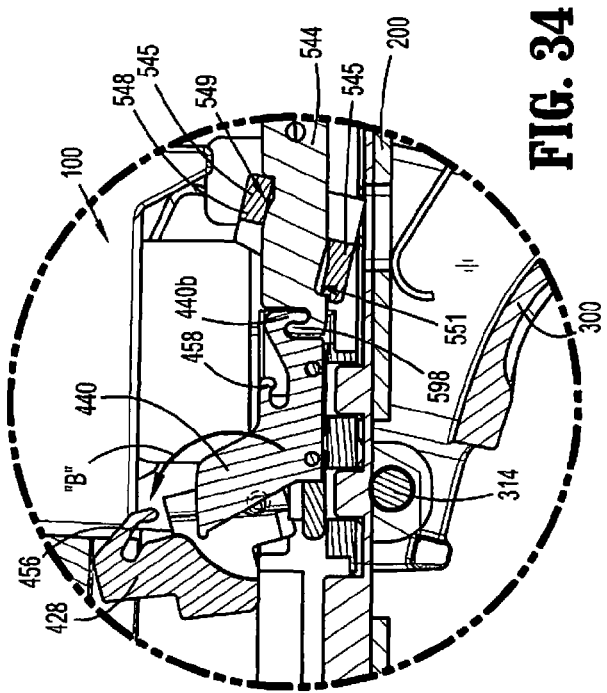
FIG. 34 is an enlarged view of the indicated area of detail shown in FIG. 33.

Referring to FIGS. 13-17, safety lockout 428 is pivotally disposed on an upper proximal end of body 420 and is pivotal about a pivot member 450 from a locked orientation (FIG. 26) to unlocked orientation (FIG. 34). Pivot member 450 is received in openings 454 in body 420. A biasing member, e.g., spring 451, is positioned between knife supporting member 496 and safety lockout 428 to urge safety lockout 428 towards the unlocked orientation. Safety lockout 428 includes a proximal hook 456 which is positioned to receive an engagement member 458 formed on the knife 440 to retain the safety lockout 428 in the locked orientation when the knife 440 is in the retracted position (FIG. 19). When the knife 440 is moved towards the advanced position during a firing stroke, engagement member 458 is moved away from proximal hook 456 to allow safety lockout 428 to pivot towards the unlocked position in response to the urging of spring 451. It is noted that safety lockout 428 is prevented from pivoting to the unlocked position when the anvil half-section 100 and cartridge-receiving half-section 200 are in the clamped position because the top surface 428a of safety lockout 428 engages an inner surface of anvil half-section 100 to prevent pivoting of safety lockout 428. Safety lockout 428 defines a slot 460 dimensioned to slidably receive the knife 440. In the retracted position of the knife 440, the leading edge 440a of knife 440 is confined within slot 460 of safety lockout 428 to prevent accidental engagement and injury to medical personnel with leading edge 440a of knife 440.

The assembly and operation of surgical stapler 10 is now described with reference to FIGS. 1-34. Initially, disposable assembly 600 is engaged within cartridge-receiving half-section 200. In order to engage disposable assembly 600 within cartridge-receiving half-section 200, disposable assembly 600, which includes SULU 400 and firing unit 500, is generally aligned above cartridge-receiving half-section 200 and is inserted into U-shaped channel 208 of channel member 206. More specifically, disposable assembly 600 is aligned with cartridge-receiving half-section 200 such that, upon translation of disposable assembly 600 into U-shaped channel 208 of channel member 206, protrusions 220 are engaged within arcuate slots 516, flared tabs 520 are engaged within opposed openings 224, and resilient finger 230 is engaged within bottleneck opening 532, thus releasably engaging disposable assembly 600 within cartridge-receiving half-section 200. Installation of disposable assembly 600 may be facilitated, as discussed above, by grasping serrated surfaces 518 of stationary housing 502 (and, in particular, by grasping and squeezing serrated surfaces 518 inwardly) and/or by grasping serrated surfaces 480 of SULU 400.

Once disposable assembly 600 is loaded into channel member 206, anvil half-section 100 can be assembled to cartridge-receiving half-section 200 as shown in FIG. 2A. To attach anvil half-section 100 to cartridge-receiving half-section 200, protrusions 120 of fingers 118 are positioned in vertical slots 218 of vertical support member 216 of cartridge-receiving half-section 200. Thereafter, anvil half-section 100 is rotated towards cartridge-receiving half-section 200 to position lateral supports members 112 in U-shaped recesses 214. In this position, surgical stapler 10 is ready for use.

In use, with surgical stapler 10 in the open, or unclamped position, surgical stapler 10 is manipulated into position such that tissue to be stapled and divided is disposed between anvil half-section 100 and cartridge-receiving half-section 200. Thereafter, surgical stapler 10 may be moved to the clamped position to clamp tissue between SULU 400 and staple deforming portion 106 of anvil half section 100. In order to position surgical stapler 10 in the clamped position, clamping lever 300 is rotated in a counter-clockwise direction from the position shown in FIG. 2A after the anvil half section and cartridge receiving half section 200 are attached. As clamping lever 300 is rotated, against the bias of spring member 316 (FIG. 3), lateral support members 112 are received in cutouts 302 (FIG. 2) of flange portions 304 of clamp lever 300 and are cammed towards cartridge-receiving half-section 200. In the clamped position, as shown in FIG. 1, staple deforming portion 106 is positioned in close approximation with the top surface of SULU 400.

As shown in FIG. 27, as clamping lever 300 is moved towards the clamped position, an angled face 707 (FIG. 20) of latch portion 706 engages post 324. This engagement causes locking member 700 to pivot about pivot member 508 such that hook member 708 of latch portion 706 slides about the other surface of post 324 and, ultimately, snaps into engagement with post 324. To release latch portion 706 from post 324, i.e., to release clamping lever 300 from the clamped position, push-button 704 of locking member 700 is depressed to pivot latch portion 706 out of engagement with post 324. When this occurs, spring member 316 urges clamping lever 300 back to the unclamped position.

Referring to FIGS. 3, 12, 19 and 26, as discussed above, guide block 548 is pivotally supported in stationary housing 502 of firing unit 500. As surgical stapler 10 is moved to the clamped position, extensions 110 of anvil half-section 100 are approximated relative to disposable assembly 600 such that extensions 110 eventually contact the upper surface of guide block 548 and urge guide block 548 to pivot in a generally counter-clockwise direction (from the position shown in FIG. 19 to the position shown in FIG. 26). As guide block 548 is pivoted from the locked position to the unlocked position, locking surfaces 545, which are initially received in notches 549 and 551 of knife actuating bar 544 when the stapler 10 is in an unclamped position, are rotated out of notches 549, 551 to unlock knife actuating bar 544 (FIG. 26). This configuration prevents movement of the knife actuating bar 544 in relation to guide block 548 prior to clamping, thus ensuring that the knife actuating bar 544 and knife 440 remain properly positioned for operational engagement prior to use.

Referring to FIGS. 24-28, when stapler 10 is in the clamped, unfired position, slide block 552 of firing unit 500 is in the retracted position at the proximal end of channel member 206 and stationary housing 502 (see FIG. 27). In this position, pedal 554 is positioned in cutout 555 of channel member 206 and pin 588 of pedal 554 is positioned in arcuate recess 594 of firing lever 550 beneath stop recesses 594a. As such, firing lever 550 can be pivoted to facilitate actuation of stapler 10 from either side of the stapler 10. In addition, in this position of slide block 552, finger 599 of knife actuating bar 544 is positioned adjacent distal wall 553b of recess 553 of slide block 552. Latch portion 706 of locking member 700 is also engaged with post 324 to retain clamping lever 300 in the clamped position.

Referring to FIG. 26, when slide block 552 is in the retracted position, knife 440 and cam surfaces 547d of cam bar 546 are positioned in the proximal end of SULU 400 and, proximal hook 456 of safety lockout 428 is positioned in engagement with engagement member 458 of knife 440 to retain safety lockout 428 in the locked orientation. In addition, downturned hook portion 440b of knife 440 is engaged with upturned hook portion 598 of knife actuating bar 544 to connect firing unit 500 to knife 440 of SULU 400.

Figure 29:
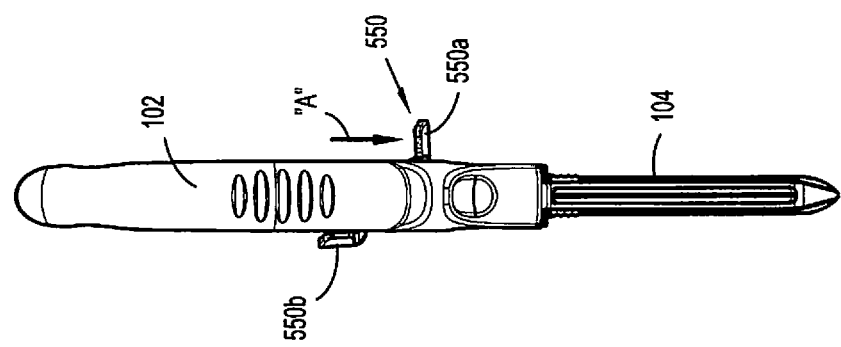
FIG. 29 is a top view of the surgical fastener applying apparatus shown in FIG. 1 as the firing unit is moved through an actuating stroke to eject fasteners from the SULU of the fastener applying apparatus.
Figure 28:
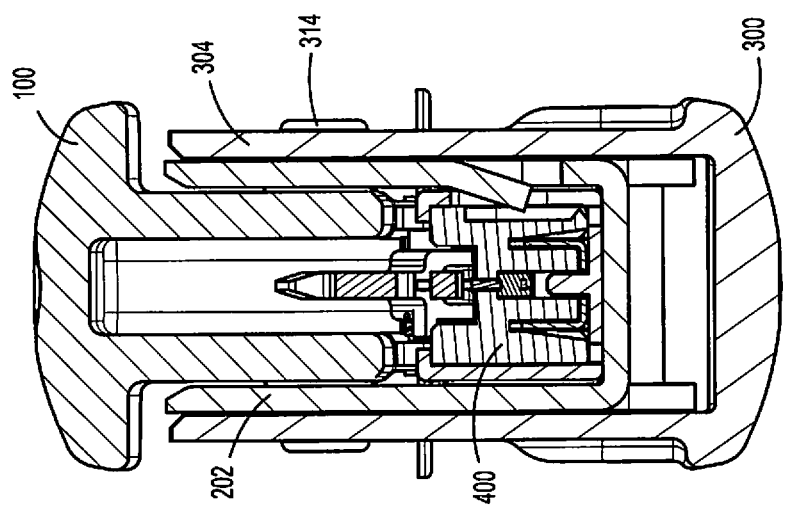
FIG. 28 is a cross-sectional view taken along section lines 28-28 of FIG. 26.

Referring to FIGS. 29-32, when the firing lever 550 is advanced distally in the direction indicated by arrow "A" in FIG. 29, slide block 552 is moved distally within stationary housing 502 of firing unit 500 to effect corresponding movement of cam bar 546 and delayed movement of knife actuating bar 544. As discussed above, the delayed movement of the knife actuating bar 544 is equal to the length of recess 553 of slide block 552 and results from movement of finger 599 of knife actuating bar 544 within recess 553 of slide block 552. Movement of knife actuating bar 544 with slide block 552 begins when finger 599 abuts the proximal wall 553a of recess 553. As cam bar 546 is moved distally through stationary housing 502 of firing unit 500, cam surfaces 547d on sidewalls 547 of cam bar 546 are advanced through SULU 400 to sequentially engage pushers 422 to eject staples 402 from slots 430 of body 420. Concurrently, since the distal end of knife actuating bar 544 is engaged with knife 440, knife 440, after the preset delay, is advanced through SULU 400 to incise tissue between the staple lines.

Figure 32:
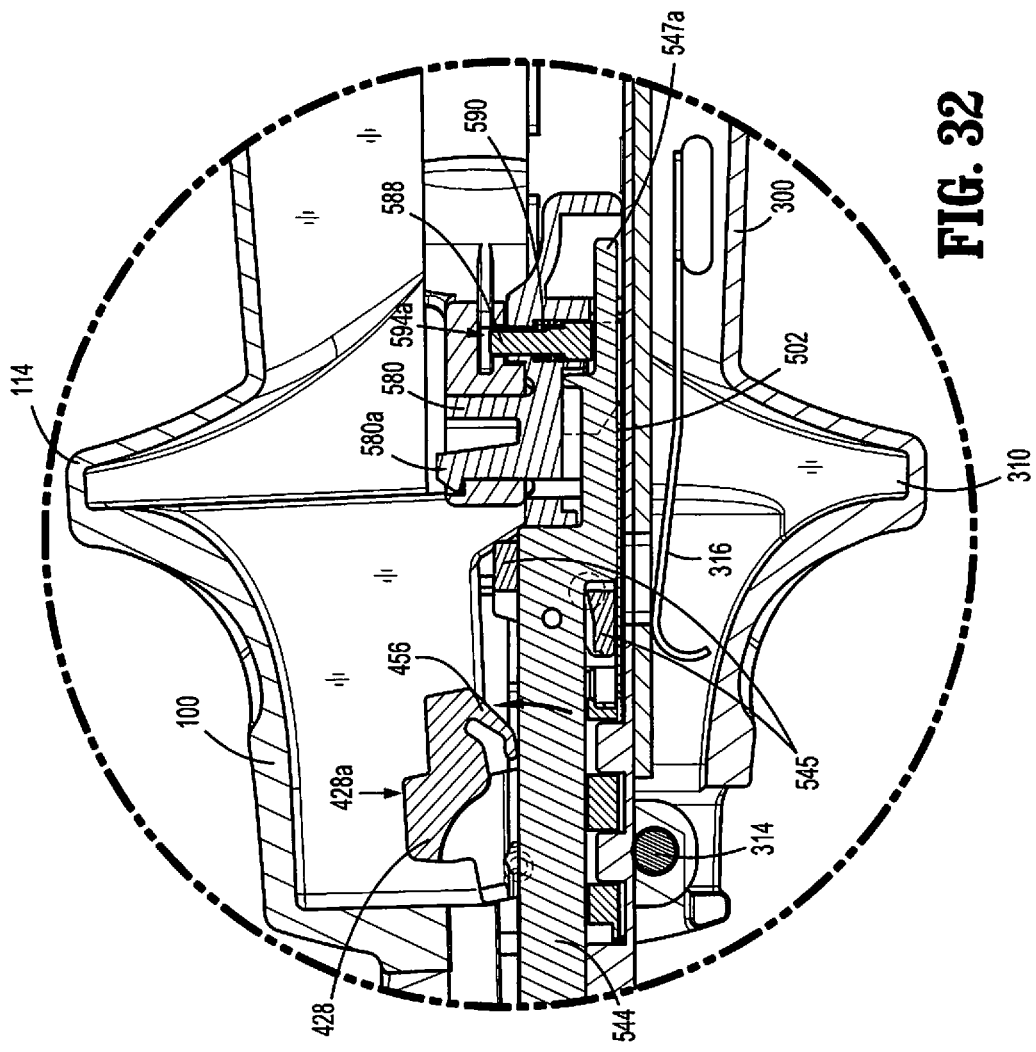
FIG. 32 is an enlarged view of the indicated area of detail shown in FIG. 30.

As shown in phantom in FIG. 32, when slide block 552 moves distally within stationary housing 502, pedal 554 rides up over channel member 206 and moves along inner surface of stationary housing 502 disposable assembly 600. When this occurs, pin 588 of pedal 554 moves into a stop recess 594a to prevent further pivotal movement of firing lever 550.

Figure 31:
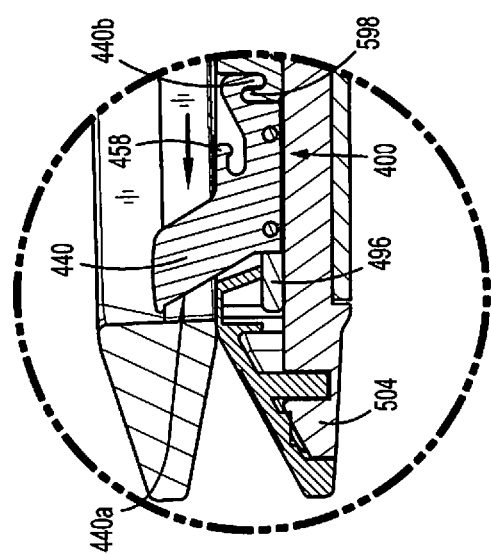
FIG. 31 is an enlarged view of the indicated area of detail shown in FIG. 30.

Referring to FIGS. 31 and 32, when knife 440 is moved distally within SULU 400, engagement member 458 of knife 440 is disengaged from proximal hook 456 of safety lockout 428.

Figure 33:
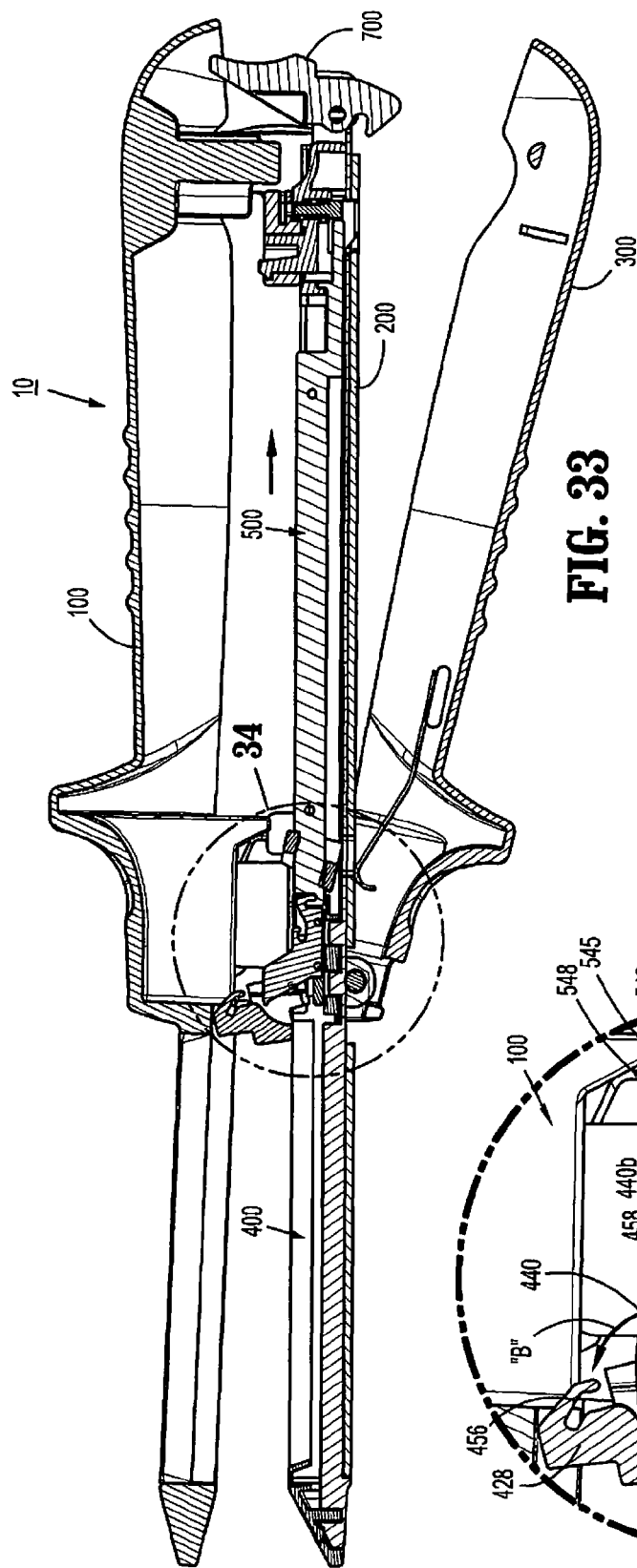
FIG. 33 is a side, cross-sectional view of the surgical fastener applying apparatus shown in FIG. 1 after the apparatus has been fired and moved to the open position.

Referring to FIGS. 33 and 34, when the firing lever 550 is returned to its proximal-most position to retract cam bar 546 and knife 440, and the locking member 700 is depressed to disengage latch portion 706 from post 324, spring 316 urges clamping lever 300 to its unclamped position to allow stapler 10 to move to the open position. In the open position, anvil half-section 100 is spaced from cartridge-receiving half-section 200 and spring 451 (FIG. 17) pivots safety lockout 428 in the direction indicated by arrow "B" in FIG. 34 about pivot member 250 to its unlocked position such that safety lockout 428 projects upwardly from SULU 400. In the unlocked position, safety lockout 428 prevents movement of the stapler 10 back to the clamped position. In order to reuse stapler 10, used SULU 400 must be replaced with a new SULU 400 by replacing the used disposable assembly 600 with a new disposable assembly 600.

During a surgical procedure, disposable assembly 600 (including SULU 400 and firing assembly 500) can be replaced multiple times to facilitate multiple uses of stapler 10 on a single patient. Each disposable assembly 600 is provided with a fresh knife. Further, each disposable assembly 600 is also provided with a fresh firing unit 500, e.g., a fresh cam bar 546, slide block 552, etc., thus inhibiting fatigue or wear of any of the components thereof and simplifying the number and form of components being resterilized. After the surgical procedure, the disposable assembly 600 can be removed from the channel member 206, e.g., via grasping and squeezing serrated surfaces 518 of stationary housing 502 and/or by grasping serrated surfaces 480 of SULU 400, and disposed of in an appropriate manner.

The anvil half-section 100, cartridge-receiving half-section 200 and clamping lever 300, on the other hand, can be sterilized, such as by autoclaving, and reused with a new disposable assembly 600 in the manner discussed above. Because the locking member 700, firing unit 500, and SULU 400 are all disposable, fewer areas remain on the reusable components for tissue and fluids to become trapped. As such, the reusable components of the apparatus can be more easily sterilized.

It will be understood that various modifications may be made to the embodiments of the surgical fastener applying apparatus disclosed herein. Therefore, the above description should not be construed as limiting, but merely as exemplifications of embodiments. Those skilled in the art will envision other modifications within the scope and spirit of the present disclosure.

What is claimed is:

1. A surgical fastener applying apparatus comprising:
  an anvil half-section including a distal anvil portion and a proximal handle portion;
  a cartridge-receiving half-section including an elongated channel member, the elongated channel member having a U-shaped configuration defined by sidewalls, and a closed lower portion, and an open upper portion, the cartridge-receiving half-section including a pair of opposed openings extending completely through the sidewalls of the elongated channel member from interior surfaces of the sidewalls to exterior surfaces of the sidewalls;
  a clamping lever secured to the cartridge receiving half-section, the clamping lever having a proximal end and a distal end and including a handle portion; and
  a disposable assembly including a single use loading unit and a single use firing unit, the disposable assembly configured to be releasably supported within the cartridge-receiving half-section and including a stationary housing for supporting the firing unit, the stationary housing including a distal extension extending therefrom for supporting the single use loading unit, the stationary housing including a pair of sidewalls each including a flared tab biased towards an at-rest position wherein the flared tabs extend outwardly at an angle relative to the sidewalls of the stationary housing, the flared tabs being configured to contact the sidewalls of the elongated channel member and flex inwardly towards an aligned orientation with respect to the sidewalls of the stationary housing upon insertion of the stationary housing through the open upper portion of the elongated channel member and into the elongated channel member, the flared tabs being configured to return under bias to the at-rest position upon alignment of the flared tabs with the opposed openings of the elongated channel member such that the flared tabs extend through the opposed openings of the side walls of the elongated channel member to protrude outwardly from the exterior surfaces of the sidewalls of the elongated channel member, and are thereby releasably received within the opposed openings of the elongated channel member to releasably engage the disposable assembly within the cartridge-receiving half-section; wherein the stationary housing includes a pair of outwardly-extending serrated gripping surfaces to facilitate insertion and removal of the disposable assembly in relation to the cartridge-receiving half-section;
  the clamping lever being operably associated with the anvil half-section and the cartridge receiving half-section and being movable from an unclamped position to a clamped position to releasably secure the anvil portion of the anvil half-section in close approximation with the single use loading unit.

2. The surgical fastener applying apparatus according to claim 1, wherein the stationary housing further defines a pair of opposed slots positioned towards a proximal end thereof and wherein the cartridge-receiving half-portion includes a pair of protrusions disposed at the proximal end thereof and extending inwardly from the sidewalls thereof, the protrusions configured to be received within the slots when the disposable assembly is positioned within the cartridge-receiving half-section.

3. The surgical fastener applying apparatus according to claim 1, wherein the disposable assembly further includes a pivotal locking member coupled to the stationary housing, the pivotal locking member being configured to engage an engagement member positioned on the clamping lever to lock the clamping member in the clamped position.

4. The surgical fastener applying apparatus according to claim 1, wherein the firing unit includes a firing lever and a cam bar fixedly secured to the firing lever, the firing lever being selectively translatable relative to the stationary housing to translate the cam bar through the single use loading unit to eject fasteners therefrom.

5. The surgical fastener applying apparatus according to claim 4, wherein the firing unit further includes a guide block pivotably supported within the stationary housing, the guide block being configured to guide translation of the cam bar through the single use loading unit, the guide block pivotable between a locked position inhibiting translation of the cam bar, and an unlocked position permitting translation of the cam bar.

6. The surgical fastener applying apparatus according to claim 5, wherein the anvil half-section includes at least one extension extending therefrom, the extension being configured to urge the guide block to the unlocked position upon movement of the clamping lever to the clamped position.

7. The surgical fastener applying apparatus according to claim 1, wherein the sidewalls of the stationary housing are manually movable toward each other to retract the flared tabs from the opposed openings to permit withdrawal of the stationary housing from the cartridge-receiving half section.

8. The surgical fastener applying apparatus according to claim 1, wherein the cartridge-receiving half-section includes cut-out portions defined at free ends of the sidewalls of the elongated channel member, the cut-out portions configured to receive the serrated gripping surfaces upon insertion of the disposable assembly into the cartridge-receiving half-section.

\* \* \* \* \*